US010266832B2

(12) United States Patent
Dodge et al.

(10) Patent No.: US 10,266,832 B2
(45) Date of Patent: Apr. 23, 2019

(54) FILAMENTOUS FUNGI HAVING AN ALTERED VISCOSITY PHENOTYPE

(75) Inventors: Timothy C. Dodge, Sunnyvale, CA (US); Aleksandra Virag, Cupertino, CA (US); Michael Ward, San Francisco, CA (US)

(73) Assignee: DANISCO US INC CA (US)

(*) Notice: Subject to any disclaimer, the term of this patent is extended or adjusted under 35 U.S.C. 154(b) by 203 days.

(21) Appl. No.: 13/817,421

(22) PCT Filed: Aug. 25, 2011

(86) PCT No.: PCT/US2011/049164
§ 371 (c)(1),
(2), (4) Date: Feb. 15, 2013

(87) PCT Pub. No.: WO2012/027580
PCT Pub. Date: Mar. 1, 2012

(65) Prior Publication Data
US 2013/0224864 A1 Aug. 29, 2013

Related U.S. Application Data

(60) Provisional application No. 61/377,030, filed on Aug. 25, 2010.

(51) Int. Cl.
| | |
|---|---|
| *C12N 15/80* | (2006.01) |
| *C07K 14/37* | (2006.01) |
| *C12N 1/14* | (2006.01) |
| *C12N 9/42* | (2006.01) |
| *C12N 9/34* | (2006.01) |
| *C12N 9/24* | (2006.01) |

(52) U.S. Cl.
CPC .............. *C12N 15/80* (2013.01); *C07K 14/37* (2013.01); *C12N 1/14* (2013.01); *C12N 9/2428* (2013.01); *C12N 9/2434* (2013.01); *C12N 9/2477* (2013.01); *C12Y 302/01003* (2013.01)

(58) Field of Classification Search
None
See application file for complete search history.

(56) References Cited

U.S. PATENT DOCUMENTS

| 5,246,853 A | 9/1993 | Clarkson et al. |
| 7,504,490 B1 | 3/2009 | Weinstock et al. |

FOREIGN PATENT DOCUMENTS

| WO | 95/16782 A1 | 6/1995 |
| WO | 08/156605 A1 | 12/2008 |
| WO | WO2009/035537 | 3/2009 |
| WO | WO/2011/038019 | 3/2011 |

OTHER PUBLICATIONS

Roberg et al. (Journal of Cell Biology, vol. 145 No. 4, pp. 659-672).*
Database accession No. AWP56142 sequence, "Aspergillus fumigatus ORF amino acid sequence Seq ID No. 27588", XP002666543, GSP:AWP56142, Oct. 14, 2010, 1pg.
Karhinen, et al., "Endoplasmic reticulum exit of a secretory glycoprotein in the absence of sec24p family proteins in yeast", Traffic, 2005, 6:562-74.
Altschul et al. (1990) "Basic local alignment search tool," J. Mol. Biol. 215:403-10.
Altschul et al. (1993) "Local alignment statistics," Meth. Enzymol. 266:460-80.
Caracuel et al. (2005) "Fusarium oxysporum gas1 Encodes a Putative β-1,3-Glucanosyltransferase Required for Virulence on Tomato Plants," Molecular Plant-Microbe Interactions 18:1140-47.
Devereux et al. (1984) "A comprehensive set of sequence analysis programs for the VAX," Nucleic Acids Res. 12:387-95.
Feng et al. (1987) "Progressive Sequence Alignment as a Prerequisite to Correct Phylogenetic Trees," J. Mol. Evol. 35:351-60.
Henikoff, et al. (1989) "Amino acid substitution matrices from protein blocks," Proc. Natl. Acad. Sci. USA 89:10915.
Higgins et al. (1989) "Fast and sensitive multiple sequence alignments on a microcomputer," CABIOS 5:151-53.
Higgins et al. (1988) "CLUSTAL: a package for performing mUltiple sequence alignment on a microcomputer," Gene 73:237-244).
Hughes et al. (2008) "Assembly, organization, and function of the COPII coat," Cell Biol. 129:129-51.
Karlin et al. ((1993), "Applications and statistics for multiple high-scoring segments in molecular sequences," Proc. Natl. Acad. Sci. USA 90:5873-87.
Kuck et al. (2010) "New tools for the genetic manipulation of filamentous fungi," Applied and Environmental Biotechnology 86:51-62).
Mouyna et al. (2005) Deletion of GEL2 encoding for aβ(1-3)glucanosyltransferase affects morphogenesis and virulence in Aspergillus fumigatus, Molecular Microbiology 56:1675-88.
Nakayashiki et al. (2008) "RNA interference: roles in fungal biology," Current Opinion in Microbiology 11:494-502.
Needleman et al. (1970) "A General Method Applicable to the Search for Similarities in the Amino Acid Sequence of Two Proteins," J. Mol. Biol., 48:443.
Passolunghi et al. (2010) "Cloning of the Zygosaccharomyces bailii GAS1 homologue and effect of cell wall engineering on protein secretory phenotype," Microbial Cell Factories 9:7-17.
Pearson et al. (1988) "Improved tools for biological sequence comparison," Proc. Natl. Acad. Sci. USA 85:2444.
Peng et al. (2000) "Evidence for Overlapping and Distinct Functions in Protein Transport of Coat Protein Sec24p Family Members," J. Biol. Chem. 275:11521-28.
Raponi et al. (2003) "Double-stranded RNA-mediated gene silencing in fission yeast," Nucleic Acids Research 31:4481-891.
Roberg et al. (1999) "LST1 is a SEC24 Homologue Used for Selective Export of the Plasma Membrane ATPase from the Endoplasmic Reticulum," J. Cell. Biol. 145:659-72.

(Continued)

Primary Examiner — Robert A Zeman

(57) ABSTRACT

Described are compositions and methods relating variant filamentous fungi having altered growth characteristics. Such variants are well-suited for growth in submerged cultures, e.g., for the large-scale production of enzymes and other proteins for commercial applications.

2 Claims, 12 Drawing Sheets

Specification includes a Sequence Listing.

(56) References Cited

OTHER PUBLICATIONS

Shimoni et al. (2000) "Lst1p and Sec24p Cooperate in Sorting of the Plasma Membrane ATPase into COPII Vesicles in *Saccharomyces cerevisiae*," J. Cell. Biol. 151:973-84.
Smith et al. (1981) "Comparison of biosequences," Adv. Appl. Math. 2:482.
Turchini et al. (2000) "Increase of External Osmolarity Reduces Morphogenetic Defects and Accumulation of Chitin in a gas1 Mutant of *Saccharomyces cerevisiae*," J. Becteriol. 182:1167-71.
Buer, et al., "Differences in optical trapping prompt investigations of Agrobacterium surface characteristics", J Ind Microbiol & Biotechnol, (1998), 21:233-6.
Database UniProt, Accession No. CAK42831, (2007), PEI, et al. http://www.ncbi.nlm.nih.gov/protein/134083191?sat=14&satkey=2579484
Parveen, et al., "the symbiotic phenotypes of exopolysaccharide-defective mutants of *rhizobium* sp. strain tal1145 do not differ on determinate- and indeterminate-nodulating tree legumes", Microbiol, (1997), 143:1959-67.

* cited by examiner

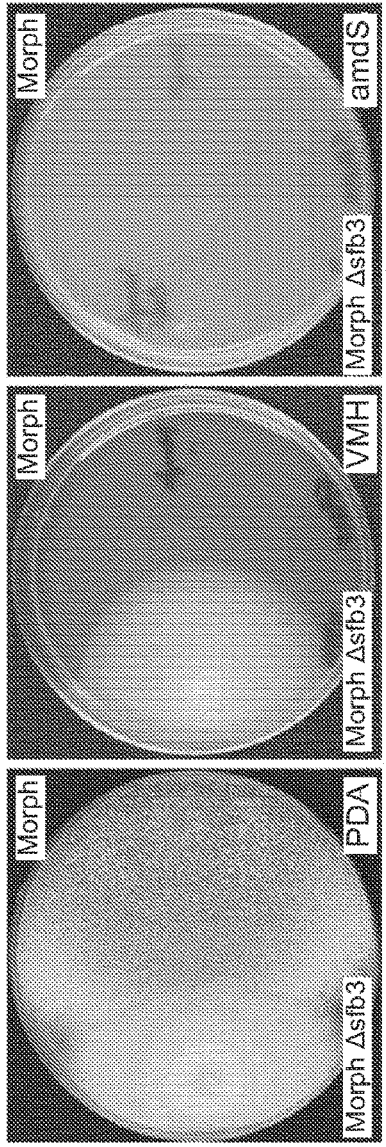

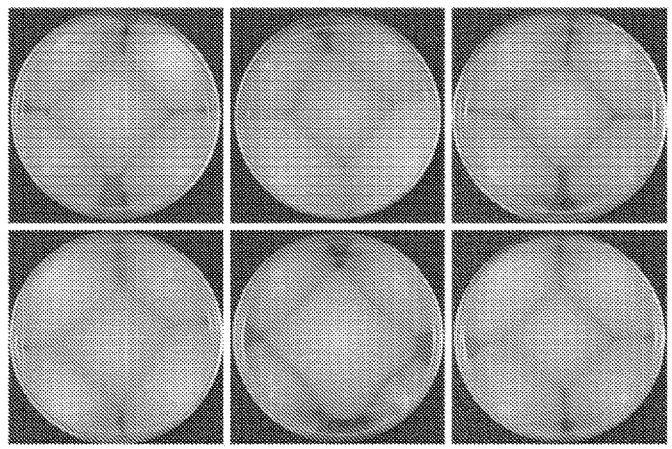
FIG. 8A  FIG. 8B  FIG. 8C
FIG. 8D  FIG. 8E  FIG. 8F
FIG. 8G
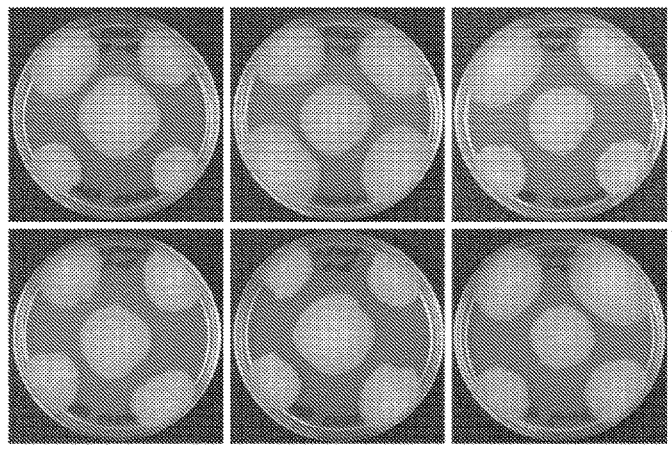
FIG. 8H  FIG. 8I  FIG. 8J
FIG. 8K  FIG. 8L  FIG. 8M
FIG. 8N

```
S.cerevisiae  ----------------------------------------------------------------
T.reesei      MDYTQYHALGHGEVLDPNDPNKTSAPAAPQFQPPSSPYVPPGSPYGAPPYHGGHQAPPMA S.cerevisiae  -------------------MSQQNILAASVSALSLDESTVHTGGASSKKSRRPHRAYHNF
T.reesei      MPPPSTPGYGPPQGQSFPGSPMPSQDAGLAAQFGGMSLGADAGGAAARKKKKDRHAYHSV
                                 .  .*..: :.   ...:***::*.::  ::***..

S.cerevisiae  S-SGTVPTLG---------------NSPYTTPQLNQQDG------FQQPQAFTPKQFGGFN
T.reesei      EPTGSSQAFNGLPPGTPAEQFLNVNNPQGIPALGGQFGSPLASPMGTPHMANPGQFPAPT
                .:*:  ::.              *.*   * *. *          :   *: .* **  . .

S.cerevisiae  NGSGSVMSTPVMVSQERFGASEASSPYGQSMLDMTAPQPTSHIVPTQRFEDQAQYLQRSF
T.reesei      SPFTPSAPVSPAEFASRFGSPDAATSIGSAGPSQVSPD-DMPSIPASRDAIQEHFFKNVY
                .  .   ...  .***:.:*::.  *.:  . ..:*:     :*:.*    * :::. :

S.cerevisiae  ETCRDSVPPLPTTQFYCVDQGSCDPHLMSLSMYNIPESEHLRAATKLPLGLTIQPFSTLT
T.reesei      PTFERHVPPPATVSFVAFDQGNASPKFTRLTLNNIPTTAEGLHATGLPLGMLIQPLAPLQ
               *  .  *** .*..*  ..***...*::   *:: *** : .   ** ****: ***::.*

S.cerevisiae  PNDAEVPTIPLPMDGTPLRCRRCRAYANPKFQFTYDSS-VICNICRVKMQVPGEHFAPMG
T.reesei      AGEAEIPVLDFGDAG-PPRCRRCRAYINPFMMFRSGGNKFVCNLCSYPNETPPEYFCAVS
               ..:**:*.: :    * * ******** ** : *    ... .:**:*     :.* *:*...:.

S.cerevisiae  PNGQRSDLNEKSELLHGTVDFLVPSIYNAIQEKELLPLHYVFLIDVSLLANENGSSLAMV
T.reesei      PQGVRLDRDQRPELHRGTVEFVVPKEY---WTREPVGLRWLFIDVTQESYNKGFMETFC
              *:*  *   *   :::.**  :***:*.**,  *         :*  * *::*:****:    :  ::*    ::

S.cerevisiae  EGVRSCIEYISDFQPN-------------CEVAIIVYDNKLRFFNLRPDLDNAQEYIVSEL
T.reesei      EGILAALYGGNDEENDEDGEPKRRIPKGAKVGFITYDKDIHFYNINPHLDQAHMMIMPDL
              **: :.:    .* : :          ..:*.:*.**:.::*:*:.*,.**:*:   *:.:*

S.cerevisiae  DDVFLPFYNGLFVKPGNSMKIINDTLIKISGYISTDKYSHVPQVCYGSALQAAKLALDTV
T.reesei      EDPFLPLGEGLFVDPYESKAIITSLLTRLPEMFSTIKN---PEPALLATLNAAVAALEAT
              :* ***: :****.* :* **..  * ::.  :** *     *: .  ::*:** **::.

S.cerevisiae  TGGQGGKIICSLNSLPTIGNGNLSLKRDNAHIAH------VKCDNGFYKKLASDFLKSYI
T.reesei      ----GGKVVCSCSTLPTWGPGRLFMRDDGNHPGGELDKKLYTTEHPAWKKVSEKMASSGI
                  ***::**  .:*** * *.* :: *, *  .        . ::  :**::..: .* *

S.cerevisiae  SLDLYVTN--AGFIDMATVGHPVEMTSGILKYYPHFQQETDAFTLVNDMVTNVSNIVGYQ
T.reesei      GVDFFLAAPSGGYLDIATIGHVAATTGGETFYYPNFIAPRDGARLSMEITHAITRETGFQ
              .:*::::    .*::*:**:**  .  *.* ***:*  *. * ::  ::  ::..*:*

S.cerevisiae  ALLKVRCSTGLSVEQYYCDSSDNTD-HDPIIPVLTRDTTLDVLLKYDSKIKTGTDVHFQT
T.reesei      ALMKVRCSTGLQVAAYHGNFVQHTFGADLEIGVIDADKALGVSFSHDGKLDPKLDAHFQT
              **:********.*  *: :   ::*   *  * *:  *.:*.* ..:*.*..   *.****

S.cerevisiae  ALLYTDIDGVRKVRSINTGAVSNN----------IREIFKFINQNPVMRIMIKDVIKTL
T.reesei      ALLYTTASGQRRVRCSNVIASVSDTSKESNTKELAIRQCLKFVDQDAVVGIFAKEASTKL
              *****  .*  :***. *  :.:**:.         **: :**::*.*:  *: .  ..:*
```

*FIG. 13A*

```
S.cerevisiae  G--DCDFVKIRRLIDDKMVEILTQYRGLVSSNSS-TQLILPDSIKTLPAYMLAFEKSELM
T.reesei      ATTSANLQDVRNWLTERTIDIMAYYKKHSANQFPPSQLVMPERLKEFCMYMLGMLKCRAF
              .  ..::  .:*.  :  ::  ::*::  *:       :.:  .  :**::*:  :*  :   ***.:  *.. :

S.cerevisiae  KPNAQSTRGNERIYDLLKYDSLNSAQLCYKLYPQIVPFHVLLEETDLTFYDANDKLLQIN
T.reesei      KGGIENS--DRRVHELRMVRSMGPLELSLYLYPRMIALHNLQPEEGFADPETGHLKMPP-
              *  .  :.:    :.*:::*      *:..  :*.   ***:::.:*  *    *  .::   ::..    :

S.cerevisiae  SSSINNLSVRASHSNFINGGCYLIFQGDTIYLWFNENTNRMLLQDLLSVDESLPVSQISL
T.reesei      -------SVRTSFSRVEPGGVYLVDNGQQCLLWFHAQTSPNLITDLFGEGHDS-LKGLDP
                     ***:*.*..   ** **:  :*:      ***:  :*.    *:  **:.  ...    :.  :.

S.cerevisiae  FSGTLPETGTSINQKASNVIKNWQQVVNKSSLPLVLLRPNVDQYYSNVMSQLLCEDKTVN
T.reesei      YTSTLPVLETHLSAQVRNIIEFLKSMRGSKGMTIQLARQGIDG-AEYEFARMLVEDR-NN
              ::.***    *  :.  :.  *:*:  :.:    ....:..:  *   *  .:*      .    :::::*  **:    *

S.cerevisiae  RIESYDNYLVIMHKKIQEKLQKDDFIKVSTAATHENIHQKFVQF---(SEQ ID NO: 1)
T.reesei      EAKSYVDWLVHIHRGVQLELSGQRKKEGDGEATAVMANFAGLRPAYW(SEQ ID NO: 2)
              .  :**  ::**  :*:  :*  :*.  :        :    .    **        :      ::
```

FIG. 13B

```
T.reesei        -MDYTQYHALGHG--EVLDPNDPNKTSAPAAPQFQ-----PPSSPYVPPGSPYGAPP---
A.oryzae        MADQSMYNTLGQGTSPAEDPSNPNRMAHQVPPQSQPAAGFPPGPYPPQPGAYYGNPPPNQ
S.cerevisiae    ---MSQQNILAASVSALSLDESTVHTGGASSKKSR-------------------------
                   :  *..       ...  :..    . ::

T.reesei        YHGGHQAPPMAMPPPSTPGYGPPQGQSFPGSPMPSQD--------AGLAAQFGGMSLGADA
A.oryzae        YDAPAAAPPTQQLQSPPPRGLAPSPQLAYGTETQTHMGAPADPMAGLASQMSGLGIMGDS
S.cerevisiae    --------RPHRAYHNFSSGTVPTLGNSPYTTPQLNQQDGFQQPQAFTPKQFGGFNNGSGS
                         *  ..   ..  :    :   .:        *  .  *:.*::.   ...:

T.reesei        GGAAARKKKKDRHAYHSVEPTGSSQAFNGLPPG--TPAEQFLNVNNPQGIPALGGQFGSP
A.oryzae        GARPGKKKHRHAHHEIGGATASAPQQFAGMPQAGMQPSSQFLNTGLNQAPRPISPAAGVP
S.cerevisiae    ----------------VMSTPVMVSQERFGASEASSPYGQSMLDMTAPQPT---------
                                 ..  .*   *  .      ...:*:      *

T.reesei        LASPMGTPHMANPGQFPAPTSPFTPSAPVSPAEFASRFGSPDAATSIGSAGPSQVSPDDM
A.oryzae        PAGIVPQPGVPAPGSGSVPT----------------------------QGKIDPEQI
S.cerevisiae    ------------------------------------------------------------S T.reesei        PSIPASRDAIQEHFFKNVYPTFERHVPPPATVSFVAFDQGNASPKFTRLTLNNIPTTAEG
A.oryzae        PSIPQSRDIPTMYYFDHIYPTMERHLPPPAAVPFVAHDQGNSSPKHARLTLNNIPTTSDF
S.cerevisiae    HIVPTQRFEDQAQYLQRSFETCRDSVPPLPTTQFYCVDQGSCDPHLMSLSMYNIPESEHL
                 :* .*       ::.. : * .  :**  .:. * . ***...*:  *::  *** : .

T.reesei        LHATGLPLGMLIQPLAPLQAGEAEIPVLDFGDAG--PPRCRRCRAYINPFMMFRSGGNKFV
A.oryzae        LSSTALPLGMVLQPLARLDPGEPEVPVLDFGEMG--PPRCRRCRAYINPFMTFRSGGNKFV
S.cerevisiae    RAATKLPLGLTIQPFSTLTPNDAEVPTIPLPMDGTPLRCRRCRAYANPKFQFTYDSS-VI
                :*  ****: :**:: *   ..:.:*:., :    * * ********  **  : *    ...  .:

T.reesei        CNLCSYPNETPPEYFCAVSPQGVRLDRDQRPELHRGTVEFVVPKEY---WTREPVGLRWL
A.oryzae        CNMCTFPNDVAPEYFAPLDMSGARVDRLQRPELMIGTVEFMVPKEY---WNKEPVGLQRL
S.cerevisiae    CNICRVKMQVPGEHFAPMGPNGQRSDLNEKSELLHGTVDFLVPSIYNAIQEKELLPHYV
                **:*       :.. *:*..:. .* * *   ::.**  ***:*:**. *       :* : *:  ;

T.reesei        FVIDVTQESYNKGFMETFCEGILAALYGGNDEENDEDGEPKRRIPKGAKVGFITYDKDIH
A.oryzae        FLIDVSQESVNRGFLKGVCKGITEALYGAPDAS--EEDAAARRVPEGSKIGIVTYDREVH
S.cerevisiae    FLIDVSLLANENGSSLAMVEGVRSCIEYISDFQP-------------NCEVAIIVYDNKLR
                *:***:  :  :.*   . :*   . :*:  :  *  .           ..:::.::.**..::

T.reesei        FYNINPHLDQAHMMIMPDLEDPFLPLGEGLFVDPYESKAIITSLLTRLPEMFSTIKNPEP
A.oryzae        FYNLSAQLDQAQMMVMTDLEEPFVPLSEGLFVDPYESKDIITSLLHRIPKIFSHIKKPEP
S.cerevisiae    FFNLRPDLDNAQEYIVSELDDVFLPFYNGLFVKPN.* :* **.. * ::. :*   *  .

T.reesei        --------ALLATLNAAVAALEATGGKVVCSCSTLPTWGPGRLFMRDDGNHPGGELDKKLY
A.oryzae        --------ALLPALNAAMSALQATGGKIFASICSLPTWGPGALHMRDDPKVHGTDAERKLF
S.cerevisiae    PQVCYGSALQAAKLALDTVTGGQGGKIICSLNSLPTIGNGNLSLKRD-------NAHIAHV
                         **  .:  *   :. .  ***:.. * :*** * * *  ::   *    :  .

T.reesei        TTEHPAWKKVSEKMASSGIGVDFFLAAPSGGYLDIATIGHVAATTGGETFYYPNFIAPRD
A.oryzae        TTDNQAWRTTAGKMAEHGIGVDMFVAAPGGTYVDVATIGHVAEVSGGETFFYPNFHAPRD
S.cerevisiae    KCDNGFYKKLASDFLKSYISLDLYVTNAG--FIDMATVGHPVEMTSGILKYYPHFQQETD
                . ::  ::. .. :. .  *.::*:::  .. ::*:**:**  . .*   :**:*      *
```

*FIG. 14A*

```
T.reesei       GARLSMEITHAITRETGFQALMKVRCSTGLQVAAYHGNFVQHTFGADLEIGVIDADKALG
A.oryzae       ILKLSQEFAHAVTRETGYQAMMKVRCSNGLQVSAYHGNFIQHALGADLEIGSIDADKAIG
S.cerevisiae   AFTLVNDMVTNVSNIVGYQALLKVRCSTGLSVEQYYCDSSDNTD-HDPIIPVLTRDTTLD
                 *  ::.   ::. .*:**::*****.**.*  *: :  :::   *   *   :  *.::.

T.reesei       VSFSHDGKLDPKLDAHFQTALLYTTASGQRRVRCSNVIASVSDTSKESNTKELAIRQCLK
A.oryzae       VMFSYDGKLDPKLDAHFQAALLYTTAEGQRRVRCINVVAAVNEGGLET---------MK
S.cerevisiae   VLLKYDSKIKTGTDVHFQTALLYTDIDGVRKVRSINTSGAVSNN----------IREIFK
                * :.:*.*:..  *.***:*****  .* *:**. *. ..:*.:             :*

T.reesei       FVDQDAVVGIFAKEASTKLATTSANLQDVRNWLTERTIDIMAYYKKHSANQFPPSQLVMP
A.oryzae       FIDQDCVVSIMAKEAAAKTVDK--SLKDIRASITEKTVDIFSGYRKVFSGSHPPGQLVLP
S.cerevisiae   FINQNPVMRIMIKDVIKTLGDC--DFVKIRRLIDDKMVEILTQYRGLVS-SNSSTQLILP
                *::*: *: *: *:.  .   .: :.:* : :: ::*:: *:  :  .  .. **::*

T.reesei       ERLKEFCMYMLGMLKCRAFKGGIENS--DRRVHELRMVRSMGPLELSLYLYPRMIALHNL
A.oryzae       ENLKEFSMYMLALIKSRAFKGGQEAS--DRRIHDMRMLRSIGATELALYLYPRVIPIHNM
S.cerevisiae   DSIKTLPAYMLAFEKSELMKPNAQSTRGNERIYDLLKYDSLNSAQLCYKLYPQIVPFHVL
               : :* :   ***.: *.. :* . : :  :.*:::::    *:.. :*.  ***:::.:*
:

T.reesei       QPEEGFADPETGHLKMPP---------SVRTSFSRVEPGGVYLVDNGQQCLLWFHAQTSPN
A.oryzae       QPEDGFPN-EQGQLQVPP---------SLRASFSKIEEGGAYLVDNGQICLLWLHSRVSPN
S.cerevisiae   LEETDLTFYDANDKLLQINSSSINNLSVRASHSNFINGGCYLIFQGDTIYLWFNENTNRM
                   * ..:.  :   ... :           *:*:*.*..  ** **: :*:  **::  ...

T.reesei       LITDLFGEGHDS-LKGLDPYTSTLPVLETHLSAQVRNIIEFLKSMRGSKGMTIQLARQGI
A.oryzae       LLEDLLGPGQSS-LQGLNPQTSSLPVLETHLNAQVRNLLQYFSTMRGSKSVAIQLARQGL
S.cerevisiae   LLQDLLSVDESLPVSQISLFSGTLPETGTSINQKASNVIKNWQQVVNKSSLPLVLLRPNV
               *: **:. ...  :. :.  :.:**   * :.  *::: .:   ....:.: * * .:

T.reesei       DGAEYEFARMLVEDRN--NEAKSYVDWLVHIHRGVQLELSGQRKKEGDGEATAVMANFAG
A.oryzae       DGAEYEFARLLVEDRN--NEAQSYVDWLVHIHRQINLELAGHRKRE-DTSAEGSLTSLAG
S.cerevisiae   DQYYSNVMSQLLCEDKTVNRIESYDNYLVIMHKKIQEKLQKDDFIKVSTAATHENIHQKF
                 *      :.  *: : :   *. :** ::** :*: ::  ::*   .    :  *

T.reesei       LRPAYW    (SEQ ID NO: 2)
A.oryzae       LRAPYW    (SEQ ID NO: 3)
S.cerevisiae   VQF---    (SEQ ID NO: 1)
                ::
```

*FIG. 14B*

SEQUENCE LISTING

```
<160> NUMBER OF SEQ ID NOS: 40

<210> SEQ ID NO 1
<211> LENGTH: 929
<212> TYPE: PRT
<213> ORGANISM: Saccharomyces cerevisiae

<400> SEQUENCE: 1

Met Ser Gln Gln Asn Ile Leu Ala Ala Ser Val Ser Ala Leu Ser Leu
1               5                   10                  15

Asp Glu Ser Thr Val His Thr Gly Gly Ala Ser Ser Lys Lys Ser Arg
            20                  25                  30

Arg Pro His Arg Ala Tyr His Asn Phe Ser Ser Gly Thr Val Pro Thr
        35                  40                  45

Leu Gly Asn Ser Pro Tyr Thr Thr Pro Gln Leu Asn Gln Gln Asp Gly
    50                  55                  60

Phe Gln Gln Pro Gln Ala Phe Thr Pro Lys Gln Phe Gly Gly Phe Asn
65                  70                  75                  80

Asn Gly Ser Gly Ser Val Met Ser Thr Pro Val Met Val Ser Gln Glu
                85                  90                  95

Arg Phe Gly Ala Ser Glu Ala Ser Ser Pro Tyr Gly Gln Ser Met Leu
            100                 105                 110

Asp Met Thr Ala Pro Gln Pro Thr Ser His Ile Val Pro Thr Gln Arg
        115                 120                 125

Phe Glu Asp Gln Ala Gln Tyr Leu Gln Arg Ser Phe Glu Thr Cys Arg
    130                 135                 140

Asp Ser Val Pro Pro Leu Pro Thr Thr Gln Phe Tyr Cys Val Asp Gln
145                 150                 155                 160

Gly Ser Cys Asp Pro His Leu Met Ser Leu Ser Met Tyr Asn Ile Pro
                165                 170                 175

Glu Ser Glu His Leu Arg Ala Ala Thr Lys Leu Pro Leu Gly Leu Thr
            180                 185                 190

Ile Gln Pro Phe Ser Thr Leu Thr Pro Asn Asp Ala Glu Val Pro Thr
        195                 200                 205

Ile Pro Leu Pro Met Asp Gly Thr Pro Leu Arg Cys Arg Arg Cys Arg
    210                 215                 220

Ala Tyr Ala Asn Pro Lys Phe Gln Phe Thr Tyr Asp Ser Ser Val Ile
225                 230                 235                 240

Cys Asn Ile Cys Arg Val Lys Met Gln Val Pro Gly Glu His Phe Ala
                245                 250                 255
```

```
Pro Met Gly Pro Asn Gly Gln Arg Ser Asp Leu Asn Glu Lys Ser Glu
            260                 265                 270

Leu Leu His Gly Thr Val Asp Phe Leu Val Pro Ser Ile Tyr Asn Ala
        275                 280                 285

Ile Gln Glu Lys Glu Leu Leu Pro Leu His Tyr Val Phe Leu Ile Asp
    290                 295                 300

Val Ser Leu Leu Ala Asn Glu Asn Gly Ser Ser Leu Ala Met Val Glu
305                 310                 315                 320

Gly Val Arg Ser Cys Ile Glu Tyr Ile Ser Asp Phe Gln Pro Asn Cys
                325                 330                 335

Glu Val Ala Ile Ile Val Tyr Asp Asn Lys Leu Arg Phe Phe Asn Leu
            340                 345                 350

Arg Pro Asp Leu Asp Asn Ala Gln Glu Tyr Ile Val Ser Glu Leu Asp
        355                 360                 365

Asp Val Phe Leu Pro Phe Tyr Asn Gly Leu Phe Val Lys Pro Gly Asn
370                 375                 380

Ser Met Lys Ile Ile Asn Asp Thr Leu Ile Lys Ile Ser Gly Tyr Ile
385                 390                 395                 400

Ser Thr Asp Lys Tyr Ser His Val Pro Gln Val Cys Tyr Gly Ser Ala
                405                 410                 415

Leu Gln Ala Ala Lys Leu Ala Leu Asp Thr Val Thr Gly Gly Gln Gly
            420                 425                 430

Gly Lys Ile Ile Cys Ser Leu Asn Ser Leu Pro Thr Ile Gly Asn Gly
        435                 440                 445

Asn Leu Ser Leu Lys Arg Asp Asn Ala His Ile Ala His Val Lys Cys
450                 455                 460

Asp Asn Gly Phe Tyr Lys Lys Leu Ala Ser Asp Phe Leu Lys Ser Tyr
465                 470                 475                 480

Ile Ser Leu Asp Leu Tyr Val Thr Asn Ala Gly Phe Ile Asp Met Ala
                485                 490                 495

Thr Val Gly His Pro Val Glu Met Thr Ser Gly Ile Leu Lys Tyr Tyr
            500                 505                 510

Pro His Phe Gln Gln Glu Thr Asp Ala Phe Thr Leu Val Asn Asp Met
        515                 520                 525

Val Thr Asn Val Ser Asn Ile Val Gly Tyr Gln Ala Leu Leu Lys Val
530                 535                 540

Arg Cys Ser Thr Gly Leu Ser Val Glu Gln Tyr Tyr Cys Asp Ser Ser
545                 550                 555                 560

Asp Asn Thr Asp His Asp Pro Ile Ile Pro Val Leu Thr Arg Asp Thr
                565                 570                 575

Thr Leu Asp Val Leu Leu Lys Tyr Asp Ser Lys Ile Lys Thr Gly Thr
            580                 585                 590

Asp Val His Phe Gln Thr Ala Leu Leu Tyr Thr Asp Ile Asp Gly Val
        595                 600                 605

Arg Lys Val Arg Ser Ile Asn Thr Ser Gly Ala Val Ser Asn Asn Ile
610                 615                 620

Arg Glu Ile Phe Lys Phe Ile Asn Gln Asn Pro Val Met Arg Ile Met
625                 630                 635                 640

Ile Lys Asp Val Ile Lys Thr Leu Gly Asp Cys Asp Phe Val Lys Ile
                645                 650                 655

Arg Arg Leu Ile Asp Asp Lys Met Val Glu Ile Leu Thr Gln Tyr Arg
            660                 665                 670

Gly Leu Val Ser Ser Asn Ser Ser Thr Gln Leu Ile Leu Pro Asp Ser
```

```
                675                 680                 685
Ile Lys Thr Leu Pro Ala Tyr Met Leu Ala Phe Glu Lys Ser Glu Leu
        690                 695                 700
Met Lys Pro Asn Ala Gln Ser Thr Arg Gly Asn Glu Arg Ile Tyr Asp
705                 710                 715                 720
Leu Leu Lys Tyr Asp Ser Leu Asn Ser Ala Gln Leu Cys Tyr Lys Leu
                725                 730                 735
Tyr Pro Gln Ile Val Pro Phe His Val Leu Glu Glu Thr Asp Leu
            740                 745                 750
Thr Phe Tyr Asp Ala Asn Asp Lys Leu Leu Gln Ile Asn Ser Ser Ser
        755                 760                 765
Ile Asn Asn Leu Ser Val Arg Ala Ser His Ser Asn Phe Ile Asn Gly
    770                 775                 780
Gly Cys Tyr Leu Ile Phe Gln Gly Asp Thr Ile Tyr Leu Trp Phe Asn
785                 790                 795                 800
Glu Asn Thr Asn Arg Met Leu Leu Gln Asp Leu Leu Ser Val Asp Glu
                805                 810                 815
Ser Leu Pro Val Ser Gln Ile Ser Leu Phe Ser Gly Thr Leu Pro Glu
            820                 825                 830
Thr Gly Thr Ser Ile Asn Gln Lys Ala Ser Asn Val Ile Lys Asn Trp
        835                 840                 845
Gln Gln Val Val Asn Lys Ser Ser Leu Pro Leu Val Leu Leu Arg Pro
    850                 855                 860
Asn Val Asp Gln Tyr Tyr Ser Asn Val Met Ser Gln Leu Leu Cys Glu
865                 870                 875                 880
Asp Lys Thr Val Asn Arg Ile Glu Ser Tyr Asp Asn Tyr Leu Val Ile
                885                 890                 895
Met His Lys Lys Ile Gln Glu Lys Leu Gln Lys Asp Asp Phe Ile Lys
            900                 905                 910
Val Ser Thr Ala Ala Thr His Glu Asn Ile His Gln Lys Phe Val Gln
        915                 920                 925
Phe

<210> SEQ ID NO 2
<211> LENGTH: 1042
<212> TYPE: PRT
<213> ORGANISM: Trichoderma reesei

<400> SEQUENCE: 2

Met Asp Tyr Thr Gln Tyr His Ala Leu Gly His Gly Glu Val Leu Asp
1               5                   10                  15
Pro Asn Asp Pro Asn Lys Thr Ser Ala Pro Ala Pro Gln Phe Gln
            20                  25                  30
Pro Pro Ser Ser Pro Tyr Val Pro Gly Ser Pro Tyr Gly Ala Pro
        35                  40                  45
Pro Tyr His Gly Gly His Gln Ala Pro Met Ala Met Pro Pro
    50                  55                  60
Ser Thr Pro Gly Tyr Gly Pro Pro Gln Gly Gln Ser Phe Pro Gly Ser
65                  70                  75                  80
Pro Met Pro Ser Gln Asp Ala Gly Leu Ala Ala Gln Phe Gly Gly Met
                85                  90                  95
Ser Leu Gly Ala Asp Ala Gly Gly Ala Ala Ala Arg Lys Lys Lys Lys
            100                 105                 110
Asp Arg His Ala Tyr His Ser Val Glu Pro Thr Gly Ser Ser Gln Ala
```

-continued

```
                115                 120                 125
Phe Asn Gly Leu Pro Pro Gly Thr Pro Ala Glu Gln Phe Leu Asn Val
        130                 135                 140
Asn Asn Pro Gln Gly Ile Pro Ala Leu Gly Gly Gln Phe Gly Ser Pro
145                 150                 155                 160
Leu Ala Ser Pro Met Gly Thr Pro His Met Ala Asn Pro Gly Gln Phe
                165                 170                 175
Pro Ala Pro Thr Ser Pro Phe Thr Pro Ser Ala Pro Val Ser Pro Ala
                180                 185                 190
Glu Phe Ala Ser Arg Phe Gly Ser Pro Asp Ala Thr Ser Ile Gly
                195                 200                 205
Ser Ala Gly Pro Ser Gln Val Ser Pro Asp Met Pro Ser Ile Pro
        210                 215                 220
Ala Ser Arg Asp Ala Ile Gln Glu His Phe Phe Lys Asn Val Tyr Pro
225                 230                 235                 240
Thr Phe Glu Arg His Val Pro Pro Ala Thr Val Ser Phe Val Ala
                245                 250                 255
Phe Asp Gln Gly Asn Ala Ser Pro Lys Phe Thr Arg Leu Thr Leu Asn
                260                 265                 270
Asn Ile Pro Thr Thr Ala Glu Gly Leu His Ala Thr Gly Leu Pro Leu
                275                 280                 285
Gly Met Leu Ile Gln Pro Leu Ala Pro Leu Gln Ala Gly Glu Ala Glu
        290                 295                 300
Ile Pro Val Leu Asp Phe Gly Asp Ala Gly Pro Pro Arg Cys Arg Arg
305                 310                 315                 320
Cys Arg Ala Tyr Ile Asn Pro Phe Met Met Phe Arg Ser Gly Gly Asn
                325                 330                 335
Lys Phe Val Cys Asn Leu Cys Ser Tyr Pro Asn Glu Thr Pro Pro Glu
                340                 345                 350
Tyr Phe Cys Ala Val Ser Pro Gln Gly Val Arg Leu Asp Arg Asp Gln
                355                 360                 365
Arg Pro Glu Leu His Arg Gly Thr Val Glu Phe Val Val Pro Lys Glu
        370                 375                 380
Tyr Trp Thr Arg Glu Pro Val Gly Leu Arg Trp Leu Phe Val Ile Asp
385                 390                 395                 400
Val Thr Gln Glu Ser Tyr Asn Lys Gly Phe Met Glu Thr Phe Cys Glu
                405                 410                 415
Gly Ile Leu Ala Ala Leu Tyr Gly Gly Asn Asp Glu Asn Asp Glu
                420                 425                 430
Asp Gly Glu Pro Lys Arg Arg Ile Pro Lys Gly Ala Lys Val Gly Phe
                435                 440                 445
Ile Thr Tyr Asp Lys Asp Ile His Phe Tyr Asn Ile Asn Pro His Leu
        450                 455                 460
Asp Gln Ala His Met Met Ile Met Pro Asp Leu Glu Asp Pro Phe Leu
465                 470                 475                 480
Pro Leu Gly Glu Gly Leu Phe Val Asp Pro Tyr Glu Ser Lys Ala Ile
                485                 490                 495
Ile Thr Ser Leu Leu Thr Arg Leu Pro Glu Met Phe Ser Thr Ile Lys
                500                 505                 510
Asn Pro Glu Pro Ala Leu Leu Ala Thr Leu Asn Ala Ala Val Ala Ala
                515                 520                 525
Leu Glu Ala Thr Gly Gly Lys Val Val Cys Ser Cys Ser Thr Leu Pro
        530                 535                 540
```

Thr Trp Gly Pro Gly Arg Leu Phe Met Arg Asp Asp Gly Asn His Pro
545                 550                 555                 560

Gly Gly Glu Leu Asp Lys Lys Leu Tyr Thr Thr Glu His Pro Ala Trp
            565                 570                 575

Lys Lys Val Ser Glu Lys Met Ala Ser Ser Gly Ile Gly Val Asp Phe
        580                 585                 590

Phe Leu Ala Ala Pro Ser Gly Gly Tyr Leu Asp Ile Ala Thr Ile Gly
    595                 600                 605

His Val Ala Ala Thr Thr Gly Gly Glu Thr Phe Tyr Tyr Pro Asn Phe
610                 615                 620

Ile Ala Pro Arg Asp Gly Ala Arg Leu Ser Met Glu Ile Thr His Ala
625                 630                 635                 640

Ile Thr Arg Glu Thr Gly Phe Gln Ala Leu Met Lys Val Arg Cys Ser
                645                 650                 655

Thr Gly Leu Gln Val Ala Ala Tyr His Gly Asn Phe Val Gln His Thr
            660                 665                 670

Phe Gly Ala Asp Leu Glu Ile Gly Val Ile Asp Ala Asp Lys Ala Leu
        675                 680                 685

Gly Val Ser Phe Ser His Asp Gly Lys Leu Asp Pro Lys Leu Asp Ala
    690                 695                 700

His Phe Gln Thr Ala Leu Leu Tyr Thr Thr Ala Ser Gly Gln Arg Arg
705                 710                 715                 720

Val Arg Cys Ser Asn Val Ile Ala Ser Val Ser Asp Thr Ser Lys Glu
                725                 730                 735

Ser Asn Thr Lys Glu Leu Ala Ile Arg Gln Cys Leu Lys Phe Val Asp
            740                 745                 750

Gln Asp Ala Val Val Gly Ile Phe Ala Lys Glu Ala Ser Thr Lys Leu
        755                 760                 765

Ala Thr Thr Ser Ala Asn Leu Gln Asp Val Arg Asn Trp Leu Thr Glu
770                 775                 780

Arg Thr Ile Asp Ile Met Ala Tyr Tyr Lys Lys His Ser Ala Asn Gln
785                 790                 795                 800

Phe Pro Pro Ser Gln Leu Val Met Pro Glu Arg Leu Lys Glu Phe Cys
                805                 810                 815

Met Tyr Met Leu Gly Met Leu Lys Cys Arg Ala Phe Lys Gly Gly Ile
            820                 825                 830

Glu Asn Ser Asp Arg Arg Val His Glu Leu Arg Met Val Arg Ser Met
        835                 840                 845

Gly Pro Leu Glu Leu Ser Leu Tyr Leu Tyr Pro Arg Met Ile Ala Leu
    850                 855                 860

His Asn Leu Gln Pro Glu Glu Gly Phe Ala Asp Pro Glu Thr Gly His
865                 870                 875                 880

Leu Lys Met Pro Pro Ser Val Arg Thr Ser Phe Ser Arg Val Glu Pro
                885                 890                 895

Gly Gly Val Tyr Leu Val Asp Asn Gly Gln Gln Cys Leu Leu Trp Phe
            900                 905                 910

His Ala Gln Thr Ser Pro Asn Leu Ile Thr Asp Leu Phe Gly Glu Gly
        915                 920                 925

His Asp Ser Leu Lys Gly Leu Asp Pro Tyr Thr Ser Thr Leu Pro Val
    930                 935                 940

Leu Glu Thr His Leu Ser Ala Gln Val Arg Asn Ile Ile Glu Phe Leu
945                 950                 955                 960

```
Lys Ser Met Arg Gly Ser Lys Gly Met Thr Ile Gln Leu Ala Arg Gln
            965                 970                 975

Gly Ile Asp Gly Ala Glu Tyr Glu Phe Ala Arg Met Leu Val Glu Asp
            980                 985                 990

Arg Asn Asn Glu Ala Lys Ser Tyr  Val Asp Trp Leu Val His Ile His
            995                 1000                1005

Arg Gly Val Gln Leu Glu Leu  Ser Gly Gln Arg Lys  Lys Glu Gly
            1010                1015                1020

Asp Gly  Glu Ala Thr Ala Val  Met Ala Asn Phe Ala  Gly Leu Arg
            1025                1030                1035

Pro Ala  Tyr Trp
            1040

<210> SEQ ID NO 3
<211> LENGTH: 1015
<212> TYPE: PRT
<213> ORGANISM: Aspergillus oryzae

<400> SEQUENCE: 3

Met Ala Asp Gln Ser Met Tyr Asn Thr Leu Gly Gln Gly Thr Ser Pro
1               5                   10                  15

Ala Glu Asp Pro Ser Asn Pro Asn Arg Met Ala His Gln Val Pro Pro
            20                  25                  30

Gln Ser Gln Pro Ala Ala Gly Phe Pro Pro Gly Pro Tyr Pro Pro Gln
        35                  40                  45

Pro Gly Ala Tyr Tyr Gly Asn Pro Pro Asn Gln Tyr Asp Ala Pro
    50                  55                  60

Ala Ala Ala Pro Pro Thr Gln Gln Leu Gln Ser Pro Pro Arg Gly
65                  70                  75              80

Leu Ala Pro Ser Pro Gln Leu Ala Tyr Gly Thr Glu Thr Gln Thr His
                85                  90                  95

Met Gly Ala Pro Ala Asp Pro Met Ala Gly Leu Ala Ser Gln Met Ser
            100                 105                 110

Gly Leu Gly Ile Met Gly Asp Ser Gly Ala Arg Pro Gly Lys Lys Lys
        115                 120                 125

His Arg His Ala His His Glu Ile Gly Gly Ala Thr Ala Ser Ala Pro
    130                 135                 140

Gln Gln Phe Ala Gly Met Pro Gln Ala Gly Met Gln Pro Ser Ser Gln
145                 150                 155                 160

Phe Leu Asn Thr Gly Leu Asn Gln Ala Pro Arg Pro Ile Ser Pro Ala
                165                 170                 175

Ala Gly Val Pro Pro Ala Gly Ile Val Pro Gln Pro Gly Val Pro Ala
            180                 185                 190

Pro Gly Ser Gly Ser Val Pro Thr Gln Gly Lys Ile Asp Pro Glu Gln
        195                 200                 205

Ile Pro Ser Ile Pro Gln Ser Arg Asp Ile Pro Thr Met Tyr Tyr Phe
    210                 215                 220

Asp His Ile Tyr Pro Thr Met Glu Arg His Leu Pro Pro Pro Ala Ala
225                 230                 235                 240

Val Pro Phe Val Ala His Asp Gln Gly Asn Ser Ser Pro Lys His Ala
                245                 250                 255

Arg Leu Thr Leu Asn Asn Ile Pro Thr Thr Ser Asp Phe Leu Ser Ser
            260                 265                 270

Thr Ala Leu Pro Leu Gly Met Val Leu Gln Pro Leu Ala Arg Leu Asp
        275                 280                 285
```

```
Pro Gly Glu Pro Glu Val Pro Val Leu Asp Phe Gly Glu Met Gly Pro
    290                 295                 300
Pro Arg Cys Arg Arg Cys Arg Ala Tyr Ile Asn Pro Phe Met Thr Phe
305                 310                 315                 320
Arg Ser Gly Gly Asn Lys Phe Val Cys Asn Met Cys Thr Phe Pro Asn
                325                 330                 335
Asp Val Ala Pro Glu Tyr Phe Ala Pro Leu Asp Met Ser Gly Ala Arg
            340                 345                 350
Val Asp Arg Leu Gln Arg Pro Glu Leu Met Ile Gly Thr Val Glu Phe
        355                 360                 365
Met Val Pro Lys Glu Tyr Trp Asn Lys Glu Pro Val Gly Leu Gln Arg
    370                 375                 380
Leu Phe Leu Ile Asp Val Ser Gln Glu Ser Val Asn Arg Gly Phe Leu
385                 390                 395                 400
Lys Gly Val Cys Lys Gly Ile Thr Glu Ala Leu Tyr Gly Ala Pro Asp
                405                 410                 415
Ala Ser Glu Glu Asp Ala Ala Arg Arg Val Pro Glu Gly Ser Lys
            420                 425                 430
Ile Gly Ile Val Thr Tyr Asp Arg Glu Val His Phe Tyr Asn Leu Ser
        435                 440                 445
Ala Gln Leu Asp Gln Ala Gln Met Met Val Met Thr Asp Leu Glu Glu
    450                 455                 460
Pro Phe Val Pro Leu Ser Glu Gly Leu Phe Val Asp Pro Tyr Glu Ser
465                 470                 475                 480
Lys Asp Ile Ile Thr Ser Leu Leu His Arg Ile Pro Lys Ile Phe Ser
                485                 490                 495
His Ile Lys Lys Pro Glu Pro Ala Leu Leu Pro Ala Leu Asn Ala Ala
            500                 505                 510
Met Ser Ala Leu Gln Ala Thr Gly Gly Lys Ile Phe Ala Ser Ile Cys
        515                 520                 525
Ser Leu Pro Thr Trp Gly Pro Gly Ala Leu His Met Arg Asp Asp Pro
    530                 535                 540
Lys Val His Gly Thr Asp Ala Glu Arg Lys Leu Phe Thr Thr Asp Asn
545                 550                 555                 560
Gln Ala Trp Arg Thr Thr Ala Gly Lys Met Ala Glu His Gly Ile Gly
                565                 570                 575
Val Asp Met Phe Val Ala Ala Pro Gly Gly Thr Tyr Val Asp Val Ala
            580                 585                 590
Thr Ile Gly His Val Ala Glu Val Ser Gly Gly Glu Thr Phe Phe Tyr
        595                 600                 605
Pro Asn Phe His Ala Pro Arg Asp Ile Leu Lys Leu Ser Gln Glu Phe
    610                 615                 620
Ala His Ala Val Thr Arg Glu Thr Gly Tyr Gln Ala Met Met Lys Val
625                 630                 635                 640
Arg Cys Ser Asn Gly Leu Gln Val Ser Ala Tyr His Gly Asn Phe Ile
                645                 650                 655
Gln His Ala Leu Gly Ala Asp Leu Glu Ile Gly Ser Ile Asp Ala Asp
            660                 665                 670
Lys Ala Ile Gly Val Met Phe Ser Tyr Asp Gly Lys Leu Asp Pro Lys
        675                 680                 685
Leu Asp Ala His Phe Gln Ala Ala Leu Leu Tyr Thr Thr Ala Glu Gly
    690                 695                 700
```

-continued

Gln Arg Arg Val Arg Cys Ile Asn Val Val Ala Val Asn Glu Gly
705                 710                 715                 720

Gly Leu Glu Thr Met Lys Phe Ile Asp Gln Asp Cys Val Ser Ile
            725                 730                 735

Met Ala Lys Glu Ala Ala Ala Lys Thr Val Asp Lys Ser Leu Lys Asp
        740                 745                 750

Ile Arg Ala Ser Ile Thr Glu Lys Thr Val Asp Ile Phe Ser Gly Tyr
        755                 760                 765

Arg Lys Val Phe Ser Gly Ser His Pro Gly Gln Leu Val Leu Pro
770                 775                 780

Glu Asn Leu Lys Glu Phe Ser Met Tyr Met Leu Ala Leu Ile Lys Ser
785                 790                 795                 800

Arg Ala Phe Lys Gly Gly Gln Glu Ala Ser Asp Arg Arg Ile His Asp
            805                 810                 815

Met Arg Met Leu Arg Ser Ile Gly Ala Thr Glu Leu Ala Leu Tyr Leu
        820                 825                 830

Tyr Pro Arg Val Ile Pro Ile His Asn Met Gln Pro Glu Asp Gly Phe
        835                 840                 845

Pro Asn Glu Gln Gly Gln Leu Gln Val Pro Pro Ser Leu Arg Ala Ser
850                 855                 860

Phe Ser Lys Ile Glu Glu Gly Gly Ala Tyr Leu Val Asp Asn Gly Gln
865                 870                 875                 880

Ile Cys Leu Leu Trp Leu His Ser Arg Val Ser Pro Asn Leu Leu Glu
            885                 890                 895

Asp Leu Leu Gly Pro Gly Gln Ser Ser Leu Gln Gly Leu Asn Pro Gln
        900                 905                 910

Thr Ser Ser Leu Pro Val Leu Glu Thr His Leu Asn Ala Gln Val Arg
        915                 920                 925

Asn Leu Leu Gln Tyr Phe Ser Thr Met Arg Gly Ser Lys Ser Val Ala
930                 935                 940

Ile Gln Leu Ala Arg Gln Gly Leu Asp Gly Ala Glu Tyr Glu Phe Ala
945                 950                 955                 960

Arg Leu Leu Val Glu Asp Arg Asn Asn Glu Ala Gln Ser Tyr Val Asp
            965                 970                 975

Trp Leu Val His Ile His Arg Gln Ile Asn Leu Glu Leu Ala Gly His
        980                 985                 990

Arg Lys Arg Glu Asp Thr Ser Ala  Glu Gly Ser Leu Thr  Ser Leu Ala
        995                 1000                1005

Gly Leu  Arg Ala Pro Tyr Trp
    1010                1015

<210> SEQ ID NO 4
<211> LENGTH: 1009
<212> TYPE: PRT
<213> ORGANISM: Aspergillus niger

<400> SEQUENCE: 4

Met Ala Asp Pro Asn Met Tyr His Thr Tyr Gly Gln Ala Pro Val Pro
1                   5                   10                  15

Gly Glu Asn Pro Ser Asp Pro Asn Gln Met Ala Tyr Gln Val Pro Pro
            20                  25                  30

Gln Gly Tyr Pro Ala Ala Gly Ile Pro Pro Gly Pro Ser Pro Pro Gln
        35                  40                  45

Pro Gly Ala Ala Tyr Gly Val Pro Ala Pro Asn Gln Gln Trp Pro Ala
50                  55                  60

```
Tyr Gly Ser Pro Pro Ala Gln Gln Pro Leu Gln Gln Pro Ser
 65                  70                  75                  80

Gln Phe Ala His Gln Ala Asp Pro Gln Ala Met Gly Ala Pro Val
                 85                  90                  95

Asp Pro Gly Met Ala Gly Leu Ala Ser Gln Met Ser Gly Leu Gly Ile
            100                 105                 110

Met Gly Gly Glu Gly Gly Ala Ala Arg Ser Ser Lys Lys His Arg
        115                 120                 125

His Ala His His Glu Ile Ala Gly Ala Ser Ala Ser Val Ala Gln Pro
        130                 135                 140

Phe Ala Ala Ala Pro Gln Asp Pro Met Gln Pro Thr Ser Gln Phe Leu
145                 150                 155                 160

Asn Thr Gly Leu Asn Gln Ala Pro Arg Pro Ile Ser Pro Ala Ala Ser
                165                 170                 175

Ile Pro Ala Pro Val Asn Pro Ala Phe Gly Gly Ala Gly Ala Val
            180                 185                 190

Pro Thr Gln Gly Lys Val Asp Pro Glu Gln Ile Pro Ser Ile Pro Arg
        195                 200                 205

Ser Arg Asp Leu Pro Ala Gln Tyr Tyr Phe Asn His Val Tyr Pro Thr
210                 215                 220

Met Glu Arg His Leu Pro Pro Ala Val Pro Phe Val Ala His
225                 230                 235                 240

Asp Gln Gly Asn Ser Ser Pro Lys Tyr Ala Arg Leu Thr Leu Asn Asn
                245                 250                 255

Ile Pro Ser Thr Ser Asp Phe Leu Ser Ser Thr Gly Leu Pro Leu Gly
            260                 265                 270

Met Val Leu Gln Pro Leu Ala Arg Leu Asp Gly Glu Gln Pro Ile Pro
        275                 280                 285

Val Leu Asp Phe Gly Asp Ala Gly Pro Pro Arg Cys Arg Cys Arg
290                 295                 300

Ala Tyr Ile Asn Pro Phe Met Ser Phe Arg Ser Gly Gly Asn Lys Phe
305                 310                 315                 320

Val Cys Asn Met Cys Thr Phe Pro Asn Asp Val Pro Pro Glu Tyr Phe
                325                 330                 335

Ala Pro Leu Asp Pro Ser Gly Ser Arg Ile Asp Arg Met Gln Arg Pro
            340                 345                 350

Glu Leu Met Met Gly Thr Val Glu Phe Leu Val Pro Lys Asp Tyr Trp
        355                 360                 365

Asn Lys Glu Pro Val Gly Leu Gln Trp Leu Leu Leu Ile Asp Val Ser
        370                 375                 380

Gln Glu Ser Val Asn Lys Gly Phe Leu Lys Gly Val Cys Lys Gly Ile
385                 390                 395                 400

Met Glu Ala Leu Tyr Ser Glu Glu Thr Glu Asn Pro Glu Asp Glu Ala
                405                 410                 415

Pro Ala Arg Arg Ile Pro Glu Gly Ala Lys Ile Gly Ile Val Thr Tyr
            420                 425                 430

Asp Lys Glu Val His Phe Tyr Asn Leu Ser Ala Gln Leu Asp Gln Ala
        435                 440                 445

Gln Met Met Val Met Thr Asp Leu Glu Glu Pro Phe Val Pro Leu Ser
        450                 455                 460

Glu Gly Leu Phe Val Asp Pro Tyr Glu Ser Lys Asp Val Ile Thr Ser
465                 470                 475                 480
```

```
Leu Leu Gln Arg Ile Pro Ser Ile Phe Ser His Val Lys Asn Pro Gln
                485                 490                 495

Pro Ala Leu Leu Pro Ala Leu Asn Ala Ala Leu Ser Ala Leu Arg Pro
            500                 505                 510

Thr Gly Gly Lys Ile Val Gly Thr Ile Ala Ser Leu Pro Thr Trp Gly
        515                 520                 525

Pro Gly Ala Leu Ser Leu Arg Asp Pro Lys Val His Gly Thr Asp
    530                 535                 540

Ala Glu Arg Lys Leu Phe Thr Thr Glu His Ala Gly Trp Arg Glu Thr
545                 550                 555                 560

Ala Gly His Leu Ala Glu Ala Gly Ile Gly Leu Asp Met Phe Ile Ala
                565                 570                 575

Ala Pro Ser Gly Thr Tyr Met Asp Val Ala Thr Ile Gly His Ile Pro
            580                 585                 590

Glu Val Thr Gly Gly Glu Thr Phe Phe Tyr Pro Asn Phe His Ala Pro
        595                 600                 605

Arg Asp Ile Arg Lys Leu Ser Lys Glu Leu Ala His Ala Ile Thr Arg
    610                 615                 620

Glu Thr Gly Tyr Gln Ala Leu Met Lys Val Arg Cys Ser Asn Gly Leu
625                 630                 635                 640

Gln Val Ser Gly Tyr His Gly Asn Phe Val Gln His Thr Phe Gly Ala
                645                 650                 655

Asp Leu Glu Ile Gly Ala Ile Asp Ala Asp Lys Ala Ile Gly Val Val
            660                 665                 670

Phe Ser Tyr Asp Gly Lys Leu Asp Pro Lys Leu Asp Ala His Phe Gln
        675                 680                 685

Ala Ala Leu Leu Tyr Thr Ser Ala Asn Gly Gln Arg Arg Val Arg Cys
    690                 695                 700

Ile Asn Thr Val Ala Ala Val Asn Glu Gly Gly Met Glu Thr Met Lys
705                 710                 715                 720

Phe Val Asp Gln Asp Ala Val Val Ala Met Val Ala Lys Asp Ala Ala
                725                 730                 735

Ser Lys Thr Leu Asp Lys Ser Leu Lys Asp Ile Arg Ala Gly Val Ser
            740                 745                 750

Glu Lys Thr Val Asp Ile Phe Ser Gly Tyr Arg Lys Ile Phe Ser Gly
        755                 760                 765

Ser His Pro Pro Gly Gln Leu Val Leu Pro Glu Asn Leu Lys Glu Phe
    770                 775                 780

Ser Met Tyr Met Leu Ser Leu Ile Lys Ser Arg Ala Ile Lys Gly Gly
785                 790                 795                 800

Gln Glu Ala Ser Asp Arg Arg Ile His Asp Met Arg Met Leu Arg Ser
                805                 810                 815

Ile Gly Cys Thr Glu Leu Ser Leu Tyr Leu Tyr Pro Arg Ile Ile Pro
            820                 825                 830

Ile His Asn Met Gln Pro Thr Asp Gly Phe Pro Asn Glu Gln Gly Gln
        835                 840                 845

Leu Gln Val Pro Pro Ser Leu Arg Ala Ser Phe Ser Lys Ile Glu Glu
    850                 855                 860

Gly Gly Ala Tyr Leu Val Asp Asn Gly Gln Gln Cys Leu Leu Trp Leu
865                 870                 875                 880

His Ser His Val Ser Pro Asn Leu Leu Glu Asp Leu Phe Gly Glu Gly
                885                 890                 895

Gln Thr Ser Leu Gln Gly Leu Ser Pro Gln Ile Ser Thr Ile Pro Val
```

```
                900             905             910
Leu Glu Thr His Leu Asn Ala Gln Val Arg Asn Leu Leu Gln Tyr Phe
            915             920             925

Ser Thr Ile Arg Gly Ser Lys Ala Val Thr Ile Gln Leu Ala Arg Gln
        930             935             940

Gly Leu Asp Gly Ala Glu Tyr Glu Phe Ala Arg Met Leu Val Glu Asp
945             950             955             960

Arg Asn Asn Glu Ala Gln Ser Ser Val Asp Trp Leu Val His Ile His
            965             970             975

Arg Gln Ile Asn Leu Glu Leu Ala Gly His Arg Lys Arg Glu Asp Thr
        980             985             990

Ala Gly Glu Gly Gly Leu Thr Ser  Leu Ala Gly Leu Arg  Ala Pro Tyr
            995             1000            1005

Trp

<210> SEQ ID NO 5
<211> LENGTH: 999
<212> TYPE: PRT
<213> ORGANISM: Penicillium funiculosum

<400> SEQUENCE: 5

Met Ala Asp Tyr Ser Thr Tyr His Ser Ser Gly Tyr Ala Gly Ala Pro
1               5               10              15

Gly Glu Asp Pro Asn Arg Gln Gln Pro Ala Val Pro Ala Pro Tyr His
            20              25              30

Ser Pro Asn Ala Pro Pro Gly Gln Ala Ile Gln Pro Gly Ile Thr
        35              40              45

Pro Tyr Gly Ala Ala Gln Pro Pro Gln Phe Pro Gly Gln Pro Gly Val
50              55              60

Gly Tyr Gly Val Ala Pro Val Pro Ser Pro Pro Gln Ala Leu Gly Gly
65              70              75              80

Pro Asp Val Gly Asp Leu Ala Thr Arg Ile Gly Leu Gly Ile Ile
            85              90              95

Ser Asp Ala Gly Thr Arg Ser His Lys Lys His Arg His Ala Tyr
        100             105             110

His Asp Ile Gly Gly Pro Asn Ala Gln Gly Leu Asn Thr Phe Pro Ser
    115             120             125

Gln Thr Asn Leu Gln Ser Gln Phe Leu Asn Thr Gly Leu Asn Gln Pro
    130             135             140

Glu Gln Gln Pro Ala Ala Pro Ala Ala Phe Pro Gly Ala Pro Val Gly
145             150             155             160

Gln Val Pro Ala Asn Val Ala Pro Gly Ala Ala Pro Glu Val Gly Gly
            165             170             175

Val Gly Ser Val Pro Thr Gln Gly Lys Ile Asp Pro Glu Gln Ile Pro
        180             185             190

Ser Val Pro Arg Ser Arg Asp Leu Pro Ala Gln Tyr Tyr Phe Asn Asn
    195             200             205

Val Tyr Pro Thr Met Glu Arg His Val Pro Pro Ala Ser Ile Pro
    210             215             220

Phe Ile Ala His Asp Gly Asn Ser Ser Pro Lys Val Ala Arg Leu
225             230             235             240

Thr Leu Asn Asn Ile Pro Ser Ser Ser Asp Phe Leu Gln Ser Thr Gly
            245             250             255

Leu Pro Leu Gly Met Ile Leu Gln Pro Leu Ala Lys Leu Asp Ala Gly
```

```
                260                 265                 270
Glu Gln Pro Val Pro Val Ile Asp Phe Gly Asp Ile Gly Pro Pro Arg
            275                 280                 285
Cys Arg Arg Cys Arg Thr Tyr Ile Asn Pro Phe Met Thr Phe Arg Ser
            290                 295                 300
Gly Gly Asn Lys Phe Val Cys Asn Met Cys Thr Phe Pro Asn Asp Val
305                 310                 315                 320
Pro Pro Glu Tyr Phe Ala Pro Val Asp Pro Ser Gly Val Arg Val Asp
                325                 330                 335
Arg Leu Gln Arg Pro Glu Leu Met Leu Gly Thr Val Glu Phe Thr Val
            340                 345                 350
Pro Lys Glu Tyr Trp Val Lys Glu Pro Ala Gly Leu His Gln Leu Phe
            355                 360                 365
Leu Ile Asp Val Ser Gln Glu Ser Val Asn Arg Gly Phe Leu Lys Gly
        370                 375                 380
Val Cys Asp Gly Ile Ile Asn Ala Leu Tyr Gly Glu Glu Pro Val
385                 390                 395                 400
Glu Gly Ala Glu Pro Glu Thr Arg Lys Val Pro Glu Gly Ser Lys Ile
                405                 410                 415
Gly Ile Val Thr Phe Asp Arg Glu Ile His Phe Tyr Asn Leu Leu Pro
                420                 425                 430
Arg Leu Asp Lys Ala Gln Met Met Val Met Thr Asp Leu Glu Glu Pro
            435                 440                 445
Phe Val Pro Leu Ser Glu Gly Leu Phe Val Asp Pro Tyr Glu Ser Lys
        450                 455                 460
Asp Val Ile Thr Ser Leu Leu Glu Gln Leu Pro Ser Leu Phe Ala Arg
465                 470                 475                 480
Val Lys Ser Pro Glu Ser Thr Leu Leu Pro Thr Ile Lys Ala Ala Ile
                485                 490                 495
Ser Ala Leu Gln Ala Thr Gly Gly Lys Ile Ile Cys Cys Leu Thr Ser
            500                 505                 510
Leu Pro Thr Tyr Gly Pro Gly Lys Leu Val Met Lys Asp Lys Ser Gln
        515                 520                 525
Ala Pro Asp Gly Glu Asn Lys Leu Phe Ala Ile Asp Asn Pro Asp Tyr
        530                 535                 540
Lys Ala Ala Ala Thr Lys Leu Thr Glu Ala Gly Val Gly Ile Asp Phe
545                 550                 555                 560
Phe Val Ala Ala Pro Gly Gly Ser Phe Met Asp Leu Thr Thr Ile Gly
            565                 570                 575
Tyr Thr Ala Ala Ile Ser Gly Gly Glu Cys Phe Phe Tyr Pro Asn Phe
            580                 585                 590
His Ser Pro Arg Asp Ser Leu Lys Leu Ala Gln Glu Ile Ser His Thr
        595                 600                 605
Val Thr Arg Glu Thr Gly Tyr Gln Ala Leu Met Lys Val Arg Cys Ser
        610                 615                 620
Asn Gly Leu Gln Val Ser Ala Tyr Tyr Gly Asn Phe Leu Gln His Thr
625                 630                 635                 640
Phe Gly Ala Asp Leu Glu Ile Gly Thr Ile Asp Ala Asp Lys Ala Leu
                645                 650                 655
Gly Val Leu Phe Ser Tyr Asp Gly Lys Leu Asp Pro Lys Leu Asp Ala
                660                 665                 670
His Phe Gln Ala Ala Leu Leu Tyr Thr Ala Ala Asn Gly Gln Arg Arg
            675                 680                 685
```

```
Val Arg Cys Ile Asn Ile Val Ala Gly Val Asn Glu Gly Gly Ile Glu
        690                 695                 700

Thr Met Lys Cys Ile Asp Gln Asp Ala Val Val Ala Ile Ile Ala Lys
705                 710                 715                 720

Glu Ala Ala Ser Lys Ala Gly Asp Lys Thr Leu Lys Asp Ile Arg Ala
                725                 730                 735

Ser Ile Thr Glu Lys Thr Val Asp Ile Phe Ser Gly Tyr Arg Lys Asn
            740                 745                 750

Phe Ser Gly Ser His Pro Pro Gly Gln Leu Val Leu Pro Glu Asn Leu
        755                 760                 765

Lys Glu Phe Ser Met Tyr Met Leu Gly Leu Leu Lys Ser Arg Ala Phe
770                 775                 780

Lys Gly Gly Ser Glu Thr Ala Asp Arg Arg Val His Asp Leu Arg Met
785                 790                 795                 800

Leu Arg Ser Ile Gly Cys Leu Glu Leu Ser Leu Tyr Leu Tyr Pro Arg
                805                 810                 815

Ile Ile Pro Ile His Asn Met Ser Ala Glu Asp Gly Phe Ala Asn Glu
            820                 825                 830

Gln Gly Gln Leu Gln Val Pro Pro Ala Leu Arg Ala Ser Phe Ser Arg
        835                 840                 845

Val Glu Glu Gly Gly Ala Tyr Leu Ile Asp Asn Gly Gln Gly Ile Leu
850                 855                 860

Leu Trp Ile His Ser Phe Val Ser Pro Asn Leu Leu Glu Asp Leu Phe
865                 870                 875                 880

Gly Pro Gly Ile Thr Ser Leu Gln Ala Leu Asp Pro Asn Thr Ser Ser
                885                 890                 895

Leu Pro Val Leu Glu Thr His Leu Asn Ala Gln Val Arg Asn Leu Leu
            900                 905                 910

Gln Tyr Leu Ser Thr Val Arg Gly Ser Lys Ala Val Thr Ile Gln Leu
        915                 920                 925

Ala Arg Gln Gly Ile Asp Gly Ala Glu Tyr Glu Phe Ala Arg Ser Leu
    930                 935                 940

Val Glu Asp Arg Asn Asn Glu Ala Gln Ser Tyr Val Asp Trp Leu Val
945                 950                 955                 960

His Ile His Arg Gln Ile Asn Leu Glu Leu Ala Gly His Arg Lys Lys
                965                 970                 975

Glu Asp Ser Ala Thr Ser Ser Gly Glu Gly Ala Leu Ser Ser Leu Ala
            980                 985                 990

Gly Ile Arg Ala Pro Tyr Trp
        995

<210> SEQ ID NO 6
<211> LENGTH: 1011
<212> TYPE: PRT
<213> ORGANISM: Penicillium chrysogenum

<400> SEQUENCE: 6

Met Ala Asp Ser Ser Met Tyr Asn Thr Met Gly Gln Gly Ser Ser Glu
1               5                   10                  15

Asp Pro Ser Asn Pro Gln Tyr Met Ala Gln Val Pro Gln Gln Tyr
                20                  25                  30

Pro Ala Gly Tyr Pro Pro Thr Ala Ala Pro Leu Gln Pro Gly Ala Pro
            35                  40                  45

Tyr Ala Asn Pro Ala Pro Asn Gln Trp Pro Ala Tyr Gly Ser Pro Gln
```

-continued

```
                50                  55                  60
Gln Pro Gly Met Ala Ser Pro Gly Ile Ala Tyr Asn Ala Pro Gln Gln
 65                  70                  75                  80

Pro Met Gly Ala Ala Val Asp Pro Gly Met Ala Gly Leu Ala Ser Gln
                 85                  90                  95

Met Gly Gly Leu Asp Ile Ala Ala Asp Ala Gly Ala Arg Thr His Arg
                100                 105                 110

Lys Lys His Arg His Ala His His Asp Ile Gly Gly Ala Ala Pro
            115                 120                 125

Pro Ala Gln Gly Phe Asn Thr Gly Met Asp Gln Gly Gly Leu Gln Gln
            130                 135                 140

Pro Gln Pro Gln Gln Ser Gln Phe Leu Asn Thr Gly Leu Asn Gln
145                 150                 155                 160

His Ala Asp Arg Pro Val Ser Pro Ala Val Gly Leu Val Ser Gly Gln
                165                 170                 175

Ser Val Ala Ala Ile Pro Gly Ile Gln Ser Gly Ala Gly Ser Val Pro
                180                 185                 190

Thr Ser Gly Arg Ile Asp Pro Glu His Ile Pro Ser Ile Pro Arg Ser
                195                 200                 205

Arg Asp Leu Pro Ala Gln Tyr Tyr Phe Asn His Val Tyr Pro Thr Met
                210                 215                 220

Asp Gln His Leu Pro Pro Ala Ala Ile Pro Phe Val Ala Gln Asp
225                 230                 235                 240

Gln Gly Asn Ser Ser Pro Lys Tyr Ala Arg Leu Thr Leu Asn Asn Ile
                245                 250                 255

Pro Ser Ala Ser Asp Phe Leu Thr Ser Thr Gly Leu Pro Leu Gly Met
                260                 265                 270

Ile Leu Gln Pro Leu Ala Pro Leu Asp Pro Gly Glu Gln Pro Ile Pro
                275                 280                 285

Val Leu Asp Phe Gly Asp Val Gly Pro Pro Arg Cys Arg Arg Cys Arg
                290                 295                 300

Thr Tyr Ile Asn Pro Phe Met Ser Phe Arg Ser Gly Gly Ser Lys Phe
305                 310                 315                 320

Val Cys Asn Met Cys Thr Phe Pro Asn Asp Thr Pro Glu Tyr Phe
                325                 330                 335

Ala Pro Leu Asp Pro Ser Gly Ala Arg Val Asp Arg Met Gln Arg Pro
                340                 345                 350

Glu Leu Leu Met Gly Thr Val Glu Phe Thr Val Pro Lys Glu Tyr Trp
                355                 360                 365

Asn Lys Glu Pro Val Gly Leu Gln Thr Leu Phe Leu Ile Asp Val Ser
370                 375                 380

Arg Glu Ser Val His Arg Gly Phe Leu Lys Gly Val Cys Ala Gly Ile
385                 390                 395                 400

Lys Asp Ala Leu Tyr Gly Asp Asp Lys Ala Ser Glu Gly Thr Glu
                405                 410                 415

Gly Asp Gly Ser Ser Arg Lys Leu Pro Val Gly Ala Lys Val Gly Ile
                420                 425                 430

Val Thr Tyr Asp Lys Glu Val His Phe Tyr Asn Leu Ala Ala Ala Leu
                435                 440                 445

Asp Gln Ala Gln Met Met Val Met Thr Asp Leu Asp Glu Pro Phe Val
                450                 455                 460

Pro Leu Ser Glu Gly Leu Phe Val Asp Pro Tyr Glu Ser Lys Ser Val
465                 470                 475                 480
```

```
Ile Thr Ser Leu Leu Ser Arg Ile Pro Lys Ile Phe Ser Ser Ile Lys
            485                 490                 495

Asn Pro Glu Ser Ala Leu Leu Pro Thr Leu Asn Ser Ala Leu Ser Ala
            500                 505                 510

Leu Gln Ala Thr Gly Gly Lys Ile Val Cys Ala Val Ala Ser Leu Pro
            515                 520                 525

Thr Cys Gly Pro Gly His Leu Ala Ile Arg Glu Asp Pro Lys Val His
            530                 535                 540

Gly Thr Asp Ala Glu Arg Lys Leu Phe Thr Thr Glu Asn Pro Ala Trp
545                 550                 555                 560

Lys Lys Thr Ala Ser Lys Leu Ala Glu Ala Gly Val Gly Leu Asp Leu
            565                 570                 575

Phe Met Ala Ala Pro Gly Gly Thr Tyr Leu Asp Val Ala Thr Ile Gly
            580                 585                 590

His Val Ser Ser Leu Thr Gly Gly Thr Phe Phe Tyr Pro Asn Phe
            595                 600                 605

His Ala Pro Arg Asp Leu Leu Lys Leu Arg Lys Glu Ile Ala His Ala
            610                 615                 620

Val Thr Arg Glu Thr Gly Tyr Gln Thr Leu Met Lys Val Arg Cys Ser
625                 630                 635                 640

Asn Gly Leu Gln Val Ser Ala Tyr His Gly Asn Phe Val Gln His Thr
            645                 650                 655

Leu Gly Ala Asp Leu Glu Ile Ala Gly Val Asp Ala Asp Lys Ala Val
            660                 665                 670

Gly Val Leu Phe Ser Tyr Asp Gly Lys Leu Asp Pro Lys Leu Asp Ala
            675                 680                 685

His Phe Gln Ala Ala Leu Leu Tyr Thr Ser Ala Asp Gly Gln Arg Arg
            690                 695                 700

Val Arg Cys Ile Asn Val Val Ala Ala Val Asn Glu Gly Gly Leu Glu
705                 710                 715                 720

Thr Met Lys Phe Val Asp Gln Asp Ala Val Val Ser Val Ile Ala Lys
            725                 730                 735

Glu Ala Ala Ser Lys Thr Leu Asp Lys Asn Leu Lys Asp Ile Arg Ala
            740                 745                 750

Ser Ile Ser Glu Lys Thr Val Asp Ile Phe Ser Gly Tyr Arg Lys Ile
            755                 760                 765

Phe Ser Gly Ser His Pro Pro Gly Gln Leu Val Leu Pro Glu Asn Leu
            770                 775                 780

Lys Glu Phe Ser Met Tyr Met Leu Ser Leu Val Lys Ser Arg Ala Phe
785                 790                 795                 800

Lys Ala Gly Pro Glu Ser Ser Asp Arg Arg Ile His Asp Met Arg Leu
            805                 810                 815

Ile Arg Ser Met Gly Cys Thr Glu Met Ala Leu Tyr Leu Tyr Pro Arg
            820                 825                 830

Ile Ile Pro Val His Asn Met Gln Pro Glu Asp Gly Phe Ala Asn Glu
            835                 840                 845

His Gly Gln Leu Gln Ile Pro Pro Thr Met Arg Ala Ser Tyr Ser Arg
            850                 855                 860

Ile Glu Asp Gly Gly Val Tyr Ile Val Asp Asn Gly Gln Ala Ile Leu
865                 870                 875                 880

Leu Trp Ile His Ala Gln Val Ser Pro Asn Leu Leu Glu Asp Leu Phe
            885                 890                 895
```

-continued

```
Gly Pro Gly His Asn Ser Leu Gln Gly Leu Asn Pro Asn Thr Ser Ser
                900                 905                 910

Leu Pro Val Leu Glu Thr His Leu Asn Ala Gln Val Arg Asn Leu Leu
            915                 920                 925

Gln Tyr Leu Ser Thr Val Arg Gly Ser Lys Ser Val Thr Ile Gln Leu
        930                 935                 940

Ala Arg Gln Gly Leu Asp Gly Ala Glu Tyr Glu Phe Ala Arg Leu Leu
945                 950                 955                 960

Leu Glu Asp Arg Asn Asn Glu Ala Gln Ser Tyr Val Asp Trp Leu Val
                965                 970                 975

His Ile His Arg Gln Ile Asn Leu Glu Leu Ala Gly His Arg Lys Lys
            980                 985                 990

Glu Glu Gly Gly Glu Gly Ala Leu Ala Ser Leu Ser Ala Met Arg Thr
        995                 1000                1005

Pro Tyr Trp
    1010

<210> SEQ ID NO 7
<211> LENGTH: 1052
<212> TYPE: PRT
<213> ORGANISM: Neurospora crassa

<400> SEQUENCE: 7

Met Ala Asp Tyr Thr Met Tyr His Ala Leu Gly Gln Gly Glu Thr Leu
1               5                   10                  15

Asp Pro Asn Asp Pro Asn Arg Thr Thr Gln Pro Ala Pro Pro Gln Phe
            20                  25                  30

Gln Pro Pro Val Ala Pro Asn Pro Tyr His Pro Gly Ala Glu Tyr Asn
        35                  40                  45

Ala Pro Gly Gln Gln Gln Gln Gln Gln Gln Tyr Gly Gln Gln Tyr
    50                  55                  60

Gly Gln Gln Tyr Gly Gln Gln Tyr Gly Gln Gln Tyr Gly Gln Glu
65                  70                  75                  80

Tyr Gly His Gln Gln Gln Gln Gln Gln Gln Tyr Gly Ala Pro
                85                  90                  95

Ser Pro Tyr Gly Ala Pro Pro Ala His Ser Pro Val Ser Pro Met Asp
            100                 105                 110

Asp Val Gly Leu Ala Ala Gln Met Gly Gly Met Ser Leu Gly Ala Gly
        115                 120                 125

Ala Gly Ala Ala Asp His His Gly Arg Lys Lys Lys Asp Arg His
    130                 135                 140

Ala Phe His Thr Val Glu Ala Pro Ala Gly Ser Ser Gln Pro Phe Asn
145                 150                 155                 160

Gly Met Pro Pro Ala Gly Ile Pro Ala Thr Gln Phe Leu Asn Ala Asp
                165                 170                 175

Pro Ser Leu Ala Gly Arg Ile Pro Gly Pro His Gly Gln Phe Pro
            180                 185                 190

Met Pro Ala Ser Pro Ala Phe Gly Pro Val Pro Thr Ser Ala Ala Asp
        195                 200                 205

Phe Ala Ala Arg Asp Ala Thr Gln Gly Val Gly Ser Gly Val Phe Ala
    210                 215                 220

Ala Gly Gly Pro Gln Gly Gly Lys Pro Ser Pro Asp Asp Thr Pro Ser
225                 230                 235                 240

Val Pro Leu Ser Arg Asp Ala Val Gln Pro Tyr Phe His Thr Asn Val
                245                 250                 255
```

```
Tyr Pro Thr Phe Glu Arg Leu Val Pro Pro Ala Val Thr Ser Phe
            260                 265                 270

Val Ala Leu Asp Gln Gly Asn Ser Ser Pro Lys Phe Ala Arg Leu Thr
            275                 280                 285

Met Thr Asn Leu Pro Ala Ser Ala Glu Gly Leu Lys Ser Thr Gly Leu
290                 295                 300

Pro Leu Gly Leu Leu Leu Gln Pro Leu Ala Glu Thr Gln Pro Gly Glu
305                 310                 315                 320

Leu Pro Ile Pro Val Leu Asp Phe Gly Glu Gln Gly Pro Pro Arg Cys
                325                 330                 335

His Arg Cys Arg Ala Tyr Met Asn Pro Phe Met Phe Lys Ala Gly
            340                 345                 350

Gly Asn Lys Phe Val Cys Asn Leu Cys Thr Tyr Ala Asn Asp Thr Pro
            355                 360                 365

Pro Glu Tyr Phe Cys Ala Leu Ser Pro Gln Gly Val Arg Val Asp Arg
    370                 375                 380

Asp Gln Arg Pro Glu Leu Thr Arg Gly Thr Val Glu Phe Val Val Pro
385                 390                 395                 400

Lys Glu Tyr Trp Thr Lys Glu Pro Val Gly Met Arg Tyr Leu Phe Val
                405                 410                 415

Ile Asp Val Thr Gln Glu Ser Tyr Asn Lys Gly Phe Leu Glu Ser Phe
            420                 425                 430

Cys Glu Gly Ile Leu Ser Ala Leu Tyr Gly Gly Ser Glu Glu Gly Glu
            435                 440                 445

Asp Gln Asp Glu Thr Gly Glu Pro Lys Arg Lys Ile Pro Ala Gly Ala
450                 455                 460

Lys Val Gly Phe Val Thr Phe Asp Gln Glu Ile His Phe Tyr Asn Val
465                 470                 475                 480

Ser Pro Ala Leu Glu Gln Ala Gln Met Ile Val Met Pro Asp Ile Glu
            485                 490                 495

Asp Pro Phe Leu Pro Leu Ser Asp Gly Leu Phe Val Asp Pro Tyr Glu
            500                 505                 510

Ser Lys Ala Val Ile Ser Ser Leu Leu Thr Arg Leu Pro Gln Met Phe
            515                 520                 525

Ser Asn Ile Lys Asn Pro Glu Pro Ala Leu Leu Ser Ala Leu Asn Ser
530                 535                 540

Ala Val Ala Ala Leu Glu Lys Thr Gly Gly Lys Val Phe Cys Ser Leu
545                 550                 555                 560

Ala Ala Leu Pro Thr Trp Gly Pro Gly Arg Leu Phe Met Arg Asp Asp
                565                 570                 575

Gly Lys His Pro Gly Glu Pro Asp Lys Lys Leu Phe Thr Thr Glu
            580                 585                 590

His Pro Gly Trp Arg Lys Leu Ala Glu Lys Met Val Ser Leu Gly Val
            595                 600                 605

Gly Ala Asp Phe Phe Met Ala Ser Pro Ser Gly Gly Tyr Leu Asp Ile
            610                 615                 620

Ala Thr Ile Gly His Val Ser Ser Thr Thr Gly Gly Glu Thr Phe Phe
625                 630                 635                 640

Tyr Pro Asn Phe Val Val Gln Arg Asp Ser Thr Lys Leu Ser Leu Glu
                645                 650                 655

Ile His His Ala Val Arg Arg Glu Thr Gly Tyr Ala Ala Leu Met Lys
            660                 665                 670
```

Val Arg Cys Ser Asn Gly Leu Gln Val Asn Ala Tyr His Gly Asn Phe
            675                 680                 685

Ile Gln His Thr Phe Gly Ala Asp Leu Glu Ile Gly Val Ile Asp Ala
690                 695                 700

Asp Lys Ala Leu Ala Val Thr Phe Gly Tyr Asp Gly Lys Leu Asp Ser
705                 710                 715                 720

Lys Leu Asp Ala His Phe Gln Ala Ala Leu Leu Tyr Thr Thr Ala Ser
            725                 730                 735

Gly Gln Arg Arg Val Arg Cys Ile Asn Val Ile Ala Gly Val Ser Asp
            740                 745                 750

Leu Ala Arg Asp Cys Met Lys Tyr Ile Asp Gln Asp Ala Ile Val Ser
            755                 760                 765

Ile Leu Ala Lys Glu Ala Ser Thr Lys Leu Ser Thr Thr Ser Ala Asn
            770                 775                 780

Leu Lys Glu Val Arg Ser Ser Leu Thr Glu Lys Thr Ile Asp Ile Leu
785                 790                 795                 800

Ala Leu Tyr Arg Lys Asn His Leu Ala Val Pro His Pro Pro Gln Gln
            805                 810                 815

Leu Val Met Pro Glu Arg Leu Lys Glu Phe Thr Met Tyr Val Leu Gly
            820                 825                 830

Met Leu Lys Cys Arg Ala Phe Lys Gly Gly Asn Glu Thr Thr Asp Arg
            835                 840                 845

Arg Val His Asp Met Arg Leu Ile Arg Ser Met Gly Ala Arg Glu Leu
            850                 855                 860

Ser Leu Tyr Leu Tyr Pro Arg Ile Ile Pro Leu His Ser Leu Gln Pro
865                 870                 875                 880

Glu Asp Gly Tyr Pro Asp Ala Thr Thr Gly His Leu Arg Met Pro Ser
            885                 890                 895

Thr Met Arg Ala Ser Phe Ala Arg Val Glu Pro Gly Gly Val Tyr Leu
            900                 905                 910

Val Asp Asn Gly Gln Val Cys Leu Leu Trp Met His Ala Gln Thr Ala
            915                 920                 925

Pro Ala Leu Ile Gln Asp Leu Phe Gly Glu Asp Lys Thr Thr Leu Gln
930                 935                 940

Ser Leu Asp Pro Tyr Thr Ser Thr Ile Pro Val Leu Glu Thr His Leu
945                 950                 955                 960

Asn Ala Gln Thr Arg Asn Ile Ile Glu Tyr Met Arg Thr Val Arg Gly
            965                 970                 975

Ser Lys Gly Leu Thr Ile Gln Leu Ala Arg Gln Gly Ile Asp Gly Ala
            980                 985                 990

Glu Phe Glu Phe Ala Arg Met Leu Val Glu Asp Arg Asn Asn Glu Ala
            995                 1000                1005

Gln Ser Tyr Val Asp Trp Leu Val His Val His Lys Gly Val Gln
            1010                1015                1020

Leu Glu Leu Ala Gly Gln Arg Lys Arg Glu Asp Gly Glu Ser His
            1025                1030                1035

Ser Ala Leu Gly Ser Phe Thr Gly Leu Arg Pro Ala Tyr Trp
            1040                1045                1050

<210> SEQ ID NO 8
<211> LENGTH: 1038
<212> TYPE: PRT
<213> ORGANISM: Fusarium oxysporum

<400> SEQUENCE: 8

```
Met Ala Asp Tyr Ala Gln Tyr His Ala Leu Gly Gln Gly Glu Val Ile
1               5                   10                  15

Asp Pro Asn Asp Pro Asn Arg Thr Ser Gln Pro Ser Ala Gln Gln Phe
            20                  25                  30

Gln Pro Pro Ile Ala Pro Ser Pro Tyr Gln Gln Gln Ala Ser Pro Tyr
            35                  40                  45

Gly Ala Pro Gln Tyr Leu Gly Gly Gln Gln Ala Pro Pro Pro Met Thr
50                  55                  60

Gly Ser Pro Ala Pro Ala Pro Gly Tyr Gly Tyr Ala Pro Pro Gln Ala
65                  70                  75                  80

Gln Ala Pro Pro Gly Gln Ala Pro Pro Ser Gln Asp Ala Thr Leu Ala
                85                  90                  95

Ala Gln Leu Gly Gly Met Asn Leu Gly Asp Gly His Gly Thr Ala Arg
                100                 105                 110

Arg Lys Lys Lys Asp Arg His Ala Tyr His Thr Val Glu Pro Thr Gly
            115                 120                 125

Ser Ser Gln Ala Phe Asn Gly Met Pro Pro Gln Gly Thr Ser Ala Thr
            130                 135                 140

Gln Phe Leu Asp Ser Val Pro Gly Gly Pro Gly Phe Gly Gly Gln Phe
145                 150                 155                 160

Gly Ser Pro Gln Gly Thr Pro Gln Met Gln Ser Gln Ser Gln Phe Ser
                165                 170                 175

Ala Pro Val Asn Pro Ala Phe Gly Pro Gly Pro Val Ala Gly Thr Pro
                180                 185                 190

Gly Val Gly Glu Gly Leu Gly Thr Ala Ser Val Ser Thr Ser Gly Pro
                195                 200                 205

Lys Gly Val Ser Pro Asp Asp Met Pro Ser Val Pro Ala Ser Arg Asp
210                 215                 220

Ala Ile Gln Gln Tyr Tyr Leu Lys Asn Val Tyr Pro Thr Phe Glu Arg
225                 230                 235                 240

His Val Pro Pro Pro Ser Thr Val Ser Phe Val Ala Tyr Asp Gln Gly
            245                 250                 255

Asn Ser Ser Pro Lys Tyr Thr Arg Leu Thr Leu Asn Asn Ile Pro Thr
            260                 265                 270

Thr Gln Asp Ala Leu Gln Ala Thr Gly Leu Ser Leu Gly Leu Leu Leu
            275                 280                 285

Gln Pro Leu Ala Pro Leu Gln Ala Gly Glu Ala Glu Ile Pro Val Leu
            290                 295                 300

Asp Phe Gly Glu Ala Gly Pro Pro Arg Cys Arg Cys Arg Ala Tyr
305                 310                 315                 320

Met Asn Pro Phe Met Met Phe Arg Ser Gly Gly Asn Lys Phe Val Cys
                325                 330                 335

Asn Leu Cys Ala Tyr Pro Asn Asp Thr Pro Pro Glu Tyr Phe Ser Ala
                340                 345                 350

Thr Asn Pro Gln Gly Val Arg Val Asp Arg Asp Thr Arg Pro Glu Leu
            355                 360                 365

His Arg Gly Thr Val Glu Phe Val Val Pro Lys Glu Tyr Trp Thr Arg
            370                 375                 380

Glu Pro Val Gly Leu Arg Trp Leu Phe Leu Ile Asp Val Thr Gln Glu
385                 390                 395                 400

Ser Tyr Asn Lys Gly Tyr Val Glu Ala Phe Cys Glu Gly Ile Arg Val
                405                 410                 415
```

-continued

Ala Leu Tyr Gly Gly Glu Asp Gln Glu Leu Asp Glu Asn Gly Glu Pro
                420                 425                 430

Lys Arg Arg Ile Pro Glu Gly Ala Lys Val Gly Phe Val Thr Tyr Asp
                435                 440                 445

Lys Asp Ile His Phe Tyr Asn Val Asn Pro Ala Leu Asp Gln Ala Gln
            450                 455                 460

Met Met Ile Met Pro Asp Leu Glu Asp Pro Phe Val Pro Leu Ser Glu
465                 470                 475                 480

Gly Leu Phe Val Asp Pro Tyr Glu Ser Lys Asp Val Ile Thr Ser Leu
                    485                 490                 495

Leu Thr Arg Leu Pro Asp Met Phe Ser Thr Ile Lys Asn Pro Glu Pro
                500                 505                 510

Ala Leu Leu Ala Ala Leu Asn Ser Ala Leu Ala Ala Leu Glu Ala Thr
                515                 520                 525

Gly Gly Lys Val Val Ala Ser Cys Ser Ala Leu Pro Thr Trp Gly Pro
                530                 535                 540

Gly Arg Leu Phe Met Arg Asp Asn Gly Asn His Pro Gly Gly Glu Ile
545                 550                 555                 560

Asp Lys Lys Leu Tyr Thr Thr Glu His Pro Ala Trp Lys Lys Val Ala
                    565                 570                 575

Glu Lys Met Ala Ala Ser Gly Val Gly Ala Asp Phe Phe Leu Ala Ala
                580                 585                 590

Pro Ser Gly Gly Tyr Leu Asp Ile Ala Thr Ile Gly His Val Ser Ser
                595                 600                 605

Thr Thr Gly Gly Glu Thr Phe Tyr Tyr Pro Asn Phe Ile Ala Ala Arg
                610                 615                 620

Asp Ser Arg Lys Leu Ser Leu Glu Ile Ser His Ala Val Thr Arg Glu
625                 630                 635                 640

Thr Gly Phe Gln Ala Leu Met Lys Val Arg Cys Ser Asn Gly Leu Gln
                    645                 650                 655

Val Ser Gly Tyr His Gly Asn Phe Ile Gln His Thr Phe Gly Ala Asp
                660                 665                 670

Leu Glu Ile Gly Val Ile Asp Ala Asp Lys Ala Met Gly Val Ser Phe
                675                 680                 685

Ser Tyr Asp Gly Lys Leu Asp Pro Lys Leu Asp Ala His Phe Gln Ser
                690                 695                 700

Ala Leu Leu Tyr Thr Thr Ala Ser Gly Glu Arg Arg Val Arg Cys Ser
705                 710                 715                 720

Asn Val Ile Ala Ser Val Thr Glu Thr Ser Lys Glu Ser Gly Ala Arg
                    725                 730                 735

Glu Gln Gly Ile Arg Glu Cys Leu Lys Phe Val Asp Gln Asp Ala Val
                740                 745                 750

Ile Gly Met Leu Ala Lys Glu Ala Ser Thr Lys Leu Ala Thr Thr Ser
                755                 760                 765

Ser Asn Leu Lys Asp Ile Arg His Trp Leu Ser Glu Lys Ala Ile Asp
                770                 775                 780

Val Leu Ala Cys Tyr Arg Lys His Ala Ala Gln Gln His Pro Pro Gly
785                 790                 795                 800

Gln Leu Val Met Pro Glu Arg Leu Lys Glu Tyr Cys Met Tyr Leu Leu
                    805                 810                 815

Gly Leu Leu Lys Cys Arg Ala Leu Lys Gly Gly Val Glu Asn Ser Asp
                820                 825                 830

Arg Arg Val His Glu Met Arg Met Leu Arg Ser Met Gly Ala Leu Glu

```
                     835                 840                 845
Leu Ser Leu Tyr Leu Tyr Pro Arg Met Ile Pro Ile His Asn Leu Ala
         850                 855                 860

Pro Glu Glu Gly Phe Ala Asp Pro Glu Thr Gly His Leu Lys Met Pro
865                 870                 875                 880

Pro Ala Ile Arg Thr Ser Phe Ser Arg Val Glu Pro Gly Gly Val Tyr
                885                 890                 895

Leu Val Asp Asn Gly Gln Gln Cys Leu Leu Trp Phe His Ser Gln Thr
            900                 905                 910

Ser Pro Asn Leu Ile Ser Asp Leu Phe Gly Glu Asp Lys Asp Ser Leu
        915                 920                 925

Lys Ser Leu Asp Pro Tyr Thr Ser Ala Leu Pro Leu Leu Glu Thr His
    930                 935                 940

Leu Asn Ala Gln Val Arg Asn Ile Ile Glu Phe Leu Arg Thr Met Arg
945                 950                 955                 960

Gly Ser Lys Gly Leu Thr Ile Gln Leu Ala Arg Gln Gly Ile Asp Gly
                965                 970                 975

Ala Glu Phe Asp Phe Ala Arg Met Leu Val Glu Asp Arg Asn Asn Glu
            980                 985                 990

Ala Gln Ser Tyr Val Asp Trp Leu  Val His Ile His Lys  Gly Val Gln
        995                  1000                 1005

Leu Glu  Leu Ser Gly Gln Arg  Lys Lys Glu Gly Glu  Glu His Thr
    1010                 1015                 1020

Ala Ala  Ser Leu Ser Asn Phe  Ala Gly Leu Arg Pro  Ala Tyr Trp
    1025                 1030                 1035

<210> SEQ ID NO 9
<211> LENGTH: 34
<212> TYPE: PRT
<213> ORGANISM: Artificial Sequence
<220> FEATURE:
<223> OTHER INFORMATION: synthetic Sfb3 consensus sequence
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 9
```

Ile Gln Leu Ala Arg Gln Gly Xaa Asp Gly Xaa Glu Xaa Xaa Xaa Ala
1               5                   10                  15

Arg Xaa Leu Xaa Glu Asp Arg Asn Xaa Glu Ala Xaa Ser Xaa Val Asp
            20                  25                  30

Trp Leu

<210> SEQ ID NO 10
<211> LENGTH: 3261
<212> TYPE: DNA
<213> ORGANISM: Trichoderma reesei

<400> SEQUENCE: 10

| | | |
|---|---|---:|
| atggactaca | cgcagtatca cgccctgggc cacggcgagg tcctcgaccc caacgacccc | 60 |
| aacaagacgt | ccgctccagc ggctccccag ttccagcccc cctcctcgcc ctacgtgcca | 120 |
| ccgggctccc | cttacggcgc tccccgtac catggcggcc accaagctcc tcccatggca | 180 |
| atgccgcctc | cgtcgacgcc cggctacggc ccgccgcagg ccagagctt ccccgggtct | 240 |
| ccgatgccgt | cgcaggatgc tggccttgcc gcgcagtttg gcgggatgag cctgggtgcg | 300 |
| gatgcgggag | cgccgccgc gaggaagaag aagaaggaca gcacgcgta ccacagcgtg | 360 |
| gagccgacgg | gctcgtcgca ggccttcaat ggcctgccgc cggggacgcc cgccgagcag | 420 |
| ttcctcaacg | tcaacaaccc gcagggcatc ccggcgctgg agggcagtt tggaagccct | 480 |
| ctggccagcc | ccatgggcac gcctcacatg ccaatccgg ccagttccc ggcgccaacc | 540 |
| tctcccttca | cccctcggc ccctgtgtcg ccggccgagt tcgcatccag gtttggctct | 600 |
| cccgacgctg | ccacgtcaat aggctcggct ggccccagcc aggtgtcgcc agacgacatg | 660 |
| cccagcatac | ccgcctcgag ggacgccatc caggagcact tttttaagaa cgtttacccg | 720 |
| accttcgagc | gccatgtgcc ccctcctgcg acggtttcct tgttgccttt cgaccaaggc | 780 |
| aatgcctctc | ccaaattcac ccgactcacc tcaacaaca tcccaaccac agccgagggc | 840 |
| ctccatgcga | cgggcttgcc cctgggcatg ctcatccagc ctctggcccc acttcaagcg | 900 |
| ggagaggccg | agattcccgt tctcgacttt ggcgacgccg gccgcctcg atgtcgaaga | 960 |
| tgccgggctt | atatcaaccc cttcatgatg ttccgatcgg gcggcaacaa gttcgtgtgc | 1020 |
| aacctctgct | cgtaccccaa cgaaacgccg cccgagtact tttgcgccgt cagcccacag | 1080 |
| ggagtgcgcc | tagatcgaga ccagcggccg gagcttcacc gcggtaccgt cgagttcgtc | 1140 |
| gtccccaagg | agtactggac ccgagagccc gtcggcctcc gctggctgtt tgtcatcgac | 1200 |
| gtcacgcagg | aatcctataa caagggcttc atggagacat tctgcgaggg catcctcgcg | 1260 |
| gccctctacg | cggcaacga cgaggagaat gatgaagatg gcgagccaaa gcgaaggata | 1320 |
| cccaagggag | ccaaggttgg gttcatcacg tacgacaagg acattcactt ttacaacatc | 1380 |
| aacgtgagtt | cacgagcact gggaacaaga atgagatggc ccgctaacat taagacagcc | 1440 |
| tcatctggat | caagcgcaca tgatgatcat gcccgacctc gaagacccat tcctcccct | 1500 |
| cggcgagggc | ctctttgtcg acccgtacga gtcaaaggcc atcatcacct ctctcctcac | 1560 |
| ccgcctcccc | gagatgttct ccaccatcaa aaaccccgag cccgctctgc ttgccacgct | 1620 |
| caatgccgcc | gtggctgcgc tggaggcaac gggaggtaaa gtcgtgtgct cgtgctcgac | 1680 |
| cttgcctacc | tggggccctg gccgactgtt catgcgcgac gacggcaacc atcccggtgg | 1740 |
| cgagctggac | aagaagctgt atacgacgga acaccccgcg tggaagaagg tctcggagaa | 1800 |
| gatggcttcg | tccggcattg gtgtcgactt cttccttgct gcgccctccg gcggctacct | 1860 |

```
ggacattgcg acgataggcc atgtcgccgc cacgactggt ggagagacgt tctactaccc    1920
caacttcatc gccccgcgag acggtgcccg gctgtcaatg gagattacgc acgccatcac    1980
gagggaaacg ggcttccagg cgctgatgaa ggtccgctgc tcgaccgggc tgcaggtggc    2040
ggcgtaccac ggcaactttg tccagcacac ctttggggca gacctggaga ttggcgtcat    2100
tgacgcggac aaggcgctcg gcgtgtcgtt tagccacgac ggtaaactgg atcccaagct    2160
ggacgcccac ttccagacgg ctctcctgta cacgaccgcg tccggacagc gacgcgtgcg    2220
atgttccaac gtgattgcca gcgtcagcga cacctccaag gagtccaaca ccaaggagct    2280
ggccattcgg cagtgcctca gtttgtcga ccaggacgcg gttgtgggta tctttgcaaa    2340
agaagccagc accaagctcg ccacgacatc ggccaatctc caggatgtgc gaaactggct    2400
gacggagcga acaatcgaca tcatggccta ctacaagaag cactctgcca atcagttccc    2460
tccgagccag ctggtcatgc ccgaacggct gaaggagttc tgcatgtaca tgctaggcat    2520
gttgaaatgc agagctttca agggcggtat cgagaactcg gatcgcagag tgcacgagct    2580
gcgcatggtc cgcagcatgg gcccgctgga gcttagcctg tatctgtacc cccggatgat    2640
tgctctgcac aacctccagc ccgaagaggg ctttgccgac cccgaaacag gccacctcaa    2700
gatgcccccg tccgtgcgga cgtccttttc acgggtcgag ccgggtggcg tctacctggt    2760
ggacaacgga cagcagtgct tgctgtggtt tcacgcccag acgtcgccca acctcatcac    2820
cgacctgttt ggcgagggcc acgactcgct caaggggctg gatccgtaca cgtccacgct    2880
gccggtgctg gagacgcatc tcagcgcaca ggtccgcaac attattgagt tcctcaaaag    2940
catgagggga tccaagggca tgacgataca gctggcgcgg caggggattg acggcgccga    3000
gtacgagttt gcgcggatgt tggtggagga tcgcaacaat gaggcgaaga gctacgttga    3060
ctggcttgtt cacattcaca gaggagttca gctggaggta tgttccccg cctccccccct    3120 tttccccctt gcgtcgtcgt caggagatga tgagaatgct aattcgtcct atagttgagc    3180
ggacaacgaa agaaggaagg cgatggagag gctaccgccg taatggccaa ctttgcagga    3240
ctgagaccgg cctattggta g                                              3261
```

<210> SEQ ID NO 11
<211> LENGTH: 30
<212> TYPE: DNA
<213> ORGANISM: Artificial Sequence
<220> FEATURE:
<223> OTHER INFORMATION: synthetic primer

<400> SEQUENCE: 11
cacagtcgac cagctggact gactgtgccc                                      30

<210> SEQ ID NO 12
<211> LENGTH: 30
<212> TYPE: DNA
<213> ORGANISM: Artificial Sequence
<220> FEATURE:
<223> OTHER INFORMATION: synthetic primer

<400> SEQUENCE: 12
gagaagatct gaggaggctc tcgcaggaga                                      30

<210> SEQ ID NO 13
<211> LENGTH: 70
<212> TYPE: DNA
<213> ORGANISM: Artificial Sequence
<220> FEATURE:
<223> OTHER INFORMATION: synthetic primer -continued

<400> SEQUENCE: 13
gaaagatcta cagataactt cgtatagcat acattatacg aagttatcct gggcttgtga    60
ctggtcgcga                                                           70

<210> SEQ ID NO 14
<211> LENGTH: 73
<212> TYPE: DNA
<213> ORGANISM: Artificial Sequence
<220> FEATURE:
<223> OTHER INFORMATION: synthetic primer

<400> SEQUENCE: 14
gcaagcggcc gcaagtataa cttcgtataa tgtatgctat acgaagttat cggccggcgt    60
attgggtgtt acg                                                       73

<210> SEQ ID NO 15
<211> LENGTH: 30
<212> TYPE: DNA
<213> ORGANISM: Artificial Sequence
<220> FEATURE:
<223> OTHER INFORMATION: synthetic primer

<400> SEQUENCE: 15
gagagcggcc gcgggcgtca atggcagagg                                     30

<210> SEQ ID NO 16
<211> LENGTH: 28
<212> TYPE: DNA
<213> ORGANISM: Artificial Sequence
<220> FEATURE:
<223> OTHER INFORMATION: synthetic primer

<400> SEQUENCE: 16
ttaatctaga cgtgttgtgc ggagaggc                                       28

<210> SEQ ID NO 17
<211> LENGTH: 19
<212> TYPE: DNA
<213> ORGANISM: Artificial Sequence
<220> FEATURE:
<223> OTHER INFORMATION: synthetic primer

<400> SEQUENCE: 17
cagctggact gactgtgcc                                                 19

<210> SEQ ID NO 18
<211> LENGTH: 18
<212> TYPE: DNA
<213> ORGANISM: Artificial Sequence
<220> FEATURE:
<223> OTHER INFORMATION: synthetic primer

<400> SEQUENCE: 18
agaggcccat gctgttgg                                                  18

<210> SEQ ID NO 19
<211> LENGTH: 18
<212> TYPE: DNA
<213> ORGANISM: Artificial Sequence
<220> FEATURE:
<223> OTHER INFORMATION: synthetic primer

<400> SEQUENCE: 19

| | |
|---|---|
| ttcctccgtt ctccctga | 18 |

\<210\> SEQ ID NO 20
\<211\> LENGTH: 18
\<212\> TYPE: DNA
\<213\> ORGANISM: Artificial Sequence
\<220\> FEATURE:
\<223\> OTHER INFORMATION: synthetic primer

\<400\> SEQUENCE: 20

| | |
|---|---|
| gcggtgagtt caggctttt | 18 |

\<210\> SEQ ID NO 21
\<211\> LENGTH: 18
\<212\> TYPE: DNA
\<213\> ORGANISM: Artificial Sequence
\<220\> FEATURE:
\<223\> OTHER INFORMATION: synthetic primer

\<400\> SEQUENCE: 21

| | |
|---|---|
| aaattccgtc accagccc | 18 |

\<210\> SEQ ID NO 22
\<211\> LENGTH: 18
\<212\> TYPE: DNA
\<213\> ORGANISM: Artificial Sequence
\<220\> FEATURE:
\<223\> OTHER INFORMATION: synthetic primer

\<400\> SEQUENCE: 22

| | |
|---|---|
| cttgcgttgg ctcacaga | 18 |

\<210\> SEQ ID NO 23
\<211\> LENGTH: 21
\<212\> TYPE: DNA
\<213\> ORGANISM: Artificial Sequence
\<220\> FEATURE:
\<223\> OTHER INFORMATION: synthetic primer

\<400\> SEQUENCE: 23

| | |
|---|---|
| gagtggtgaa gtcggtaatc c | 21 |

\<210\> SEQ ID NO 24
\<211\> LENGTH: 20
\<212\> TYPE: DNA
\<213\> ORGANISM: Artificial Sequence
\<220\> FEATURE:
\<223\> OTHER INFORMATION: synthetic primer

\<400\> SEQUENCE: 24

| | |
|---|---|
| ctggaaacgc aaccctgaag | 20 |

\<210\> SEQ ID NO 25
\<211\> LENGTH: 28
\<212\> TYPE: DNA
\<213\> ORGANISM: Artificial Sequence
\<220\> FEATURE:
\<223\> OTHER INFORMATION: synthetic primer

\<400\> SEQUENCE: 25

| | |
|---|---|
| cacccgata gaaggcacag caacgctt | 28 |

\<210\> SEQ ID NO 26
\<211\> LENGTH: 25
\<212\> TYPE: DNA
\<213\> ORGANISM: Artificial Sequence

```
<220> FEATURE:
<223> OTHER INFORMATION: synthetic primer

<400> SEQUENCE: 26
gtgatggaag caatgtagtc cgcag                                    25

<210> SEQ ID NO 27
<211> LENGTH: 28
<212> TYPE: DNA
<213> ORGANISM: Artificial Sequence
<220> FEATURE:
<223> OTHER INFORMATION: synthetic primer

<400> SEQUENCE: 27
caccatggac tacacgcagt atcacgcc                                 28

<210> SEQ ID NO 28
<211> LENGTH: 25
<212> TYPE: DNA
<213> ORGANISM: Artificial Sequence
<220> FEATURE:
<223> OTHER INFORMATION: synthetic primer

<400> SEQUENCE: 28
ctaccaatag gccggtctca gtcct                                    25

<210> SEQ ID NO 29
<211> LENGTH: 30
<212> TYPE: DNA
<213> ORGANISM: Artificial Sequence
<220> FEATURE:
<223> OTHER INFORMATION: synthetic primer

<400> SEQUENCE: 29
gagaactagt acccgactca ccctcaacaa                               30

<210> SEQ ID NO 30
<211> LENGTH: 30
<212> TYPE: DNA
<213> ORGANISM: Artificial Sequence
<220> FEATURE:
<223> OTHER INFORMATION: synthetic primer

<400> SEQUENCE: 30
gagaagatct agtgtggtgt gattgtcccg                               30

<210> SEQ ID NO 31
<211> LENGTH: 34
<212> TYPE: DNA
<213> ORGANISM: Artificial Sequence
<220> FEATURE:
<223> OTHER INFORMATION: synthetic primer

<400> SEQUENCE: 31
aattgcggcc gctgcctagg tatggattta ctcc                          34

<210> SEQ ID NO 32
<211> LENGTH: 31
<212> TYPE: DNA
<213> ORGANISM: Artificial Sequence
<220> FEATURE:
<223> OTHER INFORMATION: synthetic primer

<400> SEQUENCE: 32
gtgttctaga cgattatgtc gtgagcctct a                             31
```

```
<210> SEQ ID NO 33
<211> LENGTH: 19
<212> TYPE: DNA
<213> ORGANISM: Artificial Sequence
<220> FEATURE:
<223> OTHER INFORMATION: synthetic primer

<400> SEQUENCE: 33
ccgactcacc ctcaacaac                                                   19

<210> SEQ ID NO 34
<211> LENGTH: 20
<212> TYPE: DNA
<213> ORGANISM: Artificial Sequence
<220> FEATURE:
<223> OTHER INFORMATION: synthetic primer

<400> SEQUENCE: 34
cgattatgtc gtgagcctct                                                  20

<210> SEQ ID NO 35
<211> LENGTH: 18
<212> TYPE: DNA
<213> ORGANISM: Artificial Sequence
<220> FEATURE:
<223> OTHER INFORMATION: synthetic primer

<400> SEQUENCE: 35
tcaataggct cggctggc                                                    18

<210> SEQ ID NO 36
<211> LENGTH: 18
<212> TYPE: DNA
<213> ORGANISM: Artificial Sequence
<220> FEATURE:
<223> OTHER INFORMATION: synthetic primer

<400> SEQUENCE: 36
ccacggcgaa gaatccac                                                    18

<210> SEQ ID NO 37
<211> LENGTH: 18
<212> TYPE: DNA
<213> ORGANISM: Artificial Sequence
<220> FEATURE:
<223> OTHER INFORMATION: synthetic primer

<400> SEQUENCE: 37
ctccggcgaa gcagaaga                                                    18

<210> SEQ ID NO 38
<211> LENGTH: 18
<212> TYPE: DNA
<213> ORGANISM: Artificial Sequence
<220> FEATURE:
<223> OTHER INFORMATION: synthetic primer

<400> SEQUENCE: 38
tcatgctgtg tcctgccg                                                    18

<210> SEQ ID NO 39
<211> LENGTH: 18
<212> TYPE: DNA
<213> ORGANISM: Artificial Sequence
<220> FEATURE:
<223> OTHER INFORMATION: synthetic primer
```

```
<400> SEQUENCE: 39
gcctctccca aattcacc                                                   18

<210> SEQ ID NO 40
<211> LENGTH: 18
<212> TYPE: DNA
<213> ORGANISM: Artificial Sequence
<220> FEATURE:
<223> OTHER INFORMATION: synthetic primer

<400> SEQUENCE: 40
tggtggagaa catctcgg                                                   18
```

FILAMENTOUS FUNGI HAVING AN ALTERED VISCOSITY PHENOTYPE

PRIORITY

The present application is a U.S. National Phase Application of International Application No. PCT/US2011/049164, filed Aug. 25, 2011, which claims priority to U.S. Provisional Application Ser. No. 61/377,030, filed Aug. 25, 2010, which are incorporated by reference in their entireties.

SEQUENCE LISTING

The sequence listing submitted via EFS, in compliance with 37 C.F.R. § 1.52(e), is incorporated herein by reference. The sequence listing text file submitted via EFS contains the file "31463US-2-SEQ-LIST Corrected" created on Apr. 4, 2013, which is 81,920 bytes in size.

TECHNICAL FIELD

The present strains and methods relate to genetic mutations in filamentous fungi that give rise to variants having altered growth characteristics. Such variants are well-suited for growth in submerged cultures, e.g., for the large-scale production of enzymes and other proteins or metabolites for commercial applications.

REFERENCES

The following references, and additional reference cited herein, are hereby incorporated by reference:

Caracuel, Z. et al. (2005) *Molecular Plant-Microbe Interactions* 18:1140-47.
Hughes, H. and Stephens, D. J. (2008) *Cell Biol.* 129:129-51.
Karhinen, L. et al, (2005) *Traffic* 6:562-74.
Mouyna, I. et al. (2005) *Molecular Microbiology* 56:1675-88.
Passolunghi, S. et al. (2010) *Microbial Cell Factories* 9:7-17.
Peng, R. et al. (2000) *J. Biol. Chem.* 275:11521-28.
Roberg, K. J. et al. (1999) *J. Cell. Biol.* 145:659-72.
Shimoni, Y. et al. (2000) *J. Cell. Biol.* 151:973-84.
Turchini, A. et al. (2000) *J. Becteriol.* 182:1167-71.

BACKGROUND

Filamentous fungi are capable of expressing native and heterologous proteins to high levels, making them well-suited for the large-scale production of enzymes and other proteins for industrial applications. Filamentous fungi are typically grown in mycelial submerged cultures in bioreactors, which are adapted to introduce and distribute oxygen and nutrients into the culture medium (i.e., broth). The morphological characteristics of the mycelium affect the rheological properties of the broth, thereby affecting bioreactor performance.

Generally, the higher the viscosity of the broth, the less uniform the distribution of oxygen and nutrients, and the more energy required to agitate the culture. In some cases, the viscosity of the broth becomes sufficiently high to significantly interfere with the dissolution of oxygen and nutrients, thereby adversely affecting the growth of the fungi. Additionally, the power required to mix and aerate viscous broth can significantly increase the cost of production, and incur higher capital expenditures in terms of motors and power supplies.

SUMMARY

Described are strains and methods relating to filamentous fungi having genetic alterations that give rise to altered viscosity phenotypes.

In one aspect, a variant strain of filamentous fungus derived from a parental strain is provided, the variant strain comprising a genetic alteration that causes cells of the variant strain to produce an altered amount of functional Sfb3 protein compared to cells of the parental strain, wherein the cells of the variant strain produce during aerobic fermentation in submerged culture a cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.

In some embodiments, the altered amount of functional Sfb3 protein is a reduced amount, and the variant strain produce during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.

In some embodiments, the genetic alteration comprises a disruption of the sfb3 gene present in the parental strain. In some embodiments, disruption of the sfb3 gene is the result of deletion of all or part of the sfb3 gene. In some embodiments, disruption of the sfb3 gene is the result of deletion of a portion of genomic DNA comprising the sfb3 gene. In some embodiments, disruption of the sfb3 gene is the result of mutagenesis of the sfb3 gene.

In some embodiments, disruption of the sfb3 gene is performed using site-specific recombination. In some embodiments, disruption of the sfb3 gene is performed in combination with introducing a selectable marker at the genetic locus of the sfb3 gene. In some embodiments, disruption of the sfb3 gene is the primary genetic determinant for conferring a reduced viscosity phenotype to the variant strain.

In some embodiments, the variant strain does not produce functional Sfb3 protein. In some embodiments, the variant strain does not produce Sfb3 protein.

In some embodiments, the variant strain further comprises a gene encoding a protein of interest.

In some embodiments, the variant strain produces substantially the same amount of protein per unit amount of biomass as the parental strain. In some embodiments, the variant strain produces substantially the same amount of protein of interest per unit amount of biomass as the parental strain.

In some embodiments, the Sfb3 protein comprises the amino acid sequence IQLARQGXDGXEXXXARXLX-EDRNXEAXSXVDWL (SEQ ID NO: 9, where X is any amino acid residue).

In some embodiments, the filamentous fungus is a *Pezizomycotina* species. In some embodiments, the filamentous fungus is *Trichoderma reesei*.

In another aspect, a method for producing a variant strain of filamentous fungus cells is provided, comprising: introducing a genetic alteration into a parental strain of filamentous fugal cell, which genetic alteration alters the production of functional Sfb3 protein compared to the cells of the parental strain, thereby producing a variant filamentous fugal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

In some embodiments, the genetic alteration reduces or prevents the production of functional Sfb3 protein, thereby producing a variant filamentous fugal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

In some embodiments, the genetic alteration comprises disrupting the sfb3 gene in a parental filamentous fugal cell using genetic manipulation.

In some embodiments, the genetic alteration comprises deleting the sfb3 gene in a parental filamentous fugal cell using genetic manipulation.

In some embodiments, the genetic alteration is performed using site-specific genetic recombination. In some embodiments, the disruption of the sfb3 gene is performed in combination with introducing a selectable marker at the genetic locus of the sfb3 gene.

In some embodiments, the variant strain produces substantially the same amount of protein per unit amount of biomass as the parental strain. In some embodiments, the variant strain produces substantially the same amount of protein of interest per unit amount of biomass as the parental strain.

In some embodiments, the Sfb3 protein comprises the amino acid sequence IQLARQGXDGXEXXXARXLX-EDRNXEAXSXVDWL (SEQ ID NO: 9, where X is any amino acid residue).

In some embodiments, the filamentous fungus is a *Pezizomycotina* species. In some embodiments, the filamentous fungus is *Trichoderma reesei*.

In some embodiments, the parental strain further comprises a gene encoding a protein of interest. In some embodiments, the gene encoding the protein of interest is present in the parental strain prior to introducing the genetic alteration that reduces or prevents the production of functional Sfb3 protein.

In another aspect, a protein of interest produced by the foregoing variant strain is provided.

In another aspect, a variant strain of filamentous fungus produced by the foregoing method is provided.

In another aspect, a variant strain of filamentous fungus derived from a parental strain is provided, the variant strain comprising: (a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and (b) a gene encoding a protein of interest, wherein the gene encoding the protein of interest is present in the variant strain prior to the genetic alteration in (a).

In some embodiments, the genetic alteration comprises a disruption of the sfb3 gene present in the parental strain. In some embodiments, disruption of the sfb3 gene is performed in combination with introducing a selectable marker at the genetic locus of the sfb3 gene.

In another aspect, a method for screening variant filamentous fungus cells for an altered viscosity phenotype is provided, comprising: (a) mutagenizing the cells of a parental strain of filamentous fungi to produce variant cells; (b) screening the variant cells for altered sensitivity to a fluorochrome stain; and (c) selecting the variant cells that have altered sensitivity to the fluorochrome stain; wherein the altered sensitivity to the fluorochrome stain correlates with the ability of the variant filamentous fungus cells to produce, during aerobic fermentation in submerged culture, a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

In some embodiments, the altered sensitivity is increased sensitivity, and the variant filamentous fugal cell produces, during aerobic fermentation in submerged culture, a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain. In some embodiments, the fluorochrome stain is Calcofluor White.

In some embodiments, mutagenizing the cells is performed by genetic recombination. In some embodiments, mutagenizing the cells is performed in combination with introducing a selectable marker at the genetic locus of the sfb3 gene.

In another aspect, a method for identifying a Sfb3 polypeptide in *Pezizomycotina* species of filamentous fungus is provided, comprising: (a) obtaining an amino acid sequence from a *Pezizomycotina* species of filamentous fungus; and (b) screening the amino acid sequence for the presence of the contiguous amino acid sequence IQLARQGXDGXEXXX-ARXLXEDRNXEAXSXVDWL (SEQ ID NO: 9, where X is any amino acid residue); (c) wherein the presence of SEQ ID NO: 9 in the amino acid sequence from the *Pezizomycotina* species of filamentous fungus indicates that the amino acid sequence from the *Pezizomycotina* species of filamentous fungus is a sfb3 polypeptide.

In another aspect, an isolated sfb3 polypeptide identified by the foregoing method is provided.

In yet a further aspect, a method for producing a protein of interest in filamentous fungus cells is provided, comprising introducing into parental filamentous fungus cells a gene encoding the protein of interest and a genetic alteration that reduces the amount or activity of Sfb3 protein in the cells, thereby producing a variant filamentous fugal cell that produces during aerobic fermentation in submerged culture a cell broth comprising the protein of interest, which (i) requires an altered amount of agitation to maintain a preselected dissolved oxygen content compared to the cells of the parental strain, and/or (ii) maintains an altered dissolved oxygen content at a preselected amount of agitation compared to the cells of the parental strain, and wherein the protein of interest is produced at substantially the same level in the variant cells compared to the parental cells.

In some embodiments, the protein of interest is more than one protein (or one or more proteins) of interest, and each of the more than one protein of interest is produced at substantially the same relative levels in the variant cells compared to the parental cells. In a particular embodiment, each of the more than one protein of interest is selected from cellulases and hemicellulases.

In a related aspect, a protein of interest produced by such a method is provided. In yet another related aspect, a composition comprising more than one protein of interest produced by such method is provided. In some embodiments, the composition is a whole cellulase composition.

These and other aspects and embodiments of present strains and methods will be apparent from the description, including the accompanying Figures.

BRIEF DESCRIPTION OF THE DRAWINGS

FIG. 5 is an image showing the loss of hygromycin B resistance and the ability to grow on acetamide in candidates following transient expression of plasmid pTrex-Tel-pyrG13/pDONR221/0927853cre. Top row (A-C): Morph and Morph Δsfb3 control strains on the indicated media. Bottom row (D-F): candidates after transient expression of the plasmid on the indicated media.

FIG. 8 is an image showing the growth of 70H2 and 29-9 transformants on PDA with hygromycin B after four days of growth at 28° C. (first transfer from transformation plates). (A-C) 70H2+wild type sfb3 from 29-9. (D-F) 70H2+wild type sfb3 with native promoter and terminator from 29-9. (G) 29-9+ vector only. (H-J) 70H2+sf3 from 70H2. (K-M) 70H2+sfb3 with native promoter and terminator from 70H2. (N) 70H2+vector only.

FIG. 13 shows an alignment of the amino acid sequences of the Sfb3proteins from *S. cerevisiae* (SEQ ID NO: 1) and *T. reesei* (SEQ ID NO: 2).

FIG. 14 shows an alignment of the amino acid sequences of the Sfb3proteins from *S. cerevisiae* (SEQ ID NO: 1), *T. reesei* (SEQ ID NO: 2), and *A. oryzae* (SEQ ID NO: 3).

DETAILED DESCRIPTION

I. Overview

Figure 1:
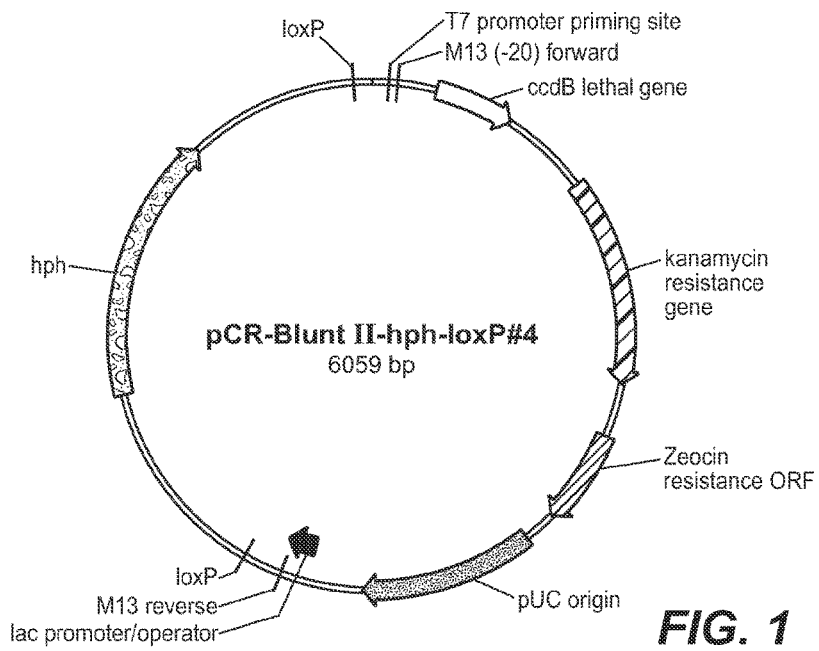
FIG. 1 is map of plasmid pCR-BluntII-hph-loxP#4

The present strains and methods relate to variant filamentous fungus cells having genetic modifications that affect their morphology and growth characteristics. When the variant cells are grown in submerged culture, they produce a cell broth that has different rheological properties compared to a cell broth comprising cells of the parental strain. Some of these variant strains are well-suited for the large-scale production of enzymes and other commercially important proteins.

II. Definitions

Prior to describing the present strains and methods in detail, the following terms are defined for clarity. Terms not defined should be accorded their ordinary meanings as used in the relevant art.

As used herein, "Trichoderma reesei" refers to a filamentous fungus of the phylum *Ascomycota*, subylum *Pezizomycotina*. This organism was previously classified as *Trichoderma longibrachiatum*, and also as *Hypocrea jecorina*.

As used herein, the phrase "variant strain of filamentous fungus cells," or similar phrases, refer to strains of filamentous fungus cells that are derived (i.e., obtained from or obtainable from) from a parental (or reference) strain belonging to the *Pezizomycotina*, e.g., by genetic manipulation.

As used herein, the term "protein of interest" refers to a polypeptide that is desired to be expressed in a filamentous fungus, optionally at high levels and for the purpose of commercialization. Such a protein may be an enzyme, a substrate-binding protein, a surface-active protein, a structural protein, or the like.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" are used interchangeably to refer to polymers of any length comprising amino acid residues linked by peptide bonds. The conventional one-letter or three-letter codes for amino acid residues are used herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins may be derived from organisms of different genera and/or species, or even different classes of organisms (e.g., bacteria and fungus). Related proteins also encompass homologs determined by primary sequence analysis, determined by secondary or tertiary structure analysis, or determined by immunological cross-reactivity.

As used herein, the term "derivative polypeptide/protein" refers to a protein which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative may be achieved by modifying a DNA sequence which encodes for the native protein, transformation of that DNA sequence into a suitable host, and expression of the modified DNA sequence to form the derivative protein.

Related (and derivative) proteins include "variant proteins." Variant proteins differ from a reference/parental protein (e.g., a wild-type protein) by substitutions, deletions, and/or insertions at small number of amino acid residues. The number of differing amino acid residues between the variant and parental protein may be one or more, for example, 1, 2, 3, 4, 5, 6, 7, 8, 9, 10, 15, 20, 30, 40, 50, or more amino acid residues. Variant proteins may share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein may also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an α-helix or a β-sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an α-helix or a β-sheet structure, the replacement amino acids preferably maintain that specific structure.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences may be determined using any suitable method known in the art (see, e.g., Smith and Waterman (1981) *Adv. Appl. Math.* 2:482; Needleman and Wunsch (1970) *J. Mol. Biol.*, 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, Wis.); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'S, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity may be determined using known programs such as BLAST, ALIGN, and CLUSTAL using standard parameters. (See, e.g., Altschul, et al. (1990) *J. Mol. Biol.* 215:403-410; Henikoff et al. (1989) *Proc. Natl. Acad. Sci. USA* 89:10915; Karin et al. (1993) *Proc. Natl. Acad. Sci USA* 90:5873; and Higgins et al. (1988) *Gene* 73:237-244). Software for performing BLAST analyses is publicly available through the National Center for Biotechnology Information. Also, databases may be searched using FASTA (Pearson et al. (1988) *Proc. Natl. Acad, Sci. USA* 85:2444-48). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, "wild-type" and "native" genes, proteins, or strains, are those found in nature.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent promoter and/or terminator sequences.

As used herein, "disruption of a gene" refers broadly to any genetic or chemical manipulation that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product.

As used herein, "genetic manipulation" refers to the alteration of a preselected nucleic acid target sequence, e.g., using macromolecules (i.e., enzymes and/or nucleic acids) that preferentially act on the preselected nucleic acid sequence. In this manner genetic manipulation is distinct from chemical manipulation, in which small molecules are used to randomly affect changes to a nucleic acid sequence that is not preselected.

As used herein, a "genetic alteration" is a change in the DNA of a cell that results from genetic manipulation, and is distinct from a change in the DNA of a cell that results from chemical manipulation.

As used herein, "aerobic fermentation" refers to growth in the presence of oxygen.

As used herein, the term "cell broth" refers collectively to medium and cells in a liquid/submerged culture.

As used herein, the term "cell mass" refers to the cell component (including intact and lysed cells) present in a liquid/submerged culture. Cell mass may be expressed in dry or wet weight.

As used herein, the term "rheology" refers to a branch of physics dealing with the deformation and flow of matter.

As used herein, "viscosity" is a measure of the resistance of a fluid to deformation by mechanical stress, such as shear stress or tensile stress. In the present context, viscosity refers to the resistance of a cell broth comprising filamentous fungus cells to mechanical stress, e.g., as provided by a rotor/impeller. Because the viscosity of a cell broth can be difficult to measure directly, indirect measurements of viscosity may be used, such as the dissolved oxygen content of the culture broth at a preselected amount of agitation, the amount of agitation required to maintain a preselected dissolved oxygen content, the amount of power required to agitate a cell broth to maintain a preselected dissolved oxygen content, or even colony morphology on solid medium.

As used herein, an "altered-viscosity" variant strain of filamentous fungus cells is a variant strain that produces a cell broth that has a reduced or increased viscosity (i.e., reduced or increased resistance to shear or tensile stress) compared to an equivalent cell broth produced by a parental strain. Generally, equivalent cell broths have comparable cell masses. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more. Methods for comparing the viscosity of filamentous fungus cells broth are described, herein. Generally, comparable (or equivalent) cell broths have comparable cell masses.

As used herein, a "reduced-viscosity" variant strain of filamentous fungus cells is a variant strain that produces a cell broth that has reduced viscosity (i.e., reduced resistance to shear or tensile stress) compared to an equivalent cell broth produced by a parental strain. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more.

As used herein, a "primarily genetic determinant" refers to a gene, or genetic manipulation thereof, that is necessary and sufficient to confer a specified phenotype in the absence of other genes, or genetic manipulations, thereof.

As used herein, a "functional polypeptide/protein" is a protein that posses an activity, such as an enzymatic activity, a binding activity, a surface-active property, or the like, and which has not been mutagenized, truncated, or otherwise modified to abolish or reduce that activity. Functional polypeptides may be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product.

As used herein, variant cells (or a variant strain) "maintain or retain a high level of protein expression and/or secretion" compared to parental cells (or a parental strain) if the difference in protein expression between the variant cells and a parental cells is less than about 20%, less than about 15%, less than about 10%, less than about 7%, less than about 5%, or even less than about 3%.

As used herein, host cells have been "modified to prevent the production of a Sfb3" if they have been genetically or chemically altered to prevent the production of a functional Sfb3 polypeptide that exhibits an activity characteristic of wild-type Sfb3 protein, particularly an activity that promotes elongation of hyphae or otherwise increases the viscosity of a filamentous fungus in liquid culture. Such modifications include, but are not limited to, deletion of the sfb3 gene, disruption of the sfb3 gene, modification of the sfb3 gene such that the encoded polypeptide lacks the aforementioned activity, modification of the sfb3 gene to affect post-translational processing or stability, and combinations, thereof.

As used herein, a "protein of interest" is a protein that is desired to be produced in a submerged culture of filamentous fungus cells. Generally, proteins of interest are commercially important for industrial or pharmaceutical use, making them desirable to produce in large quantities. Proteins of interest are to be distinguished from myriad other proteins expressed by the filamentous fungus cells, which are generally not of interest as products and are mainly considered background protein contaminants.

As used herein, variant cells (or a variant strain) produce(s) "substantially the same amount" of protein per unit amount of biomass as parental cells (or a parental strain) if the amount of protein produced by the variant cells is no more than 20% reduced, no more than 15% reduced, no more than 10% reduced, an even no more than 5% reduced compared to the amount of protein produced by the parental cells, wherein the amount of protein is normalized to the total amount of biomass of cells from which protein production is measured, wherein biomass may be expressed in terms of either wet (e.g., of cell pellet) or dry weight.

As used herein, the amount of protein of interest expressed by variant cells and parental cells is "substantially similar" if the difference in expression between the variant cells and the parental cells is less than about 20%, less than about 15%, less than about 10%, less than about 5%, less than about 4%, less than about 3%, less than about 2%, or even less than about 1%.

As used herein, "fluorochromes" are fluorescent dyes. Preferred fluorochromes bind to cellulose and/or chitin in the cell walls of fungi.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

EC enzyme commission
kDa kiloDalton
kb kilobase
MW molecular weight
w/v weight/volume
w/w weight/weight
v/v volume/volume
wt % weight percent
° C. degrees Centigrade
$H_2O$ water
$H_2O_2$ hydrogen peroxide
$dH_2O$ or DI deionized water
$dIH_2O$ deionized water, Milli-Q filtration
g or gm gram
μg microgram
mg milligram
kg kilogram
lb pound
μL and μl microliter
mL and ml milliliter
mm millimeter
μm micrometer
M molar
mM millimolar
μM micromolar
U unit
ppm parts per million
sec and " second
mM and ' minute
hr hour
EtOH ethanol
eq. equivalent
N normal
PCR polymerase chain reaction
DNA deoxyribonucleic acid
FOA fluoroorotic acid
UV ultraviolet
$A_{540}$ absorbance measured at a wavelength of 540 nm
CMC carboxymethyl cellulose
rpm revolutions per minute
Δ relating to a deletion
DO dissolved oxygen III. The Reduced Viscosity Phenotype in Filamentous Fungi Previous efforts to develop reduced viscosity strains of *Trichoderma reesei* involved chemical mutagenesis, followed by screening the resulting mutants (sometimes referred to herein as "strains") for sensitivity to Calcofluor White, a fluorochrome stain that binds to cellulose and chitin in the cell walls of fungi. Sensitivity to Calcofluor White is associated with changes in yeast morphology, although the significance of Calcofluor White sensitivity in filamentous fungi was heretofore unknown. In this manner the parental *Trichoderma reesei* strain Morph TrglaA (29-9) was chemically mutagenized, and one resulting strain (i.e., 70H2) was found to exhibit reduced colonial growth rate on agar plates, reduced sporulation, altered morphology, and reduced viscosity in liquid medium, while maintaining a high level of protein expression and secretion. Comparative genomic sequence analysis revealed mutations in multiple genes in the 70H2 strain, compared to parental 29-9 strain.

While the 70H2 strain demonstrated a "reduced viscosity" phenotype, it lacked a fully defined genome, and the gene or genes responsible for the reduced viscosity phenotype were unknown. Moreover, while 70H2 could be used as host strain for introducing exogenous genes for high levels of expression, it was not possible to introduce the gene or genes responsible for the reduced viscosity phenotype into other strains.

IV. Alterations in Sfb3 Production Affect Cell Viscosity in Filamentous Fungus

It has now been discovered that alterations in Sfb3 production affect cell viscosity in filamentous fungus. This discovery has significant implications for the use of filamentous fungi for the expression of commercially important proteins.

The Sfb3 gene (also known as Lst1) has previously only been characterized in budding yeast (i.e., *Saccharomyces cerevisiae*), where it encodes a protein associated with the COPII protein coat surrounding transport vesicles that carry proteins from the endoplasmic reticulum to the Golgi apparatus. Sfb3, as well as Sfb2, are homologs of Sec24, all of which genes are involved with packaging specific cargo proteins into the vesicles.

While Sec24 is an essential gene in yeast, Sfb3 and Sfb2 are not, although the deletion of Sfb3 in yeast is known to affect the transport of a plasma membrane transport protein (Pma1p) and a glucanosyltransferase (Gas1p) that is involved in cell wall synthesis.

Using BLAST to search the publicly available genome sequence of *Trichoderma reesei* using *S. cerevisiae* Sec24p, Sfb3p or Sfb2p amino acid sequences as query sequences reveals that *T. reesei* has a single gene that is most closely homologous to yeast Sec24 and a single gene that is most closely homologous to yeast Sfb3. No other homolog was identified suggesting that *T. reesei* does not have a gene equivalent to Sfb2.

Using BLAST to search publicly available genome sequences of *Pezizomycotina* species using the *T. reesei* Sfb3 amino acid sequence as query demonstrates a general pattern. That is, each fungus has a clear homolog of each of Sfb3 and Sec24 but an additional homolog more closely related to yeast Sfb2 is not present in the genomes of these filamentous ascomycetes.

Homologs of the Sfb3 proteins are found in filamentous fungi, e.g., *Trichoderma reesei* and *Aspergillus oryzae*, although the function of these proteins was heretofore unknown. The amino acid sequences of the *S. cerevisiae* (SEQ ID NO: 1), *T. reesei* (SEQ ID NO: 2), *A. oryzae* (SEQ ID NO: 3), *A. niger* (SEQ ID NO: 4), *P. funiculosum* (SEQ ID NO: 5), *P. chrysogenum* (SEQ ID NO: 6), *N. Crassa* (SEQ ID NO: 7), and *F. oxysporum* (SEQ ID NO: 8) Sfb3proteins are shown, below, as examples: SEQ ID NOs: 4-8 were obtained from publicly-accessible fungal genome databases but do not have accession numbers.

*Saccharomyces cerevisiae* Sfb3 amino acid sequence (SEQ ID NO: 1):
MSQQNILAASVSALSLDESTVHTGGASSKKSRRPHRAYHNFSSGTVPTLGNSPYTTPQLNQQDG

FQQPQAFTPKQFGGFNNGSGSVMSTPVMVSQERFGASEASSPYGQSMLDMTAPQPTSHIVPTQR

FEDQAQYLQRSFETCRDSVPPLPTTQFYCVDQGSCDPHLMSLSMYNIPESEHLRAATKLPLGLT

IQPFSTLTPNDAEVPTIPLPMDGTPLRCRRCRAYANPKFQFTYDSSVICNICRVKMQVPGEHFA

PMGPNGQRSDLNEKSELLHGTVDFLVPSIYNAIQEKELLPLHYVFLIDVSLLANENGSSLAMVE

GVRSCIEYISDFQPNCEVAIIVYDNKLRFFNLRPDLDNAQEYIVSELDDVFLPFYNGLFVKPGN

SMKIINDTLIKISGYISTDKYSHVPQVCYGSALQAAKLALDTVTGGQGGKIICSLNSLPTIGNG

NLSLKRDNAHIAHVKCDNGFYKKLASDFLKSYISLDLYVTNAGFIDMATVGEPVEMTSGILKYY

PHFQQETDAFTLVNDMVTNVSNIVGYQALLKVRCSTGLSVEQYYCDSSDNITHDPIIPVLTRDT

TLDVLLKYDSKIKTGTDVHFQTALLYTDIDGVRKVRSINTSGAVSNNIREIFKFINQNPVMRIM

IKDVIKTLGDCDFVKIRRLIDDKMVEILTQYRGLVSSNSSTQLILPDSIKTLPAYMLAFEKSEL

MKPNAQSTRGNERIYDLLKYDSLNSAQLCYKLYPQIVPFEVLLEETDLTFYDANDKLLQINSSS

INNLSVRASESNFINGGCYLIFQGDTIYLWFNENTNRMLLQDLLSVDESLPVSQISLFSGTLPE

TGTSINQKASNVIKNWQQVVNKSSLPLVLLRPNVDQYYSNVMSQLLCEDKTVNRIESYDNYLVI

MEKKIQEKLQKDDFIKVSTAATHENIEQKFVQF

*Trichoderma reesei* Sfb3 amino acid sequence (SEQ ID NO: 2):
MDYTQYEALGHGEVLDPNDPNKTSAPAAPQFQPPSSPYVPPGSPYGAPPYEGGEQAPPMAMPPP

STPGYGPPQGQSFPGSPMPSQDAGLAAQFGGMSLGADAGGAAARKKKKDRHAYHSVEPTGSSQA

FNGLPPGTPAEQFLNVNNPQGIPALGGQFGSPLASPMGTPHMANPGQFPAPTSPFTPSAPVSPA

EFASRFGSPDAATSIGSAGPSQVSPDDMPSIPASRDAIQEEFFKNVYPTFEREVPPPATVSFVA

FDQGNASPKFTRLTLNNIPTTAEGLHATGLPLGMLIQPLAPLQAGEAEIPVLDFGDAGPPRCRR

CRAYINPFMMFRSGGNKFVCNLCSYPNETPPEYFCAVSPQGVRLDRDQRPELERGTVEFVVPKE

YWTREPVGLRWLFVIDVTQESYNKGFMETFCEGILAALYGGNDEENDEDGEPKRRIPKGAKVGF

ITYDKDIEFYNINPHLDQAEMMIMPDLEDPFLPLGEGLFVDPYESKAIITSLLTRLPEMFSTIK

NPEPALLATLNAAVAALEATGGKVVCSCSTLPTWGPGRLFMRDDGNEPGGELDKKLYTTEEPAW

KKVSEKMASSGIGVDFFLAAPSGGYLDIATIGHVAATTGGETFYYPNFIAPRDGARLSMEITHA

ITRETGFQALMKVRCSTGLQVAAYHGNFVQHTFGADLEIGVIDADKALGVSFSHDGKLDPKLDA

HFQTALLYTTASGQRRVRCSNVIASVSDTSKESNTKELAIRQCLKFVDQDAVVGIFAKEASTKL

ATTSANLQDVRNWLTERTIDIMAYYKKESANQFPPSQLVMPERLKEFCMYMLGMLKCRAFKGGI

ENSDRRVEELRMVRSMGPLELSLYLYPRMIALENLQPEEGFADPETGELKMPPSVRTSFSRVEP

GGVYLVDNGQQCLLWFHAQTSPNLITDLFGEGHDSLKGLDPYTSTLPVLETHLSAQVRNITEFL

KSMRGSKGMTIQLARQGIDGAEYEFARMLVEDRNNEAKSYVDWLVHIHRGVQLELSGQRKKEGD

GEATAVMANFAGLRPAYW

*Aspergillus oryzae* RIB40 Sfb3 amino acid sequence
(GI: 83766074; SEQ ID NO: 3):
MADQSMYNTLGQGTSPAEDPSNPNRMAEQVPPQSQPAAGFPPGPYPPQPGAYYGNPPPNQYDAPA

AAPPTQQLQSPPPRGLAPSPQLAYGTETQTEMGAPADPMAGLASQMSGLGIMGDSGARPGKKKER

HAHHEIGGATASAPQQFAGMPQAGMQPSSQFLNTGLNQAPRPISPAAGVPPAGIVPQPGVPAPGS

GSVPTQGKIDPEQIPSIPQSRDIPTMYYFDEIYPTMERELPPPAAVPFVAHDQGNSSPKHARLTL

NNIPTTSDFLSSTALPLGMVLQPLARLDPGEPEVPVLDFGEMGPPRCRRCRAYINPFMTFRSGGN

KFVCNMCTFPNDVAPEYFAPLDMSGARVDRLQRPELMIGTVEFMVPKEYWNKEPVGLQRLFLIDV

SQESVNRGFLKGVCKGITEALYGAPDASEEDAAARRVPEGSKIGIVTYDREVEFYNLSAQLDQAQ

-continued

```
MMVMTDLEEPFVPLSEGLEVDPYESKDIITSLLERIPKIFSHIKKPEPALLPALNAAMSALQATG

GKIFASICSLPTWGPGALEMRDDPKVEGIDAERKLETTDNQAWRTIAGKMAEEGIGVDMFVAAPG

GTYVDVATIGHVAEVSGGETFFYPNFHAPRDILKLSQEFAHAVTRETGYQAMMKVRCSNGLQVSA

YEGNEIQHALGADLEIGSIDADKAIGVMFSYDGKLDPKLDAHFQAALLYTTAEGQRRVRCINVVA

AVNEGGLETMKFIDQDCVVSIMAKEAAAKTVDKSLKDIRASITEKTVDIFSGYRKVFSGSEPPGQ

LVLPENLKEFSMYMLALIKSRAFKGGQEASDRRIHDMRMLRSIGATELALYLYPRVIPIHNMQPE

DGFPNEQGQLQVPPSLRASFSKIEEGGAYLVDNGQICLLWLESRVSPNLLEDLLGPGQSSLQGLN

PQTSSLPVLETHLNAQVRNLLQYFSIMRGSKSVAIQLARQGLDGAEYEFARLLVEDRNNEAQSYV

DWLVHIHRQINLELAGHRKREDTSAEGSLTSLAGLRAPYW
```

Aspergillus niger Sfb3 amino acid sequence (SEQ ID NO: 4)
```
MADPNMYHTYGQAPVPGENPSDPNQMAYQVPPQGYPAAGIPPGPSPPQPGAAYGVPAPNQQWPA

YGSPPPAQQPLQQPPSQFAHQADPQAAMGAPVDPGMAGLASQMSGLGIMGGEGGAARSSKKKHR

HAHHEIAGASASVAQPFAAAPQDPMQPTSQFLNTGLNQAPRPISPAASIPAPVNPAFGGGAGAV

PTQGKVDPEQIPSIPRSRDLPAQYYFNHVYPTMERHLPPPAAVPFVAHDQGNSSPKYARLTLNN

IPSTSDFLSSTGLPLGMVLQPLARLDGEQPIPVLDFGDAGPPRCRRCRAYINPFMSFRSGGNKF

VCNMCTFPNDVPPEYFAPLDPSGSRIDRMORPELMMGIVEFLVPKDYWNKEPVGLQWLLLIDVS

QESVNKGELKGVCKGIMEALYSEETENPEDEAPARRIPEGAKIGIVTYDKEVHFYNLSAQLDQA

QMMVMTDLEEPFVPLSEGLFVDPYESKDVITSLLQRIPSIFSHVKNPQPALLPALNAALSALRP

TGGKIVGTIASLPTWGPGALSLRDDPKVHGTDAERKLETTEHAGWRETAGHLAEAGIGLDMFIA

APSGTYMDVATIGHIPEVTGGETFFYPNFHAPRDIRKLSKELAHAITRETGYQALMKVRCSNGL

QVSGYHGNEVQHTFGADLEIGAIDADKAIGVVFSYDGKLDPKLDAHFQAALLYISANGQRRVRC

INTVAAVNEGGMETMKFVDQDAVVAMVAKDAASKTLDKSLKDIRAGVSEKTVDIFSGYRKIFSG

SHPPGQLVLPENLKEFSMYMLSLIKSRAIKGGQEASDRRIHDMRMLRSIGCTELSLYLYPRIIP

IHNMQPTDGFPNEQGQLQVPPSLRASFSKIEEGGAYLVDNGQQCLLWLHSHVSPNLLEDLFGEG

QTSLQGLSPQISTIPVLETHLNAQVRNLLQYFSTIRGSKAVTIQLARQGLDGAEYEFARMLVED

RNNEAQSSVDWLVHIHRQINLELAGHRKREDTAGEGGLTSLAGLRAPYW
```

Penicillium funiculosum Sfb3 amino acid sequence (SEQ ID NO: 5)
```
MADYSTYHSSGYAGAPGEDPNRQQPAVPAPYHSPNAPPGQAIQQPGITPYGAAQPPQFPGQPGV

GYGVAPVPSPPQALGGPDVGDLATRIGGLGIISDAGTRSHKKKHRHAYHDIGGPNAQGLNTFPS

QTNLQSQFLNTGLNQPEQQPAAPAAFPGAPVGQVPANVAPGAAPEVGGVGSVPTQGKIDPEQIP

SVPRSRDLPAQYYFNNVYPTMERHVPPPASIPFIAHDQGNSSPKVARLTLNNIPSSSDFLQSTG

LPLGMILQPLAKLDAGEQPVPVIDFGDIGPPRCRRCRTYINPFMTERSGGNKFVCNMCTFPNDV

PPEYFAPVDPSGVRVERLQRPELMLGTVEFTVPKEYWVKEPAGLEOLFLIDVSQESVNRGFLKG

VCDGIINALYGEEEPVEGAEPETRKVPEGSKIGIVTFDREIHFYNLLPRLDKAQMMVMTDLEEP

EVPLSEGLEVDPYESKDVITSLLEQLPSLFARVKSPESTLLPTIKAAISALQAIGGKIICOLTS

LPTYGPGKLVMKDKSQAPDGENKLFAIDNPDYKAAATKLTEAGVGIDFFVAAPGGSFMDLTTIG

YTAAISGGECFFYPNEHSPRDSLKLAQEISHTVTRETGYQALMKVRCSNGLQVSAYYGNFLQHT

FGADLEIGTIDADKALGVLFSYDGKLDPKLDAHFQAALLYTAANGQRRVRCINIVAGVNEGGIE

TMKCIDQDAVVAIIAKEAASKAGDKTLKDIRASITEKTVDIFSGYRKNFSGSHPPGQLVLPENL

KEFSMYMLGLLKSRAFKGGSETADRRVHDLRMLRSIGCLELSLYLYPRIIPIHNMSAEDGFANE

QGQLQVPPALRASFSRVEEGGAYLIDNGQGILLWIHSFVSPNLLEDLFGPGITSLQALDPNTSS
```

-continued

LPVLETHLNAQVRNLLQYLSTVRGSKAVTIQLARQGIDGAEYEFARSLVEDRNNEAQSYVDWLV

HIHRQINLELAGHRKKEDSATSSGEGALSSLAGIRAPYW

*Penicillium chrysogenum* Sfb3 amino acid sequence (SEQ ID NO: 6)
MADSSMYNTMGQGSSEDPSNPQYMAQVPPQQYPAGYPPTAAPLQPGAPYANPAPNQWPAYGSPQ

QPGMASPGIAYNAPQQPMGAAVDPGMAGLASQMGGLDIAADAGARTERKKHRHAHHDIGGGAAP

PAQGFNTGMDQGGLQQPQPQQQSQFLNTGLNQHADRPVSPAVGLVSGQSVAAIPGIQSGAGSVP

TSGRIDPEHIPSIPRSRDLPAQYYFNHVYPTMDQHLPPPAAIPFVAQDQGNSSPKYARLTLNNI

PSASDFLTSTGLPLGMILQPLAPLDPGEQPIPVLDFGDVGPPRCRRCRTYINPFMSFRSGGSKF

VCNMCTFPNDTPPEYFAPLDPSGARVDRMQRPELLMGTVEFTVPKEYWNKEPVGLQTLFLIDVS

RESVHRGFLKGVCAGIKDALYGDDDKASEGTEGDGSSRKLPVGAKVGIVTYDKEVHFYNLAAAL

DQAQMMVMTDLDEPFVPLSEGLFVDPYESKSVITSLLSRIPKIFSSIKNPESALLPTLNSALSA

LQATGGKIVCAVASLPTCGPGHLAIREDPKVHGTDAERKLFTTENPAWKKTASKLAEAGVGLDL

FMAAPGGTYLDVATIGHVSSLIGGETFFYPNFHAPRDLLKLRKEIAEAVTRETGYQTLMKVRCS

NGLQVSAYHGNFVQHTLGADLEIAGVDADKAVGVLFSYDGKLDPKLDAHFQAALLYTSADGQRR

VRCINVVAAVNEGGLETMKFVDQDAVVSVIAKEAASKILDKNLKDIRASISEKTVDIFSGYRKI

FSGSHPPGQLVLPENLKEFSMYMLSLVKSRAFKAGPESSDRRIHDMRLIRSMGCTEMALYLYPR

IIPVHNMQPEDGFANEHGQLQIPPTMRASYSRIEDGGVYIVDNGQAILLWTHAQVSPNLLEDLF

GPGHNSLQGLNPNTSSLPVLETHLNAQVRNLLQYLSTVRGSKSVTIQLARQGLDGAEYEFARLL

LEDRNNEAQSYVDWLVHIHRQINLELAGHRKKEEGGEGALASLSAMRTPYW

*Neurospora crassa* Sfb3 amino acid sequence (SEQ ID NO: 7)
MADYTMYHALGQGETLDPNDPNRTTQPAPPQFQPPVAPNPYHPGAEYNAPGQQQQQQQQQYGQQY

GQQYGQQYGQQQYGQEYGHQQQQQQQQQYGAPSPYGAPPAHSPVSPMDDVGLAAQMGGMSLGAG

AGAADHHGRKKKKDRHAFHTVEAPAGSSQPFNGMPPAGIPATQFLNADPSLAGRIPGPGHGQFP

MPASPAFGPVPTSAADFAARDATQGVGSGVFAAGGPQGGKPSPDDTPSVPLSRDAVQPYFHTNV

YPTFERLVPPPAVTSEVALDQGNSSPKFARLTMTNLPASAEGLKSTGLPLGLLLQPLAETQPGE

LPIPVLDFGEQGPPRCHRCRAYMNPFMMFKAGGNKFVCNLCTYANDTPPEYFCALSPQGVRVDR

DQRPELTRGTVEFVVPKEYWTKEPVGMRYLFVIDVTQESYNKGFLESFCEGILSALYGGSEEGE

DQDETGEPKRKIPAGAKVGFVTFDQEIHFYNVSPALEQAQMIVMPDIEDPFLPLSDGLFVDPYE

SKAVISSLLTRLPQMFSNIKNPEPALLSALNSAVAALEKTGGKVFCSLAALPTWGPGRLFMRDD

GKHPGGEPDKKLFTTEHPGWRKLAEKMVSLGVGADFEMASPSGGYLDIATIGHVSSTTGGETFF

YPNFVVQRDSTKLSLEIHHAVRRETGYAALMKVRCSNGLQVNAYHGNFIQHTFGADLEIGVIDA

DKALAVTFGYDGKLDSKLDAHFQAALLYTTASGQRRVRCINVIAGVSDLARDCMKYIDQDAIVS

ILAKEASTKLSTTSANLKEVRSSLTEKTIDILALYRKNHLAVPHPPQQLVMPERLKEFTMYVLG

MLKCRAFKGGNETTDRRVHDMRLIRSMGARELSLYLYPRIIPLHSLQPEDGYPDATTGHLRMPS

TMRASFARVEPGGVYLVDNGQVCLLWMHAQTAPALIQDLFGEDKTTLQSLDPYISTIPVLETHL

NAQTRNITEYMRTVRGSKGLTIQLARQGIDGAEFEFARMLVEDRNNEAQSYVDWLVEVHKGVQL

ELAGQRKREDGESHSALGSFTGLRPAYW

*Fusarium ausporwn* Sfb3 amino acid sequence (SEQ ID NO

-continued

```
NSSPKYTRLTLNNIPTTQDALQATGLSLGLLLQPLAPLQAGEAEIPVLDFGEAGPPRCRRCRAY

MNPFMMFRSGGNKFVCNLCAYPNDTPPEYFSATNPQGVRVDRDTRPELHRGTVEFVVPKEYWTR

EPVGLRWLFLIDVTQESYNKGYVEAFCEGIRVALYGGEDQELDENGEPKRRIPEGAKVGFVTYD

KDTHEYNVNPALDQAQMMIMPDLEDPFVPLSEGLFVDPYESKDVITSLLTRLPDMFSTIKNPEP

ALLAALNSALAALEATGGKVVASCSALPTWGPGRLFMRDNGNHPGGEIDKKLYTTEEPAWKKVA

EKMAASGVGADFFLAAPSGGYLDIATIGHVSSTTGGEIFYYPNEIAARDSRKLSLEISHAVTRE

TGFQALMKVRCSNGLQVSGYHGNFIQHTFGADLEIGVIDADKAMGVSFSYDGKLDPKLDAHFQS

ALLYTTASGERRVRCSNVIASVTETSKESGAREQGIRECLKFVDQDAVIGMLAKEASTKLATTS

SNLKDIRHWLSEKAIDVLACYRKHAAQQHPPGQLVMPERLKEYCMYLLGLLKCRALKGGVENSD

RRVHEMRMLRSMGALELSLYLYPRMIPIHNLAPEEGFADPETGHLKMPPAIRTSFSRVEPGGVY

LVDNGQQCLLWFHSQTSPNLISDLFGEDKDSLKSLDPYTSALPLLETHLNAQVRNIIEFLRTMR

GSKGLTIQLARQGIDGAEEDFARMLVEDRNNEAQSYVDWLVHIHKGVQLELSGQRKKEGEEHTA

ASLSNFAGLRPAYW
```

An alignment of the amino acid sequences of the Sfb3 proteins from *S. cerevisiae* (SEQ ID NO: 1) and *T. reesei* (SEQ ID NO: 2) is shown in FIG. 13. These sequences have approximately 30% amino acid sequence identity. By contrast, the Sfb3 proteins from *T. reesei* and *A. oryzae* have approximately 58% amino acid sequence identity. An alignment of the amino acid sequences of the Sfb3proteins from *S. cerevisiae* (SEQ ID NO: 1), *T. reesei* (SEQ ID NO: 2), and *A. oryzae* (SEQ ID NO: 3) is shown in FIG. 14.

An alignment of the amino acid sequences of the Sfb3 proteins from approximately 40 so *Pezizomycotina* species revealed a specific amino acid sequence, i.e., IQLARQGXDGXEXXXARXLXEDRNXEAXSXVDWL (SEQ ID NO: 9, where X is any amino acid residue), which is close to the C-terminus of the Sfb3 proteins, and not found in Sec24 proteins. This consensus sequence can be used to identify Sfb3 proteins in other members of the *Pezizomycotina*.

Separate studies have shown that mutation of the gas1 gene (or the gel1 gene as it is known in *Aspergillus fumigatus*) affects fungal cell wall structure and leads to morphological changes as well as hypersensitivity to Calcofluor White, Congo Red and sodium dodecyl sulfate.

Without being limited to a theory, it is believed that the alteration of Sfb3 expression and/or activity in filamentous fungi interferes with the transport of proteins involved in cell wall synthesis, thereby altering cell wall structure and producing a more compact cellular morphology characterized by shorter hyphae and a more yeast-like appearance. A likely candidate for a protein involved in cell wall synthesis is Gas1/Gel1.

Variant filamentous fungi strains that exhibit an altered viscosity phenotype in liquid medium can be well suited for the large scale production of commercially important proteins. While the present strains and methods are exemplified using the filamentous fungus *T. reesei*, the function of the Sfb3 protein within the *Pezizomycotina* is expected to be conserved. Therefore the present strains and methods are in no way limited to *T. reesei*.

V. Filamentous Fungal Strain with Altered Sfb3 Protein Production

In one aspect, a variant strain of filamentous fungus derived from a parental strain is provided, the variant strain comprising a genetic alteration that causes cells of the variant strain to produce an altered amount of functional Sfb3 protein compared to cells of the parental strain. The cells of the variant strain subsequently produce, during aerobic fermentation in submerged culture, a cell broth that requires an altered amount of agitation to maintain a preselected dissolved oxygen content, or a cell mass that maintains an altered dissolved oxygen content at a preselected amount of agitation, compared to the cells of the parental strain.

In some cases, the genetic alteration causes cells of the variant strain to produce a reduced amount of functional Sfb3 protein compared to cells of the parental strain, and the resulting cell broth requires reduced agitation to maintain a preselected dissolved oxygen content, or maintains a higher dissolved oxygen content at a preselected amount of agitation, compared to the cells of the parental strain. In such cases, it is believed that the cell mass of the variant strain exhibits reduced viscosity compared to a cell mass of the parental strain, which accounts for the observations relating to dissolved oxygen content and agitation.

The reduction in the amount of functional Sfb3 protein may result from disruption of the sfb3 gene present in the parental strain. Because disruption of the sfb3 gene is a primary genetic determinant for conferring a reduced viscosity phenotype to the variant strain, such variant strains need only comprise a disrupted sfb3 gene, while all other genes may remain intact. In some cases, the variant strains may optionally include additional genetic alterations compared to the parental stain from which they are derived. Such additional genetic alterations are not necessary to confer a reduction in viscosity but may confer other advantageous to the strain.

Disruption of the sfb3 gene can be performed using any suitable methods that substantially prevent expression of a function sfb3 gene product, i.e., the Sfb3 protein. Exemplary methods of disruption include complete or partial deletion of the sfb3 gene, including complete or partial deletion of, e.g., the Sfb3-coding sequence, the promoter, the terminator, an enhancer, or another regulatory element. Disruption of the sfb3 gene can also be performed by the complete or partial deletion of a portion of the chromosome that includes any portion of the sfb3 gene. Particular methods of disrupting the sfb3 gene include making nucleotide substitutions or insertions in any portion of the sfb3 gene, e.g., the Sfb3-coding sequence, the promoter, the terminator, an enhancer, or another regulatory element. Preferably, deletions, insertions, and/or substitutions (collectively referred to as mutations) are made by genetic manipulation using sequence-specific molecular biology techniques, as opposed to by chemical mutagenesis, which is generally not targeted to specific nucleic acid sequences.

Mutations in the sfb3 gene may reduce the efficiency of the sfb3 promoter, reduce the efficiency of a sfb3 enhancer, interfere with the splicing or editing of the sfb3 mRNA, interfere with the translation of the sfb3 mRNA, introduce a stop codon into the Sfb3-coding sequence to prevent the translation of full-length Sfb3 protein, change the coding sequence of the Sfb3 protein to produce a less active or inactive protein or reduce Sfb3 interaction with other cell wall components, change the coding sequence of the Sfb3 protein to produce a less stable protein or target the protein for destruction, cause the Sfb3 protein to misfold or be incorrectly modified (e.g., by glycosylation), or interfere with cellular trafficking of the Sfb3 protein.

Generally, the goal of these and other genetic manipulations is to reduce or prevent the expression of a functional Sfb3 protein, or reduce or prevent the normal biological activity of the Sfb3 protein, thereby producing a morphology change that results in a reduced viscosity phenotype.

In other cases, the genetic alteration increases or restores the expression of a functional Sfb3 protein, or increases the normal biological activity of the Sfb3 protein, thereby producing a morphology change that results in an increased or restored viscosity phenotype. Exemplary genetic alterations that increase or restore Sfb3 function are those that introduce addition copies of the sfb3 gene into a cell, increase the efficiency of the sfb3 promoter, enhancer, or other control element, increase the translation of the mRNA encoding the Sfb3 protein, increase the stability of mRNA encoding the Sfb3 protein, introduce changes in the sfb3 gene that increase the activity or stability of the Sfb3 protein, introduce changes in the sfb3 gene that modulate the interaction with other proteins or cell wall components, and the like. Other genetic alterations that increase or restore Sfb3 function are those that reverse the effect of genetic alterations that reduce or prevent the expression of a functional Sfb3 protein Filamentous fungus cells for manipulation and use as described are generally from the phylum *Ascomycota*, subphylum *Pezizomycotina*, particularly fungi that have a vegetative hyphae state and include a homolog of the sfb3 gene. Such organisms include filamentous fungus cells used for the production of commercially important industrial and pharmaceutical proteins, including, but are not limited to *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., *Myceliophthora* spp., and *Neurospora* spp. Particular organisms include, but are not limited to, *Trichoderma reesei* (previously classified as *Trichoderma longibrachiatum* and *Hypocrea jecorina*), *Aspergillus niger, Aspergillus fumigatus, Aspergillus itaconicus, Aspergillus oryzae, Aspergillus nidulans, Aspergillus terreus, Aspergillus sojae, Aspergillus japonicus, Scedosporium prolificans, Neurospora crassa, Penicillium funiculosum, Penicillium chrysogenum, Talaromyces* (*Geosmithia*) *emersonii, Fusarium venenatwn, Myceliophthora thermophila*, and *Chrysosporium lucknowense*.

In some embodiments, e.g., where the filamentous fungus is *T. reesei*, the sfb3 gene encodes a protein having the amino acid sequence of SEQ ID NO: 2. In other embodiments, the sfb3 gene encodes a protein having a specified degree of overall amino acid sequence identity to the amino acid sequence of SEQ ID NO: 2, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity.

In some embodiments, e.g., where the filamentous fungus is *A. oryzae*, the sfb3 gene encodes a protein having the amino acid sequence of SEQ ID NO: 3. In other embodiments, the sfb3 gene encodes a protein having a specified degree of overall amino acid sequence identity to the amino acid sequence of SEQ ID NO: 3, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity.

In some embodiments, e.g., where the filamentous fungus is *T. reesei*, the sfb3 gene has the nucleotide sequence of SEQ ID NO: 10 shown, below. In other embodiments, the sfb3 gene has a nucleotide sequence with a specified degree of overall nucleotide sequence identity to the nucleotide sequence of SEQ ID NO: 10, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity.

*Trichoderma reesei* sfb3 DNA sequence
(SEQ ID NO: 10; 2 introns are underlined):

```
atggactacacgcagtatcacgccctgggccacggcgaggtcctcgaccccaacgaccccaaca agacgtccgctccagcggctccccagttccagcccccctcctcgccctacgtgccaccgggctc cccttacggcgctcccccgtaccatggcggccaccaagctcctcccatggcaatgccgcctccg tcgacgcccggctacggcccgccgcagggccagagcttccccgggtctccgatgccgtcgcagg atgctggccttgccgcgcagtttggcgggatgagcctgggtgcggatgcgggaggcgccgccgc gaggaagaagaagaaggacaggcacgcgtaccacagcgtggagccgacgggctcgtcgcaggcc ttcaatggcctgccgccggggacgcccgccgagcagttcctcaacgtcaacaacccgcagggca tcccggcgctgggagggcagtttggaagccctctggccagccccatgggcacgcctcacatggc caatccgggccagttcccggcgccaacctctcccttcacccccctcggcccctgtgtcgccggcc
```

-continued

```
gagttcgcatccaggtttggctctcccgacgctgccacgtcaataggctcggctggccccagcc
aggtgtcgccagacgacatgcccagcatacccgcctcgagggacgccatccaggagcactttt
taagaacgtttacccgaccttcgagcgccatgtgcccctcctgcgacggtttcctttgttgcc
ttcgaccaaggcaatgcctctcccaaattcacccgactcaccctcaacaacatcccaaccacag
ccgagggcctccatgcgacgggcttgcccctgggcatgctcatccagcctctggccccacttca
agcgggagaggccgagattcccgttctcgactttggcgacgccggcccgcctcgatgtcgaaga
tgccgggcttatatcaacccctcatgatgttccgatcgggcggcaacaagttcgtgtgcaacc
tctgctcgtaccccaacgaaacgccgcccgagtactttgcgccgtcagcccacagggagtgcg
cctagatcgagaccagcggccggagcttcaccgcggtaccgtcgagttcgtcgtccccaaggag
tactggacccgagagcccgtcggcctccgctggctgtttgtcatcgacgtcacgcaggaatcct
ataacaagggcttcatggagacattctgcgagggcatcctcgcggccctctacggcggcaacga
cgaggagaatgatgaagatggcgagccaaagcgaaggatacccaagggagccaaggttgggttc
atcacgtacgacaaggacattcacttttacaacatcaacgtgagttcacgagcactgggaacaa
gaatgagatggcccgctaacattaagacagcctcatctggatcaagcgcacatgatgatcatgc
ccgacctcgaagacccattcctcccctcggcgagggcctctttgtcgacccgtacgagtcaaa
ggccatcatcacctctctcctcacccgcctccccgagatgttctccaccatcaaaaaccccgag
cccgctctgcttgccacgctcaatgccgccgtggctgcgctggaggcaacgggaggtaaagtcg
tgtgctcgtgctcgaccttgcctacctggggccctggccgactgttcatgcgcgacgacggcaa
ccatcccggtggcgagctggacaagaagctgtatacgacggaacaccccgcgtggaagaaggtc
tcggagaagatggcttcgtccggcattggtgtcgacttcttccttgctgcgccctccggcggct
acctggacattgcgacgataggccatgtcgccgccacgactggtggagagacgttctactaccc
caacttcatcgccccgcgagacggtgcccggctgtcaatggagattacgcacgccatcacgagg
gaaacgggcttccaggcgctgatgaaggtccgctgctcgaccgggctgcaggtggcggcgtacc
acggcaactttgtccagcacacctttggggcagacctggagattggcgtcattgacgcggacaa
ggcgctcggcgtgtcgtttagccacgacggtaaactggatcccaagctggacgcccacttccag
acggctctcctgtacacgaccgcgtccggacagcgacgcgtgcgatgttccaacgtgattgcca
gcgtcagcgacacctccaaggagtccaacaccaaggagctggccattcggcagtgcctcaagtt
tgtcgaccaggacgcggttgtgggtatctttgcaaaagaagccagcaccaagctcgccacgaca
tcggccaatctccaggatgtgcgaaactggctgacggagcgaacaatcgacatcatggcctact
acaagaagcactctgccaatcagttccctccgagccagctggtcatgcccgaacggctgaagga
gttctgcatgtacatgctaggcatgttgaaatgcagagctttcaagggcggtatcgagaactcg
gatcgcagagtgcacgagctgcgcatggtccgcagcatgggcccgctggagcttagcctgtatc
tgtaccccggatgattgctctgcacaacctccagcccgaagagggctttgccgaccccgaaac
aggccacctcaagatgcccccgtccgtgcggacgtccttttcacgggtcgagccgggtggcgtc
tacctggtggacaacgacagcagtgcttgctgtggtttcacgcccagacgtcgcccaacctca
tcaccgacctgtttggcgagggccacgactcgctcaaggggctggatccgtacacgtccacgct
gccggtgctggagacgcatctcagcgcacaggtccgcaacattattgagttcctcaaaagcatg
agggatccaagggcatgacgatacagctggcgcggcaggggattgacggcgccgagtacgagt
ttgcgcggatgttggtggaggatcgcaacaatgaggcgaagagctacgttgactggcttgttca
cattcacagaggagttcagctggaggtatgttccccgcctcccccttttccccttgcgtcg
```

-continued
```
tcgtcaggagatgatgagaatgctaattcgtcctatagttgagcggacaacgaaagaaggaagg cgatggagaggctaccgccgtaatggccaactttgcaggactgagaccggcctattggtag
```

VI. Method for Altering the Viscosity Phenotype of Filamentous Fungal Cells

In another aspect, a method for altering the morphology of filamentous fungus cells is provided. The variant filamentous fungus cells exhibit altered growth morphology on solid medium and produce cell masses having different viscosities when grown in submerged culture.

In some cases, the method comprises disrupting the sfb3gene in a parental strain using suitable genetic or chemical methods, wherein during aerobic fermentation the variant strain produces during aerobic fermentation in submerged culture a cell broth that requires reduced agitation to maintain a preselected dissolved oxygen content, or maintains an increased dissolved oxygen content at a preselected amount of agitation, compared to the cells of the parental strain. Such methods may be used to disrupt the sfb3gene in any manner described above and elsewhere. Preferably, disruption of the sfb3gene is performed by genetic manipulation using sequence-specific molecular biology techniques, as opposed to chemical mutagenesis, which is generally not targeted to specific nucleic acid sequences.

In some embodiments, the parental strain into which the reduced viscosity phenotype is introduced already comprises a gene of interest intended to be expressed at high levels. In this manner, the present methods obviate the need to introduce a gene of interest into a pre-existing reduced viscosity strain for production. Thus, the present methods can be used to produce a reduced viscosity variant strain of filamentous fungus cells from a parental strain already comprising a gene of interest.

In another aspect, a method for screening filamentous fungus cells for an altered viscosity phenotype is also provided. The method involves screening a panel of filamentous fungus cells (e.g., mutagenized cells or field isolates) for altered sensitivity to a fluorochrome stain, wherein altered sensitivity to the fluorochrome stain indicates that the variant cells produce during aerobic fermentation in submerged culture a cell broth that requires more or less agitation to maintain a preselected dissolved oxygen content, and/or maintain an increased or decreased dissolved oxygen content at a preselected amount of agitation, compared to the cells of the parental strain. In this manner sensitivity to the fluorochrome stain can be used to identify variant filamentous fungus cells that have an altered viscosity phenotype. In some cases, the method involves screening a panel of filamentous fungus cells (e.g., mutagenized cells or field isolates) for increased sensitivity to a fluorochrome stain, wherein increased sensitivity to the fluorochrome stain indicates that the variant cells produce during aerobic fermentation in submerged culture a cell broth that requires reduced agitation to maintain a preselected dissolved oxygen content, and/or maintain an increased dissolved oxygen content at a preselected amount of agitation, compared to the cells of the parental strain. In this manner sensitivity to the fluorochrome stain can be used to identify variant filamentous fungus cells that have a reduced viscosity phenotype.

Exemplary fluorochromes bind to cellulose and/or chitin in the cell walls of filamentous fungi, and include but are not limited to, Calcofluor white (CAS No. 4193-55-9), Congo red (CAS No. 573-58-0), Solophenyl Flavine (CAS No. 61725-08-4), Pontamine Fast Scarlet (CAS No. 79770-29-9), and primulin (CAS No. 30113-37-2).

The particular genetic technique used to disrupt the sfb3 gene in a parental strain of filamentous fungus is generally not critical to the method, so long as the technique targets the sfb3 gene in a sequence-specific manner. Exemplary methods are site specific recombination, targeted gene insertion, the use of transposable elements, transduction by viruses, and the use of RNA-mediated gene silencing (Raponi M. and Arndt, G. M. (2003) *Nucleic Acids Research* 31:4481-891 Nakayashiki H. and Nguyen, Q. B. (2008) *Current Opinion in Microbiology* 11:494-502; Kuck, U. and Hoff, B. (2010) *Applied and Environmental Biotechnology* 86:51-62), Where desired, disrupting the sfb3gene may be accompanied by the simultaneous or sequential insertion of, e.g., a selectable marker, a fluorescent or other distinguishable marker, a cloning site or cloning cassette, a sequence fingerprint to allow subsequent identification of the strain, or other genetic modification to add distinctiveness or functionality to the strain. In some cases, it may be desirable to introduce a gene of interest intended for high level expression in the reduced viscosity strain at the site of disruption of the sfb3gene. In such cases, introducing the reduced viscosity phenotype and introducing a gene of interest may be performed simultaneously.

VII. Utility

The use of reduced viscosity strains of filamentous fungi is known to improve the distribution of oxygen and nutrients in a submerged culture, reduce the amount of energy required to agitate a submerged culture, and increase the cell mass present in the culture, leading to increased protein production. However, the present variant strains of filamentous fungus offer significant advantages over previously-described reduced viscosity strains.

First, the present strains may have a fully defined genome, making them well-suited for subsequent genetic manipulation, complementation, mating, and the like. Second, the present strains are not adversely affected in secreted protein production. Third, reduced viscosity strains can be produced from essentially any parental strain, including parental strains that already produce a protein intended for high level expression (i.e., a protein of interest), already encode a selectable marker, or already include other features that are desirable in a production host. Thus, the present strain and methods eliminate the need to transfer a gene encoding a protein of interest into a preexisting reduced viscosity production strain.

The present strains and methods find use in the production of commercially important protein in submerged cultures of filamentous fungi. Commercially important proteins include, for example, cellulases, xylanases, pectinases, lyases, pectinases, proteases, amylases, pullulanases, lipases, esterases, perhydrolases, transferases, laccases, catalases, oxidases, reductases, hydrophobin, and other enzymes and non-enzyme proteins capable of being expressed in filamentous fungi. Such proteins may be for industrial or pharmaceutical use.

These and other aspects and embodiments of the present strains and methods will be apparent to the skilled person in view of the present description. The following examples are intended to further illustrate, but not limit, the strains and methods.

EXAMPLES

To assist in reading the following examples, the common names, Genencor strain collection numbers (GICC#), and selected features of the starting filamentous fungus strains are listed in Table 1. The same information for the filamentous fungus strains generated is listed in Table 2. The nucleic acid primers used in the examples are listed in Table 3. Sequences in small caps are nucleotides added to allow direct digestion of the PCR amplified fragment. Sequences in italics are restriction enzyme recognition sites. Sequences in bold are loxP sites. Underlined CACC sequences were added to appropriate primers to allow incorporation of the amplified DNA fragment into a GATEWAY entry vector.

TABLE 1

Pre-existing *Trichoderma reesei* strains used in the Examples.

| Common strain name | GICC# | Selected strain features |
|---|---|---|
| Morph1 1.1 pyr+ (Morph) | 20000150 | Deleted cbhI, cbhII, egII and egIII genes; sometimes referred to as "Quad-delete" |
| Morph TrglaA (29-9) | 20002595 | Morph with two TrglaA::amdS cassettes integrated in tandem |
| 70H2 | 20002047 | 29-9 with an allele of sfb3 (at the sfb3 locus) that produces a truncated Sfb3 protein |
| H3A | 20003243 | "Quad-delete" strain expressing a number of hemicellulases from *Fusarium verticillioides* |

TABLE 2

*Trichoderma reesei* strains generated in this study

| Common strain name | GICC# | Selected strain features |
|---|---|---|
| Morph Δsfb3 #230-2 | 20004084 | Morph with a Δsfb3 deletion cassette at the sfb3 locus |
| Morph TrglaA Δsfb3 #656-2 | 20004085 | 29-9 with a Δsfb3 deletion cassette at the sfb3 locus |
| Morph Δsfb3 TrGA A | 20004164 | Morph Δsfb3 #230-2 with integrated TrglaA::amdS cassettes |
| 70H2 sfb3 #24 | 20004090 | 70H2 with homologous integration of the wild type sfb3 gene at the sfb3 locus |
| H3A Δsfb3 #1009 | 20004902 | H3A with a Δsfb3 deletion cassette at the sfb3 locus |

TABLE 3

Primer sequences used in the Examples.

| Primer name | Nucleotide sequence (5' to 3') | SEQ ID NO |
|---|---|---|
| AVG88 | caca*GTCGAC*CAGCTGGACTGACTGTGCCC | 11 |
| AVG89 | gaga*AGATCT*GAGGAGGCTCTCGCAGGAGA | 12 |
| AVG90 | gaa*AGATCT*ACAGATAACTTCGTATAGCATACATTATACGAAGTTATCCTGGGCTTGTGACTGGTCGCGA | 13 |
| AVG91 | gcaa*GCGGCCGC*aagtATAACTTCGTATAATGTATGCTATACGAAGTTATCGGCCGGCGTATTGGGTGTTACG | 14 |
| AVG92 | gaga*GCGGCCGC*GGGCGTCAATGGCAGAGG | 15 |
| AVG93 | ttaa*TCTAGA*CGTGTTGTGCGGAGAGGC | 16 |
| AVG104 | CAGCTGGACTGACTGTGCC | 17 |
| AVG105 | AGAGGCCCATGCTGTTGG | 18 |
| AVG108 | TTCCTCCGTTCTCCCTGA | 19 |
| AVG109 | GCGGTGAGTTCAGGCTTT | 20 |
| AVG110 | AAATTCCGTCACCAGCCC | 21 |
| AVG111 | CTTGCGTTGGCTCACAGA | 22 |
| SK745 | GAGTGGTGAAGTCGGTAATCC | 23 |
| SK746 | CTGGAAACGCAACCCTGAAG | 24 |
| AVG82 | <u>CACC</u>CCGATAGAAGGCACAGCAACGCTT | 25 |
| AVG83 | GTGATGGAAGCAATGTAGTCCGCAG | 26 |
| AVG84 | <u>CACC</u>ATGGACTACACGCAGTATCACGCC | 27 |
| AVG85 | CTACCAATAGGCCGGTCTCAGTCCT | 28 |
| AVG94 | gaga*ACTAGT*ACCCGACTCACCCTCAACAA | 29 |
| AVG95 | gaga*AGATCT*AGTGTGGTGTGATTGTCCCG | 30 |
| AVG96 | aatt*GCGGCCGC*TGCCTAGGTATGGATTTACTCC | 31 |
| AVG97 | gtgt*TCTAGA*CGATTATGTCGTGAGCCTCTA | 32 |
| AVG102 | CCGACTCACCCTCAACAAC | 33 |
| AVG103 | CGATTATGTCGTGAGCCTCT | 34 |

TABLE 3-continued

Primer sequences used in the Examples.

| Primer name | Nucleotide sequence (5' to 3') | SEQ ID NO |
|---|---|---|
| AVG112 | TCAATAGGCTCGGCTGGC | 35 |
| AVG113 | CCACGGCGAAGAATCCAC | 36 |
| AVG114 | CTCCGGCGAAGCAGAAGA | 37 |
| AVG115 | TCATGCTGTGTCCTGCCG | 38 |
| AVG160 | GCCTCTCCCAAATTCACC | 39 |
| AVG161 | TGGTGGAGAACATCTCGG | 40 |

Media and other stock solutions used in the Examples are described, below:

| VOGEL'S MINIMAL MEDIUM (VM) 1 L | |
|---|---|
| 50x Vogel's Solution | 20 mL |
| 50% Glucose | 20 mL |
| Add dH$_2$O to final volume | |
| Agar | 20 g |
| Autoclave | |

| 50x VOGELS SOLUTION | |
|---|---|
| Sodium Citrate•2H$_2$O | 125 g |
| KH$_2$PO$_4$ (Anhydrous) | 250 g |
| NH$_4$NO$_3$ | 100 g |
| MgSO$_4$•7H$_2$O | 10 g |
| CaCl$_2$•2H$_2$O | 5 g |
| Vogel's Trace Element Solution | 5 mL |
| Vogel's Biotin Solution | 2.5 mL |
| Add dH$_2$O to final volume | |
| Filter sterilize | |

| VOGEL'S TRACE ELEMENT SOLUTION | |
|---|---|
| Citric Acid | 50 g |
| ZnSO$_4$•7H$_2$O | 50 g |
| Fe(NH$_4$)$_2$SO$_4$•6H$_2$O | 10 g |
| CuSO$_4$•5H$_2$O | 2.5 g |
| MnSO$_4$•4H$_2$O | 0.5 g |
| H$_3$BO$_3$ | 0.5 g |
| Na$_2$MoO$_4$•2H$_2$O | 0.5 g |
| Add dH$_2$O to final volume | |
| Filter sterilize | |

| VOGEL'S BIOTIN SOLUTION 1 L | |
|---|---|
| D-Biotin | 0.1 g |
| Filter sterilize | |

| VM HYGROMYCIN MEDIUM (VMH) 1 L | |
|---|---|
| 50x Vogel's Solution | 20 mL |
| 50% Glucose | 20 mL |
| Add dH$_2$O to final volume | |

| VM HYGROMYCIN MEDIUM (VMH) 1 L | |
|---|---|
| Agar | 20 g |
| Autoclave | |

| VM SORBITOL HYGROMYCIN MEDIUM (VMSH) 1 L | |
|---|---|
| 50x Vogel's Solution | 20 mL |
| 50% Glucose | 20 mL |
| Sorbitol | 218.64 g |
| Add dH$_2$O to final volume | |
| Agar | 20 g |
| Autoclave | |
| Hygromycin B (50 mg/mL stock) | 1 mL |

| POTATO DEXTROSE AGAR (PDA) 1 L | |
|---|---|
| BD Difco Potato Dextrose Agar | 39 g |
| Add dH$_2$O to final volume | |
| Autoclave | |

| CONGO RED MEDIUM (CR) 1 L | |
|---|---|
| Make VM or PDA | |
| Autoclave | |
| 1% Congo Red stock | 6 mL |

| 1% CONGO RED STOCK 25 mL | |
|---|---|
| Congo Red | 250 mg |
| dH$_2$O | 25 mL |
| Filter sterilize | |

| YEG MEDIUM 1 L | |
|---|---|
| Yeast Extract | 5 g |
| Glucose | 20 g |
| Add dH$_2$O to final volume | |
| Autoclave | |

| *T. reesei* GLYCINE MINIMAL MEDIUM 1 L | |
|---|---|
| Glycine | 6 g |
| (NH$_4$)$_2$SO$_4$ | 4.7 g |
| KH$_2$PO$_4$ | 5 g |
| MgSO$_4$•7H$_2$O | 1 g |
| 100 mg/mL CaCl$_2$*2H$_2$O solution | 10 mL |
| *T. reesei* Trace Elements 400X | 2.5 mL |
| PIPPS | 33 g |
| Adjust pH to 5.50 with 50% NaOH | (about 5 mL per liter). |
| Add dH$_2$O to final volume | |
| Autoclave. | |
| Add Glucose/Sophorose | 25 mL |

| T. reesei TRACE ELEMENTS 400x 1 L | |
| --- | --- |
| Citric Acid (Anhydrous) | 175 g |
| FeSO$_4$•7H2O | 200 g |
| ZnSO$_4$•7H2O | 16 g |
| CuSO$_4$•5H2O | 3.2 g |
| MnSO$_4$•H2O | 1.4 g |
| H$_3$BO$_3$ (Boric Acid) | 0.8 g |

Example 1. Deletion of Sfb3 from *T. reesei* Strains Morph and 29-9 to Obtain a Reduced Viscosity Phenotype 1.1. Generation of a Δsfb3 Deletion Cassette The DNA sequences flanking the 5' end of the *T. reesei* sfb3 gene was amplified with the primer pair AVG88/AVG89. Amplification of the fragment with this primer pair introduced a SalI site at the 5' end of the fragment and a BglII site at the 3' end of the fragment. The hygromycin B resistance cassette flanked by parallel loxP sites was amplified from plasmid pCR-Blunt II-hph-loxP#4 (FIG. 1) with primer pair AVG90/AVG91, introducing a BglII site at the 5' end of the fragment and a NotI site at the 3' end of the fragment. The DNA sequence flanking the 3' end of sfb3 was amplified with primer pair AVG92/AVG93, introducing a NotI site at the 5' end and an XbaI site at the 3' end of the fragment.

Figure 2:
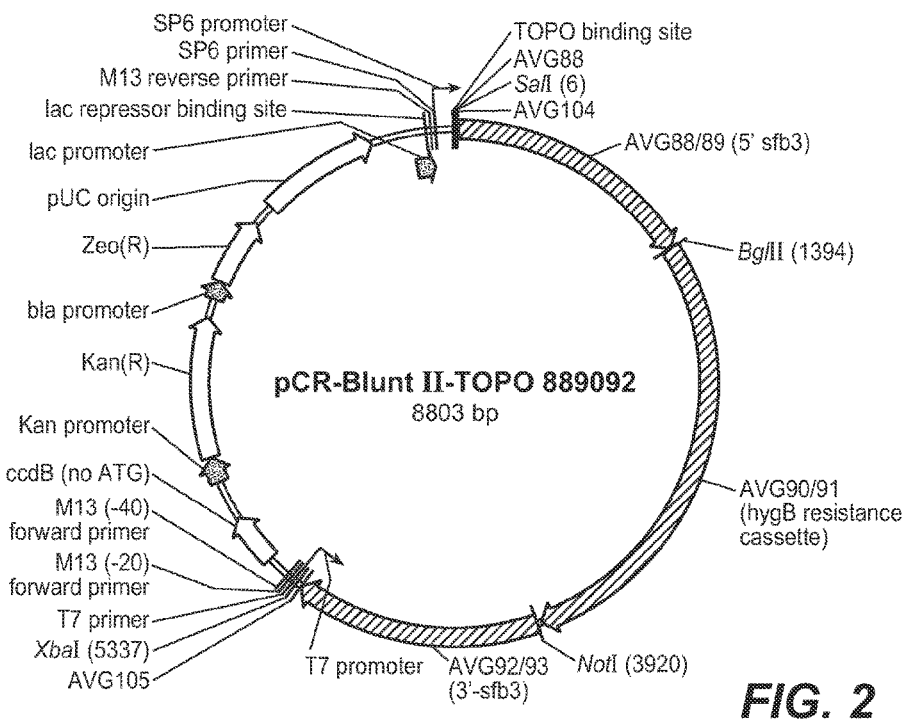
FIG. 2 is map of plasmid pCR-Blunt II-TOPO 889092.
Figure 3A:
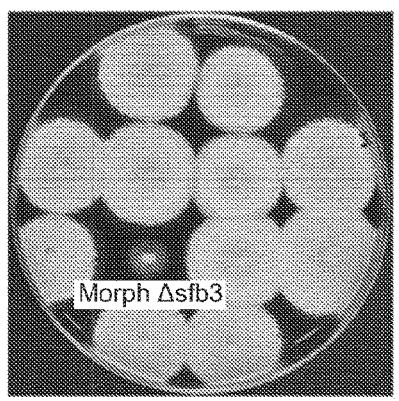
FIG. 3, panels A-D are images of culture plates showing the colony morphology of *T. reesei* strains MorphΔsfb3 and 29-9Δsfb3 on Congo Red-containing medium. (A) Subset of MorphΔsfb3 candidates and (B) corresponding controls. (C) Subset of 29-9Δsfb3 candidates and (D) corresponding controls.
Figure 3B:
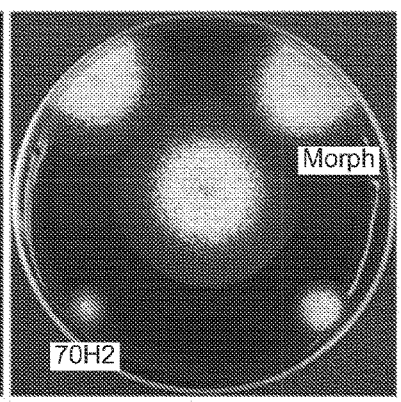
Figure 3C:
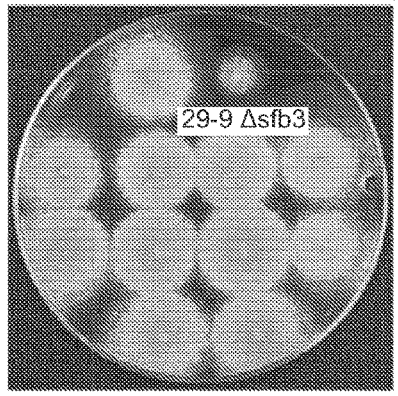
Figure 3D:
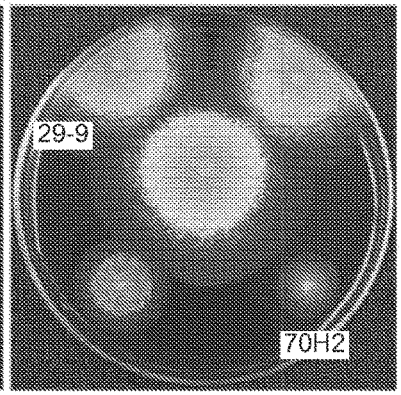

The above three fragments were successively ligated into vector pCR®-BLunt II-TOPO® (Invitrogen Corp., Carlsbad, Calif., USA), and the resulting plasmid was named pCR-Blunt II-TOPO 889092 (FIG. 2). The DNA sequences at the 5' and 3' flanks of the sfb3 gene were amplified using Morph TrglaA (29-9) genomic DNA as the template. The Δsfb3 deletion cassette containing the 5' sfb3 flank, the hygromycin B-resistance cassette surrounded by loxP sites at each end, and the 3' sfb3 flank, was amplified from plasmid pCRBluntII-TOPO 889092 with primer pair AVG104/AVG105. Multiple PCR reactions were pooled, purified using a PCR purification kit, and ethanol precipitated to concentrate the amplified DNA fragment. The DNA thus prepared was used in the subsequent steps.

1.2. Generation of Strains 29-9 Δsfb3 and Morph Δsfb3 Lacking the sfb3 Gene

Strains Morph and 29-9 were transformed with the Δsfb3 deletion cassette by PEG-mediated transformation, and plated on Vogel's minimal medium containing hygromycin B and sorbitol. *Trichoderma* transformation is described, e.g., in U.S. Pat. No. 5,246,853. Candidates (684 for 29-9+Δsfb3 and 348 for Morph+Δsfb3) were transferred to Vogel's minimal medium containing hygromycin B to select for hygromycin B resistant candidates. Hygromycin B resistant transformants were transferred to Vogel's minimal medium or PDA containing Congo Red to assess Congo Red sensitivity. PCR analysis revealed one Congo Red-sensitive candidate from each transformation in which the Δsfb3 deletion cassette integrated at the sfb3 locus by homologous recombination (FIG. 3). Homologous integration of the Δsfb3 deletion cassette at the sfb3 locus in both 29-9 Δsfb3 and Morph Δsfb3 was verified by amplifying DNA fragments of the expected size using primer pairs AVG108/AVG109, AVG110/AVG111 and AVG108/AVG111. Primer pair AVG108/AVG109 amplifies a DNA fragment starting outside the 5' end of the AVG88/AVG89 deletion cassette region and ending within the hygromycin B resistance cassette. Primer pair AVG110/AVG111 amplifies a DNA fragment starting within the hygromycin B resistance cassette and ending outside the 3' end of the AVG92/AVG93 deletion cassette region. Primer pair AVG108/AVG110 amplifies the whole deletion cassette integrated at the sfb3 locus. The generated strains with confirmed homologous integration of the deletion cassette were named 29-9 Δsfb3 and Morph Δsfb3, respectively.

1.3. Growth of Strains 29-9, 70H2, and 29-9 Δsfb3 in Submerged Culture

Strains 29-9, 70112, and 29-9 Δsfb3 were grown under identical conditions in submerged (liquid) culture, and their growth phenotypes were compared.

Briefly, spores of each strain were added separately to 500-mL of medium in a 3-L flask with both side and bottom baffles. The medium contained 5 g/L (NH$_4$)$_2$SO$_4$, 4.5 g/L KH$_2$PO$_4$, 1 g/L MgSO$_4$.7H$_2$O, and 14.4 g/L citric acid, adjusted to pH 5.5 with 5% NaOH. After autoclaving for 30 minutes, sterile 60% glucose was added to a final concentration of 27.5 g/L, along with 2.5 mL/L of a trace element solution containing 175 g/L citric acid, 200 g/L FeSO$_4$.7H2O, 16 g/L ZnSO$_4$.7H$_2$O, 3.2 g/L CuSO$_4$.5H$_2$O, 1.4 g/L MnSO$_4$.H$_2$O, and 0.8 g/L H$_3$BO$_3$. The culture was grown for 48 hrs at 34° C. in a shaking incubator.

After 48 hrs, the contents of each flask were added separately to 15-L fermentors containing 9.5 L of medium containing 4.7 g/L KH$_2$PO$_4$, 1.0 g/L MgSO$_4$.7H$_2$O, 4.3 g/L (NH$_4$)$_2$SO$_4$ and 2.5 mL/L of the same trace element solution. These components were heat sterilized together at 121° C. for 30 minutes. A solution of 60% glucose and 0.48% CaCl$_2$.2H$_2$O was separately autoclaved, cooled, and added to the fermentor to a final concentration of 75 g/L glucose and 0.6 g/L CaCl$_2$.2H$_2$O. The medium was adjusted to pH 3.5 with 28% NH$_3$ and the temperature was maintained at 34° C. for the entire growth period.

A dissolved oxygen (DO) probe was calibrated to 100% when there was no added pressure in the headspace (i.e., 0 bar gauge, 1 bar absolute). The pressure in the headspace was then set to 0.7 bar (gauge), after which the oxygen probe read 170% before the seed culture was added. The fermentor contained two, four-blade turbines that provided mixing via a variable speed motor that was initially set at 500 rpm.

As the cultures grew, DO levels dropped, at least partly as a consequence of the increased viscosity of the broth clue to the proliferation of filamentous fungus hyphae. When DO fell below 40%, the agitation rate was increased to maintain the dissolved oxygen at 40%. If the DO did not fall below 40%, then it was unnecessary to increase the agitation rate during the fermentation run, and the initial agitation rate was higher than necessary. When the glucose was completely consumed, the amount of biomass produced in each fermentor was measured, and found to be substantially the same for all three strains.

The DO level in each fermentor at a given level of agitation, and the amount of agitation required to maintain a given DO level are indirect measures of the viscosity of the different broths, due to the different strain growth phenotypes. Although it would be ideal to vary only one variable (i.e., DO or agitation) and measure the other, it is desirable to prevent the DO from falling below 40% to ensure the production of sufficient biomass in each fermentor, thereby permitting a more meaningful comparison between the growth of the different strains.

Generally, where it is necessary to increase the agitation rate to maintain a target DO level, the amount of agitation can be estimated by the amount of power supplied to the motor driving the fermentor turbine, which provides a metric that correlates with the viscosity of the broth.

In particular, the extra power required to agitate the suspended culture is proportional to the agitation rate raised to the 3rd power. Table 4 shows the highest agitation rate required to maintain the dissolved oxygen at 40% at the end of the growth phase.

TABLE 4

Agitation rate required to maintain a DO of 40% at the end of the growth phase

| Strain | Agitation rate | Relative power increase from baseline at 500 rpm |
|---|---|---|
| 29-9 | 750 | $(750/500)^3 = 3.4$ |
| 70H2 | 539 | $(539/500)^3 = 1.3$ |
| 29-9 Δsfb3 | 540 | $(540/500)^3 = 1.3$ |

Under these growth conditions, the original strain, 29-9, required 2.6 times more power than either the 70H2 or 29-9 Δsfb3 strains in order to maintain a DO of 40% and produce the amount of biomass. Strains 70H2 and 29-9 Δsfb3 had similar viscosity properties, and produced similar levels of a protein of interest (TrGA) in suspended culture, demonstrating that a reduced viscosity growth phenotype can be imparted to a filamentous fungus by disrupting the sfb3 gene.

1.4. Elimination of the LoxP-Flanked Hygromycin B Resistance Cassette from Morph Δsfb3

Figure 4:
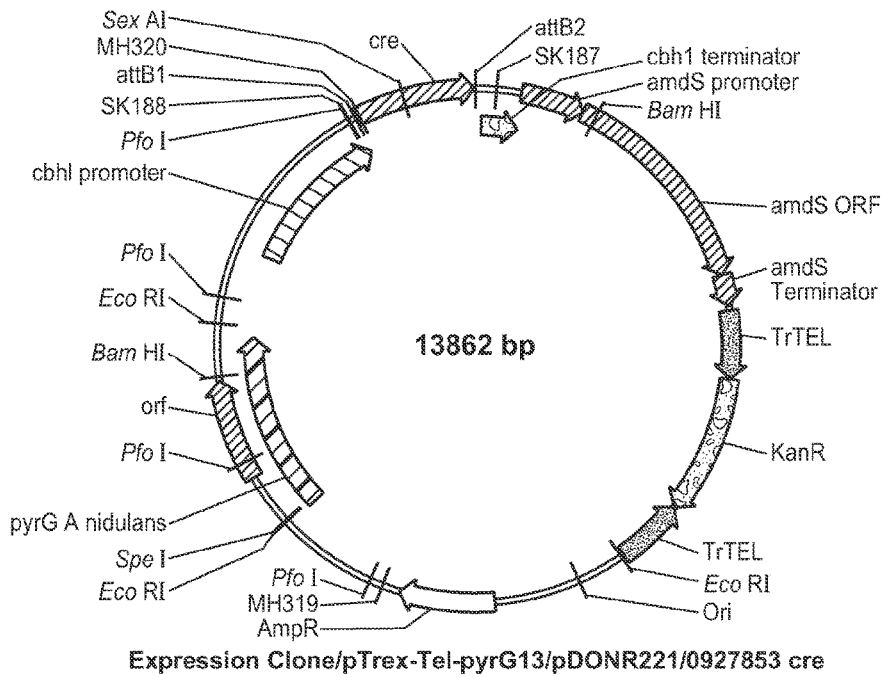
FIG. 4 is map of plasmid pTrex-Tel-pyrG13/pDONR221/0927853cre used to transiently express the ere gene in the Morph Δsfb3 strain.

The loxP-flanked hygromycin B resistance cassette was eliminated from strain Morph Δsfb3 by transiently expressing the cre gene which induced recombination between loxP sites. The Morph Δsfb3 strain was transformed with the cre-containing telomeric plasmid pTrex-Tel-pyrG13/pDONR221/0927853cre (FIG. 4) to induce recombination between loxP sites and eliminate the hygromycin B resistance cassette. This vector contains the amdS marker cassette allowing growth on medium containing acetamide. Transformants were transferred once to acetamide-containing medium, followed by three transfers to PDA medium to allow loss of the cre-containing telomeric plasmid. The transformants were then transferred in parallel to Vogel's medium containing hygromycin B to assess if the hygromycin B cassette was lost and acetamide-containing medium to assess if the cre-containing plasmid was lost (FIG. 5; PDA=Potato Dextrose Agar, VMH=Vogel's minimal medium with hygromycin B, amdS=minimal medium with acetamide, hph⁻=sensitive to hygromycin B, cre⁻=sensitive to presence of acetamide in medium). 91.8% of the transformants lost the hygromycin B cassette and 92.5% of the transformants lost the cre-containing plasmid. This demonstrated that it is possible to eliminate the hygromycin B cassette from the integrated Δsfb3 deletion cassette.

Figure 6:
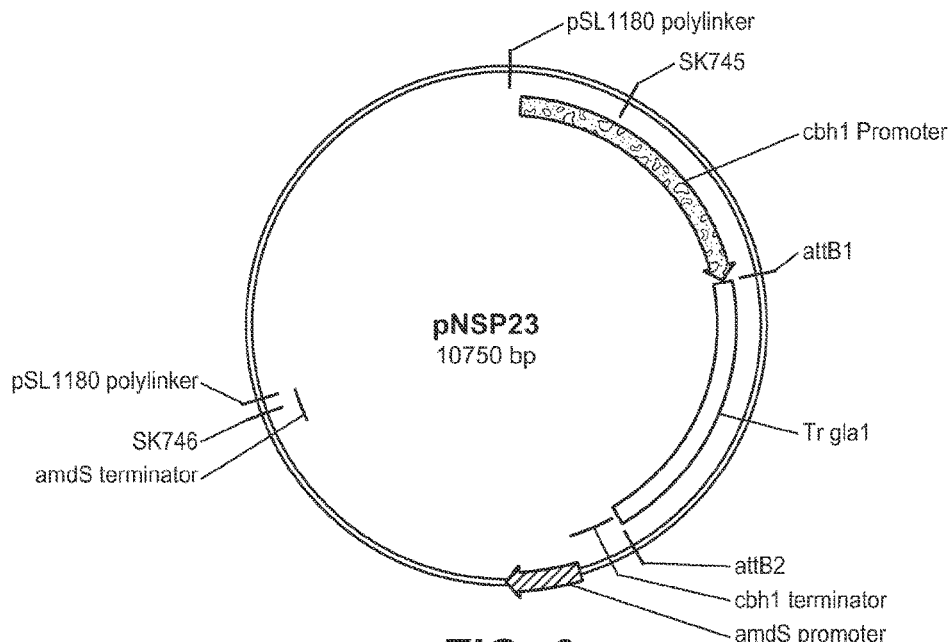
FIG. 6 is a map of plasmid pNSP23.

1.5. Expression of a Gene of Interest is not Impaired by Disruption of the Sfb3 Gene An expression cassette encoding a glucoamylase enzyme served as an exemplary gene of interest and provided a convenient way to measure the amount of protein secreted from the variant filamentous fungus strains. The glucoamylase expression cassette (i.e., TrglaA expression cassette), containing the cbhI promoter, the *T. reesei* glucoamylase gene TrglaA, and the cbhI terminator, fused to the amdS marker cassette, was PCR amplified from plasmid pNSP23 (FIG. 6) using primer pair SK745/SK746. Multiple PCR reactions were pooled, purified using a PCR purification kit, and ethanol precipitated to concentrate the amplified DNA fragment. The Morph Δsfb3 strain was transformed with the TrglaA expression cassette by PEG-mediated transformation, and then plated on acetamide minimal medium with sorbitol. Stable candidates were selected on acetamide minimal medium and transferred to induction medium in a microtiter plate format. The strains were grown in microtiter plates and the activity of glucoamylase in the supernatant was assayed using PNPG as the substrate.

The best Morph Δsfb3+TrglaA candidates had glucoamylase activity higher than the 29-9 strain (which also includes the TrglaA expression cassette). The supernatant glucoamylase activity of the top candidate was verified after growth in shake flasks, and confirmed the results obtained in microtiter plates. The results show that deletion of the sfb3 does not impair the expression or secretion of a protein of interest.

Example 2. Complementation of the 70H2 Strain with the Wild Type Sfb3 Gene 2.1. Generation of Constructs Containing the sfb3 Gene Four constructs containing the sfb3 gene were made. Primer pair AVG82/AVG83 was used to amplify the wild type sfb3 gene with its native promoter and terminator from 29-9 genomic DNA and the mutated sfb3 gene with its native promoter and terminator from 70H2 genomic DNA. Primer pair AVG84/AVG85 was used to amplify the wild type sfb3 gene from the start codon to the stop codon using 29-9 genomic DNA the mutated sfb3 gene from the start codon to the stop codon using 70H2 genomic DNA. The result was four PCR-amplified fragments containing the wild type or mutated sfb3 gene, with or without the native sfb3 promoter and terminator. Each of these four fragments was independently cloned into the pENTR/D-TOPO vector (Invitrogen, Carlsbad, Calif., USA).

Figure 7:
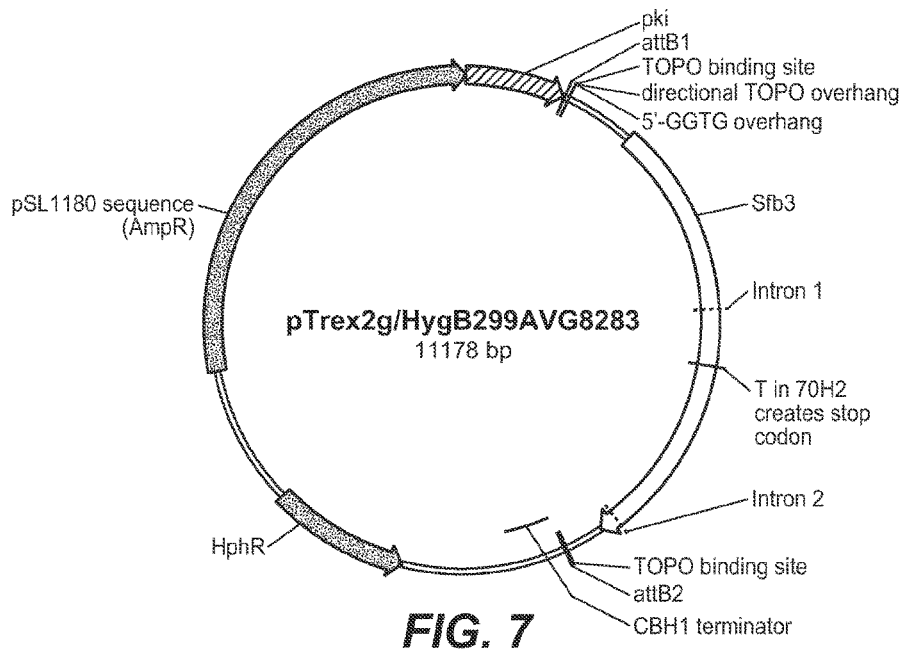
FIG. 7 is a map of one of four plasmids used for complementation in 70H2, this plasmid containing the wild type sfb3 gene with the native promoter and terminator.

In the next step the four pENTR/D-TOPO constructs were transferred to the destination vector pTrex2g/HygB using the LR clonase reaction. Each of the four constructs was amplified in *E. coli*, and obtained minipreps for each construct were vacuum concentrated. DNA prepared this way was used in the subsequent step. An exemplary destination construct is shown in FIG. 7.

2.2. Complementation of the 70H2 Phenotype with the sfb3 Gene

Each of the four destination vector constructs were separately transformed into 70H2 by PEG-mediated transformation, followed by plating on Vogel's minimal medium with hygromycin B. Thirty candidates from each of the four transformations were transferred to PDA with hygromycin B, and their phenotype compared to 70H2 and 29-9 transformed with the pTrex2g/HygB vector alone (as controls). All candidates transformed with the wild type sfb3 genes had a wild type phenotype similar to 29-9 on PDA medium with hygromycin B. All candidates transformed with the mutated sfb3 gene derived from 70H2 retained the 70H2 phenotype (FIG. 8). These results indicated that the wild type sfb3 gene derived from 29-9, but not the mutated sfb3 gene derived from 70H2, could impart a wild type phenotype to the 70H2 strain.

To confirm that the phenotype reversion was caused by the presence of the wild type sfb3 gene and not by a change in the chromosomal DNA, candidates were transferred four times on PDA medium (non-selective conditions) to look for candidates that lost the vector, and then back to selective medium with hygromycin B. For all candidates that were unstable and lost the plasmid (based on the loss of hygromycin B resistance), the loss of the plasmid correlated with the reappearance of the 70H2 phenotype. These results confirm that the wild type sfb3 was responsible for the restoring the wild type phenotype to 70H2.

2.3. Generation of a sfb3 Gene Replacement Cassette Containing the Wild Type sfb3 Gene A DNA sequence containing about ⅔ of the 3' end of the wild type sfb3 gene was amplified with primer pair AVG94/AVG95, which introduced a SpeI site at the 5' end of the fragment and a BglII site at the 3' end of the fragment. The hygromycin B resistance cassette flanked by loxP sites was amplified from plasmid pCR-Blunt II-hph-loxP#4 (FIG. 1) with primer pair AVG90/AVG91, which introduced a BglII site at the 5' end of the fragment and a NotI site at the 3' end of the fragment. A DNA sequence containing the 3' DNA sequence downstream of the sfb3 terminator region was amplified with primer pair AVG96/AVG97, which introduced a NotI site at the 5' end of the fragment and an XbaI site at the 3' end of the fragment.

Figure 9:
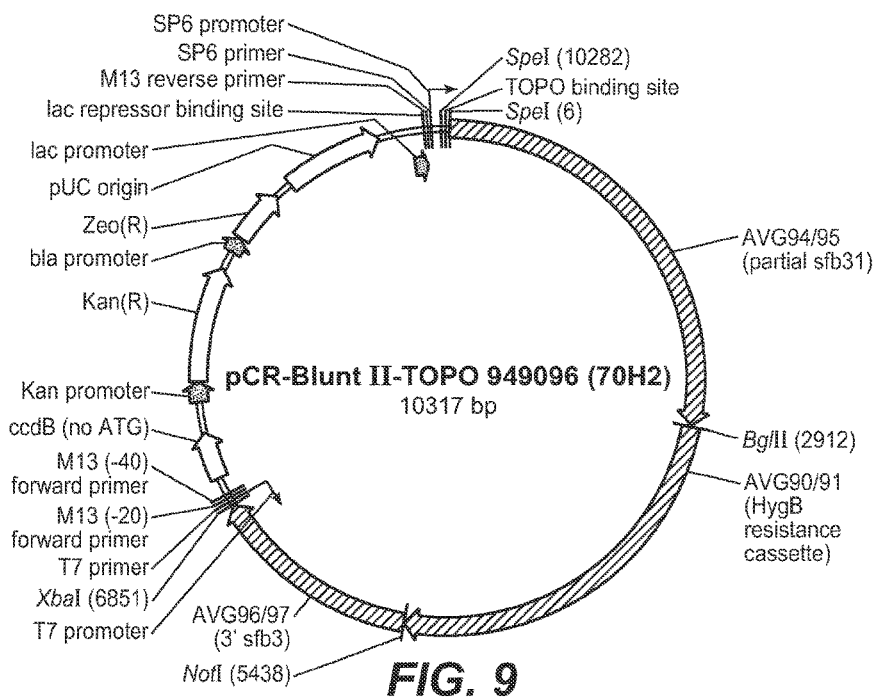
FIG. 9 is map of plasmid pCR-BluntII-TOPO 949096.

These three fragments were successively ligated into vector pCR®-Blunt II-TOPO® (Invitrogen Corp., Carlsbad, Calif., USA), and the resulting plasmid was named pCR-Blunt II-TOPO 949096 (FIG. 9). The two DNA sequences surrounding the hygromycin B resistance cassette were amplified using 29-9 genomic DNA as the template. The sfb3 gene replacement cassette, containing part of the sfb3 gene, the hygromycin B-resistance cassette surrounded by loxP sites at each end, and the 3' sequence downstream of sfb3, was amplified from plasmid pCR-Blunt II-TOPO 889092 with primers pair AVG102/AVG103, Multiple PCR reactions were pooled, purified using a PCR purification kit, and ethanol precipitated to concentrate the amplified DNA fragment. DNA prepared this way was used in the subsequent step.

Figure 10A:
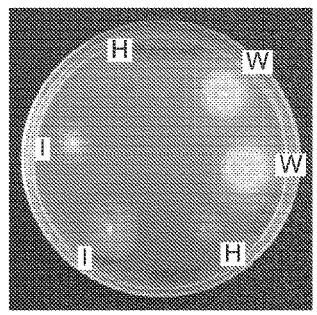
FIG. 10 is an image showing (A) the growth of transformants of 70H2 transformed with pCR-BluntII-TOPO 949096 containing the wild type sfb3 gene obtained from strain 29-9. The strains were incubated on VMH (Vogel's minimal medium containing hygromycin B) at 28° C. Two candidates have the wild type phenotype (W), two have the 70H2 phenotype (H), and two have an intermediate phenotype (I). (B) Comparison of 70H2sfb3#24, 70H2 and 29-9 on VM (Vogel's minimal medium) after 4 days of growth at 28° C. followed by 3 days of growth at room temperature.
Figure 10B:
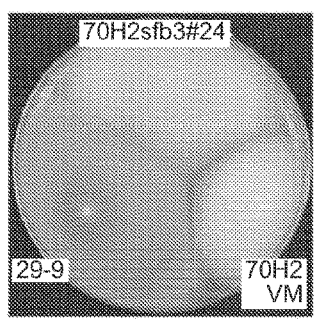

2.4. Complementation of the 70H2 Phenotype by Expression of the sfb3 Wild Type Gene from the Native sfb3 Locus Strain 70H2 was transformed with the sfb3 gene replacement cassette (described in section 2.3) by PEG-mediated transformation, followed by plating on Vogel's minimal medium containing hygromycin B and sorbitol. Fifteen candidates that had a wild type colony phenotype were transferred to Vogel's minimal medium containing hygromycin B to select for hygromycin B resistant candidates with a wild type colony phenotype. Stable candidates resistant to hygromycin B were selected on minimal medium containing hygromycin B and assessed for wild type colony phenotype (FIG. 10).

Homologous integration of the sfb3 gene replacement cassette at the sfb3 locus of 70H2 was verified by amplifying DNA fragments of the expected size using primer pairs AVG112/AVG113 and AVG114/AVG115. Primer pair AVG112/AVG113 amplified a DNA fragment starting outside the 5' end of the AVG94/AVG95 sfb3 gene replacement cassette region and ending within the hygromycin B resistance cassette. Primer pair AVG114/AVG115 amplified a DNA fragment starting within the hygromycin B resistance cassette and ending outside the 3' end of the AVG96/AVG97 sfb3 gene replacement cassette region.

The generated strain with confirmed homologous integration of the sfb3 gene replacement cassette was named 70112+wild type sfb3. This strain had a phenotype similar to 29-9. Thus, replacement of the mutated sfb3 gene in 70H2 with the wild type sfb3 gene, at the native sfb3 locus, restored the wild type phenotype to 70H2, providing further evidence that disruption of the sfb3 gene is responsible for the reduced-viscosity phenotype in 70112, Example 3. Growth of Strains 29-9, 70H2, and 29-9 ΔSfb3 in Submerged Culture Strains 29-9, 70H2, and 29-9 Δsfb3 were grown under identical conditions in submerged (liquid) culture, and their growth phenotypes were compared. Briefly, spores of each strain were added separately to 500 mL of medium in a 3-L flask with both side and bottom baffles. The medium contained 5 g/L $(NH_4)_2SO_4$, 4.5 g/L $KH_2PO_4$, 1 g/L $MgSO_4.7H_2O$, and 14.4 g/L citric acid, adjusted to pH 5.5 with 5% NaOH. After autoclaving for 30 minutes, sterile 60% glucose was added to a final concentration of 27.5 g/L, along with 2.5 mL/L of a trace element solution containing 175 g/L citric acid, 200 g/L $FeSO_4.7H2O$, 16 g/L $ZnSO_4.7H_2O$, 3.2 g/L $CuSO_4.5H_2O$, 1.4 g/L $MnSO_4.H_2O$, and 0.8 g/L $H_3BO_3$. The culture was grown for 48 hrs at 34° C. in a shaking incubator.

After 48 hrs, the contents of each flask were added separately to 15-L fermentors containing 9.5 L of medium containing 4.7 g/L $KH_2PO_4$, 1.0 g/L $MgSO_4.7H_2O$, 4.3 g/L $(NH_4)_2SO_4$ and 2.5 mL/L of the same trace element solution. These components were heat sterilized together at 121° C. for 30 minutes. A solution of 60% glucose and 0.48% $CaCl_2.2H_2O$ was separately autoclaved, cooled, and added to the fermentor to a final concentration of 75 g/L glucose and 0.6 g/L $CaCl_2.2H_2O$. The medium was adjusted to pH 3.5 with 28% $NH_3$ and the temperature was maintained at 34° C. for the entire growth period.

A dissolved oxygen (DO) probe was calibrated to 100% when there was no added pressure in the headspace (i.e., 0 bar gauge, 1 bar absolute). The pressure in the headspace was then set to 0.7 bar (gauge), after which the oxygen probe read 170% before the seed culture was added. The fermentor contained two, four-blade turbines that provided mixing via a variable speed motor that was initially set at 500 rpm.

As the cultures grew, DO levels dropped, at least partly as a consequence of the increased viscosity of the broth due to the proliferation of filamentous fungus hyphae. When DO fell below 40%, the agitation rate was increased to maintain the dissolved oxygen at 40%. If the DO did not fall below 40%, then it was unnecessary to increase the agitation rate during the fermentation run, and the initial agitation rate was higher than necessary. When the glucose was completely consumed, the amount of biomass produced in each fermentor was measured, and found to be substantially the same for all three strains.

The DO level in each fermentor at a given level of agitation, and the amount of agitation required to maintain a given DO level are indirect measures of the viscosity of the different broths, due to the different strain growth phenotypes. Although it would be ideal to vary only one variable (i.e., DO or agitation) and measure the other, it is desirable to prevent the DO from falling below 40% to ensure the production of sufficient biomass in each fermentor, thereby permitting a more meaningful comparison between the growth of the different strains.

Generally, where it is necessary to increase the agitation rate to maintain a target DO level, the amount of agitation can be estimated by the amount of power supplied to the motor driving the fermentor turbine, which provides a metric that correlates with the viscosity of the broth.

In particular, the extra power required to agitate the suspended culture is proportional to the agitation rate raised to the 3rd power. Table 4 shows the highest agitation rate required to maintain the dissolved oxygen at 40% at the end of the growth phase.

TABLE 4

Agitation rate required to maintain a DO of 40% at the end of the growth phase

| Strain | Agitation rate | Relative power increase from baseline at 500 rpm |
|---|---|---|
| 29-9 | 750 | $(750/500)^3 = 3.4$ |
| 70H2 | 539 | $(539/500)^3 = 1.3$ |
| 29-9 Δsfb3 | 540 | $(540/500)^3 = 1.3$ |

Under these growth conditions, the original strain, 29-9, required 2.6 times more power than either the 70H2 or 29-9 Δsfb3 strains in order to maintain a DO of 40% and produce the amount of biomass. Importantly, the 70H2 and 29-9 Δsfb3 strains had similar viscosity properties in suspended culture, demonstrating that a reduced viscosity growth phenotype can be imparted to a filamentous fungus by disrupting the sfb3 gene.

Example 4. Generating a ΔSfb3 H3A Strain for Producing a Whole Cellulase Composition 4.1 Generation of a Δsfb3 Deletion Cassette The DNA sequences flanking the 5' end of the *T. reesei* sfb3 gene was amplified with the primer pair AVG88/AVG89. Amplification of the fragment with this primer pair introduced a SalI site at the 5' end of the fragment and a BglII site at the 3' end of the fragment. The hygromycin B resistance cassette flanked by parallel loxP sites was amplified from plasmid pCR-Blunt II-hph-loxP#4 (FIG. 1) with primer pair AVG90/AVG91, introducing a BglII site at the 5' end of the fragment and a NotI site at the 3' end of the fragment. The DNA sequence flanking the 3' end of sfb3 was amplified with primer pair AVG92/AVG93, introducing a NotI site at the 5' end and an XbaI site at the 3' end of the fragment.

The above three fragments were successively ligated into vector pCR®-Blunt II-TOPO® (Invitrogen Corp., Carlsbad, Calif., USA), and the resulting plasmid was named pCR-Blunt II-TOPO 889092 (FIG. 2). The DNA sequences at the 5' and 3' flanks of the sfb3 gene were amplified using Morph TrglaA (29-9) genomic DNA as the template. The Δsfb3 deletion cassette containing the 5' sfb3 flank, the hygromycin B-resistance cassette surrounded by loxP sites at each end, and the 3' sfb3 flank, was amplified from plasmid pCRBluntH-TOPO 889092 with primer pair AVG104/AVG105. Multiple PCR reactions were pooled, purified using a PCR purification kit, and ethanol precipitated to concentrate the amplified DNA fragment. The DNA thus prepared was used in the subsequent steps.

4.2 Generation of Strain H3A Δsfb3 #1009 Lacking the sfb3 Gene

An H3A integrated *Trichoderma reesei* expression strain was prepared in accordance with the description of PCT/US2010/049849, published as WO/2011/038019, Strain H3A was transformed with the Δsfb3 deletion cassette by PEG (polyethylene glycol)-mediated transformation, and plated on Vogel's minimal medium containing hygromycin B and sorbitol. PEG-mediated transformation of Trichoderma was previously described, in e.g., U.S. Pat. No. 5,246,853.

1020 candidates were transferred to Vogel's minimal medium plates containing hygromycin B to select for hygromycin B-resistance. Hygromycin B-resistant candidates were then transferred to Vogel's minimal medium or a PDA medium containing Congo Red to assess Congo Red sensitivity.

PCR analysis of 43 stable candidates showing mild sensitivity to Congo Red was conducted, and one candidate, #1009, showed a profile consistent with homologous integration of the sfb3 deletion cassette into the H3A genome coupled with the elimination of the native sfb3 gene. Homologous integration of the Δsfb3 deletion cassette at the sfb3 locus in H3A Δsfb3 #1009 was verified by amplifying DNA fragments of the expected size using primer pairs AVG108/AVG109; AVG110/AVG111; and AVG108/AVG111. Specifically, primer pair AVG108/AVG109 amplified a DNA fragment starting outside the 5' end of the AVG88/AVG89 deletion cassette region and ending within the hygromycin B resistance cassette, Primer pair AVG110/AVG111 amplified a DNA fragment starting within the hygromycin B resistance cassette and ending outside the 3' end of the AVG92/AVG93deletion cassette region. Primer pair AVG108/AVG111 amplified the whole deletion cassette integrated at the sfb3 locus. Absence of the sfb3 gene was confirmed by absence of a PCR product when using primer pair AVG160/AVG161 designed to amplify an internal sfb3 fragment.

Figure 11:
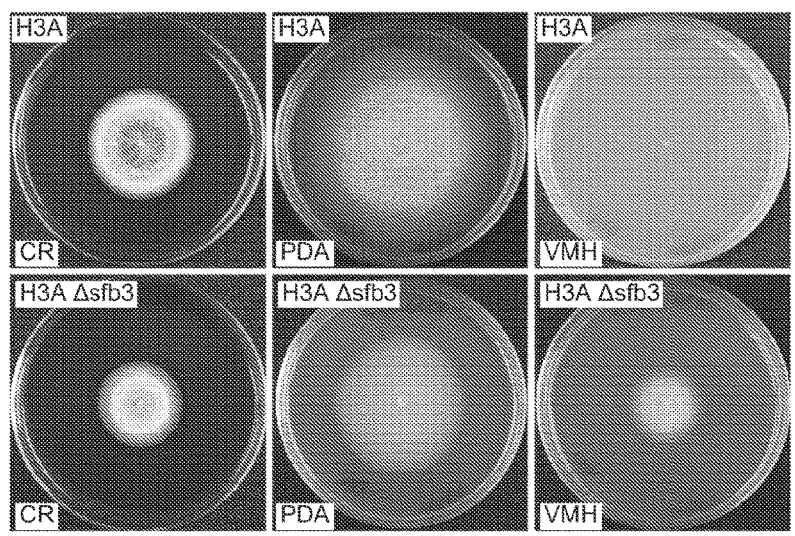
FIG. 11 shows the colony morphologies of H3A and H3A Δsfb3 #1009 on the indicated media after 4 days of growth at 28° C.
Figure 12:
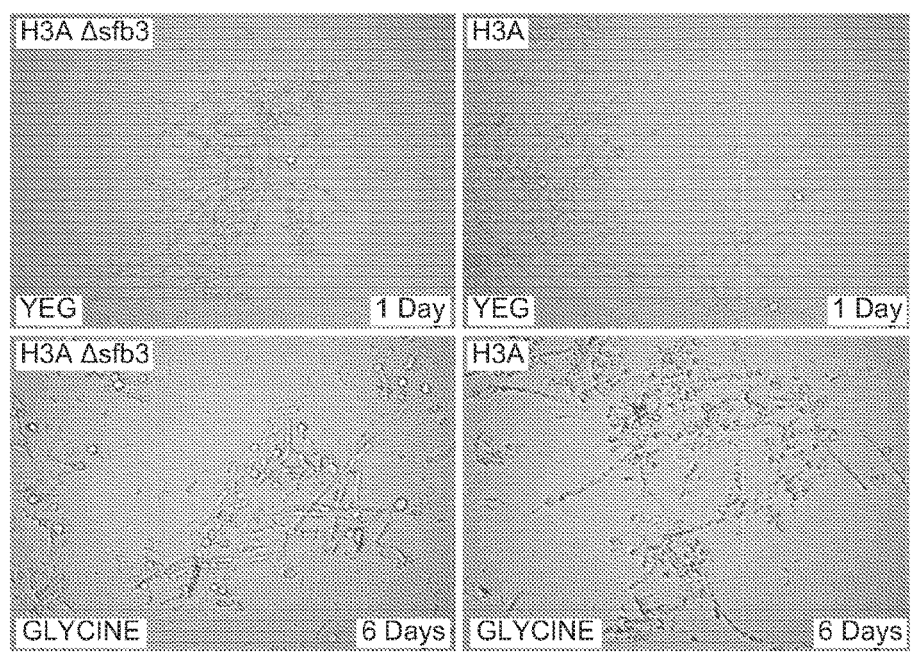
FIG. 12 show images of H3A and H3A Δsfb3 #1009 hyphae in liquid culture after the indicated periods of time at 28° C.

When compared to the H3A host strain, the H3A Δsfb3 #1009 strain had more restricted colony morphology on Congo Red-containing medium, a slower growth rate and reduced conidiation on PDA, and was able to grow on medium containing hygromycin B (FIG. 11). Liquid cultures of strains H3A and H3A Δsfb3 #1009 were also compared. Shake flask cultures of both strains were grown in 50 mL YEG or glycine minimal medium at 28° C. and 220 rpm for 1 or 6 days, respectively. In both YEG and glycine minimal medium strain H3A Δsfb3 #1009 generally had shorter-length hyphae (FIG. 12), suggesting improved viscosity properties.

4.3 Efficient Production of a Whole Cellulase Composition in H3A Δsfb3 #1009

Two fermentation runs were conducted side-by-side, one with 113A and the other with H3A Δsfb3 #1009, under standard fermentation conditions, as described, for example, in PCT/US2010/049849. An agitation rate of 500 rpm was used in each fermentation tank. Dissolved oxygen was measured at the end of the growth phase, using a Hamilton Optical Oxygen sensor (Hamilton Company, USA, Reno Nev.). A comparison of the DO levels is shown in Table 5, below:

TABLE 5

DO following growth phase

| Strain | Agitation (rpm) | Dissolved Oxygen at End of Growth Phase | Fold Increase in Available Dissolved Oxygen |
|---|---|---|---|
| H3A | 500 | 100% | 100%/100% = 1.0 |
| H3A Δsfb3 #1009 | 500 | 120% | 120%/100% = 1.2 |

The resulting whole cellulase compositions from each of the fermentation runs were characterized using an HPLC method, as described, for example, in PCT/US2010/049849. The amounts of major cellulases/hemicellulases contained therein are compared side-by-side in Table is 6, below:

TABLE 6

Comparison of the cellulases/hemicellulases present in a whole cellulase composition

| Cellulase/hemicellulase | H3A Δsfb3 | H3A |
|---|---|---|
| Fv3A | 7% | 7% |
| FV43D/Fv51A | 12% | 14% |
| Xyn3 | 14% | 12% |
| Bgl1 | 10% | 7% |
| CBH1 | 33% | 40% |
| EGLs | 12% | 8% |
| CBH2 | 7% | 9% |

Both whole cellulase compositions contained substantially the same amounts of each major component, indicating that protein expression in H3A Δsfb3 #1009 was similar to that of H3A.

Although the foregoing compositions and methods have been described in some detail by way of illustration and examples for purposes of clarity of understanding, it will be apparent to those skilled in the art that certain changes and modifications may be made. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

What is claimed is:

1. A variant strain of *Trichoderma reesei* derived from a parental strain, the variant strain comprising a complete deletion of sfb3 gene, wherein the cells of the variant strain produce during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain; and wherein the variant strain further comprises a gene encoding a protein of interest.

2. The variant strain of claim 1, wherein deletion of the sfb3 gene is the primary genetic determinant for conferring a reduced viscosity phenotype to the variant strain.

* * * * *